(12) United States Patent
Mayo

(10) Patent No.: US 7,144,982 B2
(45) Date of Patent: Dec. 5, 2006

(54) POLYPEPTIDES WITH THERAPEUTIC ACTIVITY AND METHODS OF USE

(75) Inventor: Kevin H. Mayo, Minnetonka, MN (US)

(73) Assignee: University of Minnesota, Minneapolis, MN (US)

( * ) Notice: Subject to any disclaimer, the term of this patent is extended or adjusted under 35 U.S.C. 154(b) by 846 days.

(21) Appl. No.: 09/766,353

(22) Filed: Jan. 19, 2001

(65) Prior Publication Data

US 2002/0146406 A1  Oct. 10, 2002

Related U.S. Application Data

(60) Provisional application No. 60/210,297, filed on Jun. 8, 2000, provisional application No. 60/177,255, filed on Jan. 20, 2000.

(51) Int. Cl.
- A61K 38/04 (2006.01)
- A61K 38/10 (2006.01)
- C07K 7/08 (2006.01)

(52) U.S. Cl. ............... 530/327; 530/300; 514/14; 514/15

(58) Field of Classification Search ............... 530/300, 530/327; 514/14, 15
See application file for complete search history.

(56) References Cited

U.S. PATENT DOCUMENTS

| | | |
|---|---|---|
| 4,938,949 A | 7/1990 | Borch et al. |
| 5,595,887 A | 1/1997 | Coolidge et al. |
| 5,786,324 A | 7/1998 | Gray et al. |
| 5,830,860 A | 11/1998 | Gray et al. |
| 5,837,678 A | 11/1998 | Little, II |
| 5,854,214 A | 12/1998 | Little, II |
| 5,856,302 A | 1/1999 | Ammons et al. |
| 5,955,577 A | 9/1999 | Mayo |

FOREIGN PATENT DOCUMENTS

| | | |
|---|---|---|
| EP | 0 955 312 A2 | 11/1999 |
| WO | WO 99/17616 | 4/1999 |
| WO | WO 01/53335 | 7/2001 |

OTHER PUBLICATIONS

Olee et al. Database Caplus, Journal of Neuroimmunology (1989), 21(2-3), 235-40.*

Ngo et al . In: The protein folding and tertiary structure prediction, K. Mertz and S. Le Grand, Eds. Birkhauser, Boston, 1994, pp. 491-495.*

Agerberth et al., "Amino acid sequence of PR-39. Isolation from pig intestine of a new member of the family of proline-arginine-rich antibacterial peptides," *European Journal of Biochemistry*, 202(3):849-854 (1991).

Alvarez-Bravo et al., "Mode of Action of an Antibacterial Peptide, KLKLLLLLKLK-NH$_2$," *The Journal of Biochemistry* (Tokyo ), 117(6):1312-1316 (1995).

Andreu et al., "N-Terminal Analogues of Cecropin A: Synthesis, Antibacterial Activity, and Conformational Properties," *Biochemistry*, 24(7):1683-1688 (1985).

Andreu et al., "Animal Antimicrobial Peptides: An Overview." *Biopolymers Peptide Science*, 47(6):415-433 (1998).

(Continued)

*Primary Examiner*—Michael Borin
(74) *Attorney, Agent, or Firm*—Mueting, Raasch & Gebhardt, P.A.

(57) ABSTRACT

Polypeptides and methods of use including treating bacterial infection and/or endotoxemia, decreasing the amount of TNF-α, inhibiting endothelial cell proliferation, inhibiting angiogenic-factor mediated inter-cellular adhesion molecule expression down-regulation, and inhibiting angiogenesis.

24 Claims, 9 Drawing Sheets

βpep-19.  S I Q K L N V S M K L F R K Q A K W K I I V K L N D G R E L S L D-NH2 (SEQ ID NO: 18)

βpep-25.  A N I K L S V Q M K L F K R H L K W K I I V K L N D G R E L S L D-NH2 (SEQ ID NO: 19)

SC-1  A N I K L S V Q M K L F-NH2 (SEQ ID NO: 1)
SC-2      K L S V Q M K L F K R H-NH2 (SEQ ID NO: 2)
SC-3          V Q M K L F K R H L K W-NH2 (SEQ ID NO: 3)
SC-4              K L F K R H L K W K I I-NH2 (SEQ ID NO: 4)
SC-5                  K R H L K W K I I V K L-NH2 (SEQ ID NO: 5)
SC-6                      L K W K I I V K L N D G-NH2 (SEQ ID NO: 6)
SC-7                          K I I V K L N D G R E L-NH2 (SEQ ID NO: 7)
SC-8                              V K L N D G R E L S L D-NH2 (SEQ ID NO: 8)

OTHER PUBLICATIONS

Griffioen et al., "Endothelial Intercellular Adhesion Molecule-1 Expression Is Suppressed in Human Malignancies: The Role of Angiogenic Factors," *Cancer Research*, 56(5):1111-1117 (1996).

Griffioen et al., "Tumor Angiogenesis Is Accompanied by a Decreased Inflammatory Response of Tumor-Associated Endothelium," *Blood*, 88(2):667-673 (1996).

Griffioen et al., "Angiogenesis, a target for tumor therapy," *Journal of Laboratory and Clinical Medicine*, 132(5):363-368 (1998).

Griffioen et al., "Angiogenesis inhibitors overcome tumor induced endothelial cell anergy," *International Journal of Cancer*, 80(2):315-319 (1999).

Groenewegen et al., "Supernatants of human leukocytes contain mediator, different from interferon γ, which induces expression of MHC class II antigens," *The Journal of Experimental Medicine*, 164(1):131-143 (1986).

Hanzawa et al., "$^1$H nuclear magnetic resonance study of the solution conformation of an antibacterial protein, sapecin," *FEBS Letters*, 269(2):413-420 (1990).

Heumann et al., "Competition between Bactericidal/Permeability-Increasing Protein and Lipopolysaccharide-Binding Protein for Lipopolysaccharide Binding to Monocytes," *The Journal of Infectious Diseases*, 167(6):1351-1357 (1993).

Hill et al., "Crystal Structure of Defensin HNP-3, an Amphiphilic Dimer: Mechanisms of Membrane Permeabilization," *Science*, 251(5000):1481-1485 (1991).

Hoess et al., "Crystal structure of an endotoxin-neutralizing protein from the horseshoe crab, *Limulus* anti-LPS factor, at 1.5 Å resolution," *EMBO Journal*, 12(9):3351-3356 (1993).

Holak et al., "The Solution Conformation of the Antibacterial Peptide Cecropin A: A Nuclear Magnetic Resonance and Dynamical Simulated Annealing Study," *Biochemistry*, 27(20):7620-7629 (1988).

Homma, "A New Antigenic Schema and Live-cell Slide-agglutination Procedure for the Infrasubspecific, Serologic Classification of *Pseudomonas aeruginosa*," *The Japanese Journal of Experimental Medicine*, 46(6):329-336 (1976).

Hovde et al., "Characterization of a Protein from Normal Human Polymorphonuclear Leukocytes with Bactericidal Activity against *Pseudomonas aeruginosa*," *Infection and Immunity*, 54(1):142-148 (1986).

Ilyina et al., "NMR Structure of a *de Novo* Designed, Peptide 33mer with Two Distinct, Compact β-Sheet Folds," *Biochemistry*, 36(17):5245-5250 (1997).

Johnson, Jr., "Protein Secondary Structure and Circular Dichroism: A Practical Guide," *Proteins: Structure, Function, and Genetics*, 7(3):205-214 (1990).

Johnson et al., "Defining Inoculation Conditions for the Mouse Model of Ascending Urinary Tract Infection that Avoid Immediate Vesicoureteral Reflux yet Produce Renal and Bladder Infection," *The Journal of Infectious Diseases*, 173(3):746-749 (1996).

Johnson et al., "A Novel Multiply Primed Polymerase Chain Reaction Assay for Identification of Variant *papG* Genes Encoding the Gal(α1-4)Gal-Binding PapG Adhesins of *Escherichia coli*," *The Journal of Infectious Diseases*, 173(4):920-926 (1996).

Kawano et al., "Antimicrobial Peptide, Tachyplesin I, Isolated from Hemocytes of the Horseshoe Crab (*Tachypleus tridentatus*). NMR determination of the β-sheet structure," *The Journal of Biological Chemistry*, 265(26):15365-15367 (1990).

Kelly et al., "Role of bactericidal permeability-increasing protein in the treatment of gram-negative pneumonia," *Surgery*, 114(2):140-146 (1993).

Kitayama et al., "Suppressive Effect of Basic Fibroblast Growth Factor on Transendothelial Emigration of CD4(+) T-Lymphocyte," *Cancer Research*, 54(17):4729-4733 (1994).

Koning et al., "Calculation of the Nuclear Overhauser Effect and the Determination of Proton—Proton Distances in the Presence of Internal Motions," *Journal of Magnetic Resonance*, 90(1):111-123 (1990).

Lee et al., "Antibacterial peptides from pig intestine: Isolation of a mammalian cecropin," *Proceedings of the National Academy of Sciences (USA)*. 86(23):9159-9162 (1989).

Lehrer et al., "Defensins: Endogenous Antibiotic Peptides of Animal Cells," *Cell*, 64(2):229-230 (1991).

Little et al., "Functional Domains of Recombinant Bactericidal/Permeability Increasing Protein (rBPI$_{23}$)," *The Journal of Biological Chemistry*, 269(3):1865-1872 (1994).

Maloy et al., "Structure-Activity Studies on Magainins and Other Host defense Peptides," *Biopolymers Peptide Science*, 37(2):105-122 (1995).

Marion et al., "Application of phase sensitive two-dimensional correlated spectroscopy (COSY) for measurements of $^1$H—$^1$H spin—spin coupling constants in proteins," *Biochemical and Biophysical Research Communications*, 113(3):967-974 (1983).

Marion et al., "A two-dimensional NMR study of the antimicrobial peptide magainin 2," *FEBS Letters*, 227(1):21-26 (1988).

Marra et al., "Bactericidal/permeability-increasing protein has endotoxin-neutralizing activity," *The Journal of Immunology*, 144(2):662-666 (1990).

Marra et al., "The role of bactericidal/permeability-increasing protein as a natural inhibitor of bacterial endotoxin," *The Journal of Immunology*, 148(2):532-537 (1992).

Matsuyama et al., "Purification of Three Antibacterial Proteins from the Culture Medium of NIH-Sape-4, an Embryonic Cell Line of *Sarcophaga peregrina*," *The Journal of Biological Chemistry*, 263(32):17112-17116 (1988).

Matsuzaki et al., "Modulation of Magainin 2-Lipid Bilayer Interactions by Peptide Charge," *Biochemistry*, 36(8):2104-2111 (1997).

Mayo et al., "A recipe for designing water-soluble, β-sheet-forming peptides," *Protein Science*, 5(7):1301-1315 (1996).

Mayo et al., "Designed β-sheet-forming peptide 33mers with potent human bactericidal/permeability increasing protein-like bactericidal and endotoxin neutralizing activities," *Biochimica et Biophysica Acta*, 1425(1):81-92 (1998).

Mayo et al., "Structure-function relationships in novel peptide dodecamers with broad-spectrum bactericidal and endotoxin-neutralizing activities," *Biochemical Journal*, 349(3):717-728 (2000).

Melder et al., "During angiogenesis, vascular endothelial growth factor and basic fibroblast growth factor regulate natural killer cell adhesion to tumor endothelium," *Nature Medicine*, 2(9):992-997 (1996).

Millhauser, "Views of Helical Peptides: A Proposal for the Position of $3_{10}$-Helix along the Thermodynamic Folding Pathway," *Biochemistry*, 34(12):3873-3877 (1995).

Morrison et al., "Binding of polymyxin B to the lipid A portion of bacterial lipopolysaccharides," *Immunochemistry*, 13(10):813-818 (1976).

Mosmann, "Rapid Colorimetric Assay for Cellular Growth and Survival: Application to Proliferation and Cytotoxicity Assays," *Journal of Immunological Methods*, 65(1-2):55-63 (1983).

Oren et al., "Mode of Action of Linear Amphipathic α-Helical Antimicrobial Peptides," *Biopolymers Peptide Science*, 47(6):451-463 (1998).

Ørskov et al., "Complete Sequences of Glucagon-like Peptide-1 from Human and Pig Small Intestine," *The Journal of Biological Chemistry*, 264(22):12826-12829 (1989).

Piali et al., "Endothelial Vascular Cell Adhesion Molecule 1 Expression Is Suppressed by Melanoma and Carcinoma," *The Journal of Experimental Medicine*, 181(2):811-816 (1995).

Pouny et al., "Interaction of Antimicrobial Dermaseptin and Its Fluorescently Labeled Analogues with Phospholipid Membranes," *Biochemistry*, 31(49):12416-12423 (1992).

Ried et al., "High Affinity Endotoxin-binding and Neutralizing Peptides Based on the Crystal Structure of Recombinant *Limulus* Anti-lipopolysaccharide Factor," *The Journal of Biological Chemistry*, 271(45):28120-28127 (1996).

Rustici et al., "Molecular Mapping and Detoxification of the Lipid A Binding Site by Synthetic Peptides," *Science*, 259(5093):361-365 (1993).

Schlievert et al., "Production of Staphylococcal Pyrogenic Exotoxin Type C: Influence of Physical and Chemical Factors," *The Journal of Infectious Diseases*, 147(2):236-242 (1983).

Selsted et al., "Determination of Disulfide Array in the Human Defensin HNP-2. A Covalently Cyclized Peptide," *The Journal of Biological Chemistry*, 264(7):4003-4007 (1989).

Siefferman et al., "*Pseudomonas aeruginosa* Variants Isolated from Patients with Cystic Fibrosis Are Killed by a Bactericidal Protein from Human Polymorphonuclear Leukocytes,"*Infection and Immunity*, 59(6):2152-2157 (1991).

Springer, "Traffic Signals for Lymphocyte Recirculation and Leukocyte Emigration: The Multistep Paradigm," *Cell*, 76(2):301-314 (1994).

Spitznagel, "Antibiotic Proteins of Human Neutrophils," *The Journal of Clinical Investigation*, 86(5):1381-1386 (1990).

Sreerama et al., "A Self-Consistent Method for the Analysis of Protein Secondary Structure from Circular Dichroism," *Analytical Biochemistry*, 209(1):32-44 (1993).

States et al., "A Two-Dimensional Nuclear Overhauser Experiment with Pure Absorption Phase in Four Quadrants," *Journal of Magnetic Resonance*, 48:286-292 (1982).

Toniolo et al. "Circular Dichroism Spectrum of a Peptide $3_{10}$ Helix," *Journal of the American Chemical Society*, 118(11):2744-2745 (1996).

Tropp, "Dipolar relaxation and nuclear Overhauser effects in non-rigid molecules: The effect of fluctuating internuclear distances," *The Journal of Chemical Physics*, 72(11):6035-6043 (1980).

Velucchi et al., "Molecular Requirements of Peptide Structures Binding to the Lipid-A Region of Bacterial Endotoxins," *Vaccines*, 94 :141-146 (1994).

Warren et al., "Endotoxin Neutralization with Rabbit Antisera to *Escherichia coli* J5 and Other Gram-Negative Bacteria," *Infection and Immunity*, 55(7):1668-1673 (1987).

Wasiluk et al. "Comparison of Granule Proteins from Human Polymorphonuclear Leukocytes Which Are Bactericidal toward *Pseudomonas aeruginosa*," *Infection and Immunity*, 59(11):4193-4200 (1991).

Waterhous et al., "Importance of Environment in Determining Secondary Structure in Proteins," *Biochemistry*, 33(8):2121-2128 (1994).

Weiss et al., "Human Bactericidal/Permeability-increasing Protein and a Recombinant $NH_2$-Terminal Fragment Cause Killing of Serum-resistant Gram-negative Bacteria in Whole Blood and Inhibit Tumor Necrosis Factor Release Induced by the Bacteria," *The Journal of Clinical Investigation*, 90(3):1122-1130 (1992).

Wider et al., "Homonuclear Two-Dimensional $^1$H NMR of Proteins. Experimental Procedures," *Journal of Magnetic Resonance*, 56:207-234 (1984).

Wishart et al., "The Chemical Shift Index: A Fast and Simple Method for the Assignment of Protein Secondary Structure through NMR Spectroscopy," *Biochemistry*, 31(6):1647-1651 (1992).

Wüthrich et al., "Pseudo-structures for the 20 Common Amino Acids for Use in Studies of Protein Conformations by Measurements of Intramolecular Proton—Proton Distance Constraints with Nuclear Magnetic Resonance," *Journal of Molecular Biology*, 169(4):949-961 (1983).

Wüthrich, *NMR of Proteins and Nucleic Acids*, Wiley-Interscience, John Wiley and Sons, Inc., New York, NY, Title page, publication page, and table of contents, 4 pgs. (1986).

Yang et al., "Subunit Association and Structural Analysis of Platelet Basic Protein and Related Proteins Investigated by $^1$H NMR Spectroscopy and Circular Dichroism," *The Journal of Biological Chemistry*, 269(31):20110-20118 (1994).

Young et al., "An Invertebrate Coagulation System Activated by Endotoxin: Evidence for Enzymatic Mediation," *The Journal of Clinical Investigation*, 51(7):1790-1797 (1972).

Zasloff, "Magainins, a class of antimicrobial peptides from *Xenopus* skin: Isolation, characterization of two active forms, and partial cDNA sequence of a precursor," *Proceedings of the National Academy of Sciences (USA)*, 84(15):5449-5453 (1987).

Zasloff et al., "Antimicrobial activity of synthetic magainin peptides and several analogues," *Proceedings of the National Academy of Sciences (USA)*, 85(3):910-913 (1988).

Dings, Ruud P.M., "Pre-clinical Development of Anginex and Design of Small-Peptide Mimetics", Aug. 6, 1977.

Merrill et al., "Identification of a Chameleon-like pH-Sensitive Segment within the Colicin E1 Channel Domain That May Serve as the pH-Activated Trigger for Membrane Bilayer Association", *Biochemistry* 1997, 36, 6874-6884.

Minor et al., "Context-Dependent Secondary Structure Formation of a Designed Protein Sequence", *Nature*, vol. 380, Apr. 25, 1996, 730-734.

Barendsz-Janson et al., "In vitro Tumor Angiogenesis Assays: Plasminogen Lysine Binding Site 1 Inhibits in vitro Tumor-Induced Angiogenesis," *Journal of Vascular Research*, 35(2):109-114 (1998).

Battafarano et al., "Peptide derivatives of three distinct lipopolysaccharide binding proteins inhibit lipopolysaccharide-induced tumor necrosis factor-alpha secretion in vitro," *Surgery*, 118(2):318-324 (1995).

Bax et al., "MLEV-17-Based Two-Dimensional Homonuclear Magnetization Transfer Spectroscopy," *Journal of Magnetic Resonance*, 65:355-360 (1985).

Beamer et al., "Crystal Structure of Human BPI and Two Bound Phospholipids at 2.4 Angstrom Resolution," *Science*, 276(5320):1861-1864 (1997).

Bevilacqua, "Endothelial-leukocyte adhesion molecules," *Annual Review of Immunology*, 11:767-804 (1993).

Bodenhausen et al., "Multiple Quantum Spin-Echo Spectroscopy," *Journal of Magnetic Resonance*, 37:93-106. (1980).

Bohach et al., "Analysis of Toxic Shock Syndrome Isolates Producing Staphylococcal Enterotoxins B and C1 with Use of Southern Hybridization and Immunologic Assays," *Reviews of Infectious Diseases*, 11(Suppl 1):S75-S82 (1989).

Brünger et al., "Three-dimensional structure of proteins determined by molecular dynamics with interproton distance restraints: Application to crambin," *Proceedings of the National Academy of Sciences (USA)*, 83(11):3801-3805 (1986).

Brünger, *X-plor Manual (Version 3.1) A System for X-ray Crystallography and NMR*, Yale University Press, New Haven, CT, Title page, publication page, and table of contents, 13 pgs (1992).

Budson et al., "The Angiogenesis Inhibitor AGM-1470 Selectively Increases E-Selectin," *Biochemical and Biophysical Research Communications*, 225(1):141-145 (1996).

Clore et al., "Application of Molecular Dynamics with Interproton Distance Restraints to Three-dimensional Protein Structure Determination. A Model Study of Crambin," *Journal of Molecular Biology*, 191(3):523-551 (1986).

Cody et al. "Protective Anti-lipopolysaccharide Monoclonal Antibodies Inhibit Tumor Necrosis Factor Production," *Journal of Surgical Research*, 52(4):314-319 (1992).

Darveau et al., "Peptides Related to the Carboxyl Terminus of Human Platelet Factor IV with Antibacterial Activity," *The Journal of Clinical Investigation*, 90(2):447-455 (1992).

Delaglio et al., "NMRPipe: A multidimensional spectral processing system based on UNIX pipes," *Journal of Biomolecular NMR*, 6(3):277-293 (1995).

Dunn et al., "Efficacy of type-specific and cross-reactive murine monoclonal antibodies directed against endotoxin during experimental sepsis," *Surgery*, 98(2):283-290 (1985).

Dyson et al., "Folding of Immunogenic Peptide Fragments of Proteins in Water Solution. II. The Nascent Helix," *Journal of Molecular Biology*, 201(1):201-217 (1988).

Ehrenstein et al., "Electrically gated ionic channels in lipid bilayers," *Quarterly Reviews of Biophysics*, 10(1):1-34 (1977).

Folkman, "What Is the Evidence That Tumors Are Angiogenesis Dependent?" *Journal of the National Cancer Institute*, 82(1):4-6 (1990).

Folkman et al., "Angiogenesis," *The Journal of Biological Chemistry*, 267(16):10931-10934 (1992).

Fields et al. "Chapter 3: Principles and Practice of Solid-Phase Peptide Synthesis," in *Synthetic Peptides: A User's Guide*, W. M. Freeman & Company, New York, NY, pp. 77-183 (1992).

Gazit et al., "Interaction of the Mammalian Antibacterial Peptide Cecropin P1 with Phospholipid Vesicles," *Biochemistry*, 34(36):11479-11488 (1995).

Gazzano-Santoro et al., "High-Affinity Binding of the Bactericidal/Permeability-Increasing Protein and a Recombinant Amino-Terminal Fragment to the Lipid A Region of Lipopolysaccharide," *Infection and Immunity*, 60(11):4754-4761 (1992).

Gray et al., "B/PI-derived synthetic peptides: synergistic effects in tethered bactericidal and endotoxin neutralizing peptides," *Biochimica et Biophysica Acta*, 1244(1):185-190 (1995).

Greenfield et al., "Computed Circular Dichroism Spectra for the Evaluation of Protein Conformation," *Biochemistry*, 8(10):4108-4116 (1969).

* cited by examiner

βpep-19. S I Q K L N V S M K L F R K Q A K W K I I V K L N D G R E L S L D-NH2 (SEQ ID NO: 18)

βpep-25. A N I K L S V Q M K L F K R H L K W K I I V K L N D G R E L S L D-NH2 (SEQ ID NO: 19)

SC-1  A N I K L S V Q M K L F-NH2 (SEQ ID NO: 1)
SC-2  K L S V Q M K L F K R H-NH2 (SEQ ID NO: 2)
SC-3  V Q M K L F K R H L K W-NH2 (SEQ ID NO: 3)
SC-4  K L F K R H L K W K I I-NH2 (SEQ ID NO: 4)
SC-5  K R H L K W K I I V K L-NH2 (SEQ ID NO: 5)
SC-6  L K W K I I V K L N D G-NH2 (SEQ ID NO: 6)
SC-7  K I I V K L N D G R E L-NH2 (SEQ ID NO: 7)
SC-8  V K L N D G R E L S L D-NH2 (SEQ ID NO: 8)

Fig. 1

SEQUENCE LISTING

```
<160> NUMBER OF SEQ ID NOS: 20

<210> SEQ ID NO 1
<211> LENGTH: 12
<212> TYPE: PRT
<213> ORGANISM: ARTIFICIAL
<220> FEATURE:
<223> OTHER INFORMATION: SYNTHETIC POLYPEPTIDE

<400> SEQUENCE: 1

Ala Asn Ile Lys Leu Ser Val Gln Met Lys Leu Phe
1               5                   10

<210> SEQ ID NO 2
<211> LENGTH: 12
<212> TYPE: PRT
<213> ORGANISM: ARTIFICIAL
<220> FEATURE:
<223> OTHER INFORMATION: SYNTHETIC POLYPEPTIDE
```

```
<400> SEQUENCE: 2

Lys Leu Ser Val Gln Met Lys Leu Phe Lys Arg His
 1               5                  10

<210> SEQ ID NO 3
<211> LENGTH: 12
<212> TYPE: PRT
<213> ORGANISM: ARTIFICIAL
<220> FEATURE:
<223> OTHER INFORMATION: SYNTHETIC POLYPEPTIDE

<400> SEQUENCE: 3

Val Gln Met Lys Leu Phe Lys Arg His Leu Lys Trp
 1               5                  10

<210> SEQ ID NO 4
<211> LENGTH: 12
<212> TYPE: PRT
<213> ORGANISM: ARTIFICIAL
<220> FEATURE:
<223> OTHER INFORMATION: SYNTHETIC POLYPEPTIDE

<400> SEQUENCE: 4

Lys Leu Phe Lys Arg His Leu Lys Trp Lys Ile Ile
 1               5                  10

<210> SEQ ID NO 5
<211> LENGTH: 12
<212> TYPE: PRT
<213> ORGANISM: ARTIFICIAL
<220> FEATURE:
<223> OTHER INFORMATION: SYNTHETIC POLYPEPTIDE

<400> SEQUENCE: 5

Lys Arg His Leu Lys Trp Lys Ile Ile Val Lys Leu
 1               5                  10

<210> SEQ ID NO 6
<211> LENGTH: 12
<212> TYPE: PRT
<213> ORGANISM: ARTIFICIAL
<220> FEATURE:
<223> OTHER INFORMATION: SYNTHETIC POLYPEPTIDE

<400> SEQUENCE: 6

Leu Lys Trp Lys Ile Ile Val Lys Leu Asn Asp Gly
 1               5                  10

<210> SEQ ID NO 7
<211> LENGTH: 12
<212> TYPE: PRT
<213> ORGANISM: ARTIFICIAL
<220> FEATURE:
<223> OTHER INFORMATION: SYNTHETIC POLYPEPTIDE

<400> SEQUENCE: 7

Lys Ile Ile Val Lys Leu Asn Asp Gly Arg Glu Leu
 1               5                  10

<210> SEQ ID NO 8
<211> LENGTH: 12
<212> TYPE: PRT
<213> ORGANISM: ARTIFICIAL
<220> FEATURE:
<223> OTHER INFORMATION: SYNTHETIC POLYPEPTIDE
```

```
<400> SEQUENCE: 8

Val Lys Leu Asn Asp Gly Arg Glu Leu Ser Leu Asp
1               5                   10

<210> SEQ ID NO 9
<211> LENGTH: 12
<212> TYPE: PRT
<213> ORGANISM: ARTIFICIAL
<220> FEATURE:
<223> OTHER INFORMATION: SYNTHETIC POLYPEPTIDE

<400> SEQUENCE: 9

Gln Met Lys Leu Phe Lys Arg His Leu Lys Trp Lys
1               5                   10

<210> SEQ ID NO 10
<211> LENGTH: 12
<212> TYPE: PRT
<213> ORGANISM: ARTIFICIAL
<220> FEATURE:
<223> OTHER INFORMATION: SYNTHETIC POLYPEPTIDE

<400> SEQUENCE: 10

Met Lys Leu Phe Lys Arg His Leu Lys Trp Lys Ile
1               5                   10

<210> SEQ ID NO 11
<211> LENGTH: 14
<212> TYPE: PRT
<213> ORGANISM: ARTIFICIAL
<220> FEATURE:
<223> OTHER INFORMATION: SYNTHETIC POLYPEPTIDE

<400> SEQUENCE: 11

Met Lys Leu Phe Lys Arg His Leu Lys Trp Lys Ile Ile Val
1               5                   10

<210> SEQ ID NO 12
<211> LENGTH: 12
<212> TYPE: PRT
<213> ORGANISM: ARTIFICIAL
<220> FEATURE:
<223> OTHER INFORMATION: SYNTHETIC POLYPEPTIDE
<220> FEATURE:
<221> NAME/KEY: MISC_FEATURE
<222> LOCATION: (1)..(1)
<223> OTHER INFORMATION: natural or synthetic amino acid

<400> SEQUENCE: 12

Xaa Leu Phe Lys Arg His Leu Lys Trp Lys Ile Ile
1               5                   10

<210> SEQ ID NO 13
<211> LENGTH: 12
<212> TYPE: PRT
<213> ORGANISM: ARTIFICIAL
<220> FEATURE:
<223> OTHER INFORMATION: SYNTHETIC POLYPEPTIDE
<220> FEATURE:
<221> NAME/KEY: MISC_FEATURE
<222> LOCATION: (4)..(4)
<223> OTHER INFORMATION: natural or synthetic amino acid

<400> SEQUENCE: 13

Lys Leu Phe Xaa Arg His Leu Lys Trp Lys Ile Ile
1               5                   10
```

```
<210> SEQ ID NO 14
<211> LENGTH: 12
<212> TYPE: PRT
<213> ORGANISM: ARTIFICIAL
<220> FEATURE:
<223> OTHER INFORMATION: SYNTHETIC POLYPEPTIDE
<220> FEATURE:
<221> NAME/KEY: MISC_FEATURE
<222> LOCATION: (8)..(8)
<223> OTHER INFORMATION: natural or synthetic amino acid

<400> SEQUENCE: 14

Lys Leu Phe Lys Arg His Leu Xaa Trp Lys Ile Ile
1               5                   10

<210> SEQ ID NO 15
<211> LENGTH: 12
<212> TYPE: PRT
<213> ORGANISM: ARTIFICIAL
<220> FEATURE:
<223> OTHER INFORMATION: SYNTHETIC POLYPEPTIDE
<220> FEATURE:
<221> NAME/KEY: MISC_FEATURE
<222> LOCATION: (10)..(10)
<223> OTHER INFORMATION: natural or synthetic amino acid

<400> SEQUENCE: 15

Lys Leu Phe Lys Arg His Leu Lys Trp Xaa Ile Ile
1               5                   10

<210> SEQ ID NO 16
<211> LENGTH: 12
<212> TYPE: PRT
<213> ORGANISM: ARTIFICIAL
<220> FEATURE:
<223> OTHER INFORMATION: SYNTHETIC POLYPEPTIDE

<400> SEQUENCE: 16

Lys Leu Phe Lys Lys His Leu Lys Trp Lys Ile Ile
1               5                   10

<210> SEQ ID NO 17
<211> LENGTH: 12
<212> TYPE: PRT
<213> ORGANISM: ARTIFICIAL
<220> FEATURE:
<223> OTHER INFORMATION: SYNTHETIC POLYPEPTIDE
<220> FEATURE:
<221> NAME/KEY: MISC_FEATURE
<222> LOCATION: (5)..(5)
<223> OTHER INFORMATION: natural or synthetic amino acid

<400> SEQUENCE: 17

Lys Leu Phe Lys Xaa His Leu Lys Trp Lys Ile Ile
1               5                   10

<210> SEQ ID NO 18
<211> LENGTH: 33
<212> TYPE: PRT
<213> ORGANISM: ARTIFICIAL
<220> FEATURE:
<223> OTHER INFORMATION: SYNTHETIC POLYPEPTIDE

<400> SEQUENCE: 18

Ser Ile Gln Lys Leu Asn Val Ser Met Lys Leu Phe Arg Lys Gln Ala
1               5                   10                  15

Lys Trp Lys Ile Ile Val Lys Leu Asn Asp Gly Arg Glu Leu Ser Leu
            20                  25                  30
```

-continued

Asp

<210> SEQ ID NO 19
<211> LENGTH: 33
<212> TYPE: PRT
<213> ORGANISM: ARTIFICIAL
<220> FEATURE:
<223> OTHER INFORMATION: SYNTHETIC POLYPEPTIDE

<400> SEQUENCE: 19

```
Ala Asn Ile Lys Leu Ser Val Gln Met Lys Leu Phe Lys Arg His Leu
1               5                   10                  15

Lys Trp Lys Ile Ile Val Lys Leu Asn Asp Gly Arg Glu Leu Ser Leu
            20                  25                  30

Asp
```

<210> SEQ ID NO 20
<211> LENGTH: 11
<212> TYPE: PRT
<213> ORGANISM: ARTIFICIAL
<220> FEATURE:
<223> OTHER INFORMATION: SYNTHETIC POLYPEPTIDE

<400> SEQUENCE: 20

```
Lys Leu Lys Leu Leu Leu Leu Leu Lys Leu Lys
1               5                   10
```

POLYPEPTIDES WITH THERAPEUTIC ACTIVITY AND METHODS OF USE

CROSS-REFERENCE TO RELATED APPLICATIONS

The present application claims priority to Provisional Patent Application Ser. Nos. 60/177,255, filed on Jan. 20, 2000 and 60/210,297, filed Jun. 8, 2000, both of which are incorporated herein by reference.

BACKGROUND

A series of designed peptide 33mers (βpep peptides) has been reported to be bactericidal and to be capable of neutralizing the bacterial endotoxin lipopolysaccharide (LPS) (Mayo et al., *Biochim. Biophys. Acta* 1425, 81–92 (1998)). CD and NMR conformational analyses indicate that βpep peptides form β-sheets (Mayo et al., *Protein Sci.* 5, 1301–1315 (1996)), and one of these, βpep-4, folds compactly as anti-parallel β-sheet sandwich (Ilyina et al., *Biochemistry* 36, 5245–5250 (1997)). βpep-19 is potently bactericidal in the $10^{-8}$ M range (Mayo et al., *Biochim. Biophys. Acta* 1425, 81–92 (1998)). βpep peptides function like Limulus anti-LPS factor (LALF) and the homologous bactericidal/permeability increasing protein (B/PI) (Hoess et al., *EMBO J.* 12, 3351–3356 (1993)) in that all appear to express activity through an amphipathic β-sheet structural motif having a cationic β-sheet face (Kelly et al., *Surgery* 114, 140–146 (1993); Siefferman et al., *Infect. Immun.* 59, 2152–2157 (1991); Beamer et al., *Science* 276, 1861–1864 (1997); and Gray et al., *Biochim. Biophys. Acta* 1244, 185–190 (1995)).

Numerous studies on bactericidal peptides indicate the functional importance of a net positive charge and high hydrophobicity in the context of an amphipathic, usually helical, structure (Maloy et al., *Biopolymers* 37, 105–122 (1995)). The net positive charge promotes interaction with the negatively charged surface of bacterial membranes (Matsuzaki et al., *Biochemistry* 36, 2104–2111(1997)), whereas structure-activity relationships demonstrate that the amphipathic conformation of the peptide promotes bacterial cell lysis (Andreu et al., *Biochemistry* 24, 1683–1688 (1985)). Bactericidal peptides such as cecropins (Lee et al., *Proc. Natl. Acad. Sci. USA* 86, 9159–9162 (1989)), magainins (Zasloff, *Proc. Natl. Acad. Sci. USA*, 84, 5449–5453 (1987)), proline-arginine-rich peptides (Agerberth et al., *Eur. J. Biochem.* 202, 849–854 (1991)), and sapecin (Matsuyama et al., *J. Biol. Chem.* 263, 17112–17116 (1988)), like βpep peptides, all have a net positive charge and considerable hydrophobic character. The cecropins and magainins are helix-forming peptides (Holak et al., *Biochemistry* 27, 7620–7629 (1988); and Marion et al., *FEBs Lett.* 227, 21–26 (1988)), whereas the sapacins contain both α-helix and β-sheet segments (Hanzawa et al., *FEBs Lett.* 269, 413–420 (1990)). Structures for the proline-arginine-rich peptides are unknown. Tachyplesin, a bactericidal and endotoxin neutralizing peptide isolated from hemocytes of the horseshoe crab (Kawano et al., *J. Bio. Chem.* 265, 15365–15367 (1990)), as well as anti-bacterial peptide defensins (Selsted et al., *J Biol. Chem.* 264, 4003–4007 (1989); and Lebrer et al., *Cell* 64, 229–230 (1991)), form dimeric β-sheets which are stabilized by three intramolecular disulfide bridges (Hill et al., *Science* 251, 1481–1485 (1991)). In addition, a number of small, antibiotic peptides based on the structure of the anti-LPS, cyclic peptide polymyxin B (Morrison et al., *Immunochem.* 13, 813–818 (1976)) have been designed as short β-hairpins constrained by a disulfide bridge (Rustici et al., *Science* 259, 361–365 (1993)).

SUMMARY OF THE INVENTION

The present invention provides a polypeptide selected from the group consisting of: ANIKLSVQMKLF (SEQ ID NO:1); KLSVQMKLFKRH (SEQ ID NO:2); VQMKLFKRHLKW (SEQ ID NO:3); KLFKRHLKWKII (SEQ ID NO:4); KRHLKWKIIVKL (SEQ ID NO:5); LKWKIIVKLNDG (SEQ ID NO:6); KIIVKLNDGREL (SEQ ID NO:7); VKLNDGRELSLD (SEQ ID NO:8); QMKLFKRHLKWK (SEQ ID NO:9); MKLFKRHLKWKI (SEQ ID NO:10); MKLFKRHLKWKIIV (SEQ ID NO:11); XLFKRHLKWKII (SEQ ID NO:12); KLFXRHLKWKII (SEQ ID NO:13); KLFKRHLXWKII (SEQ ID NO:14); KLFKRHLKWXII (SEQ ID NO:15); KLFKKHLKWKII (SEQ ID NO:16); KLFKXHLKWKII (SEQ ID NO:17); analogs thereof (preferably that are active for the treatment of bacterial infection and/or endotoxemia); and combinations thereof; wherein X is an amino acid.

The present invention also provides a method for treating bacterial infection and/or endotoxemia. This includes administering to a patient an amount of a pharmaceutical composition effective to inhibit the bacterial infection and/or neutralize endotoxin, wherein the pharmaceutical composition includes a polypeptide (i.e., one or more polypeptide) listed above. A method for inhibiting bacterial infection and/or endotoxemia in vitro is also provided. The method includes contacting cells with an amount of a composition effective to inhibit the bacterial infection and/or to neutralize endotoxin, wherein the composition includes a polypeptide listed above.

The present invention also provides a method for decreasing the amount of TNF-α in a patient. The method includes administering to the patient a therapeutically effective amount of a pharmaceutical composition including a polypeptide listed above. A method for decreasing the amount of TNF-α in vitro is also provided. The method includes incubating cells with an effective amount of a composition comprising a polypeptide selected listed above. Other polypeptides suitable for these methods include analogs of those listed above that are active for decreasing the amount of TNF-α.

The present invention also provides a method for inhibiting endothelial cell proliferation in a patient. The method involves administering to the patient a therapeutically effective amount of a composition including a polypeptide listed above. A method for inhibiting endothelial cell proliferation in vitro is also provided. The method involves contracting cells with an effective amount of a composition including a polypeptide listed above. Other polypeptides suitable for these methods include analogs of those listed above that are active for inhibiting endothelial cell proliferation.

The present invention also provides a method for inhibiting angiogenic-factor mediated inter-cellular adhesion molecule expression down-regulation in a patient. The method includes administering to the patient a therapeutically effective amount of a composition including a polypeptide listed above. A method for inhibiting angiogenic-factor mediated inter-cellular adhesion molecule expression down-regulation in vitro is also provided. The method includes contacting cells with an effective amount of a composition including a polypeptide listed above. Other polypeptides suitable for these methods include analogs of those listed above that are active for inhibiting antigenic-factor mediated inter-cellular adhesion molecule expression down-regulation.

The present invention also provides a method for inhibiting angiogenesis in a patient. The method includes administering to the patient a therapeutically effective amount of a composition including a polypeptide listed above. A method for inhibiting angiogenesis in vitro is also provided. The method includes contacting cells with an effective amount of a composition including a polypeptide listed above. Other polypeptides suitable for these methods include analogs of those listed above that are active for inhibiting angiogenesis.

The present invention also provides a method for inhibiting tumorigenesis in a patient. The method includes administering to the patient a therapeutically effective amount of a composition including a polypeptide listed above. Other polypeptides suitable for this method includes analogs of those listed above that are active for inhibiting tumorigenesis.

The present invention also provides the three-dimensional structure of certain of the polypeptides using nuclear magnetic resonance (NMR) spectroscopy (e.g., one- and two-dimensional NMR) and circular dichroism (CD) spectroscopy. This information is of significant utility in fields such as drug discovery. Thus, the present invention also provides methods of using such structural information.

The present invention provides a polypeptide having an amphipathic structure having one surface with positively charged amino acid residues and an opposing surface with hydrophobic amino acid residues, wherein these define a surface active domain. Preferably, the surface active domain includes amino acids K1, K4, K8, and R5 shown in FIG. 6B, and more preferably, atoms 1–24, 64–109, and 146–167 listed in Table 5. More preferably, the polypeptide has the structure coordinates listed in Table 5 and most preferably has the sequence KLFKRHLKWKII (SEQ ID NO:4).

One specific method of the present invention involves evaluating a candidate compound for structural similarity to that of KLFKRHLKWKII (SEQ ID NO:4) by: supplying a three-dimensional structure of KLFKRHLKWKII (SEQ ID NO:4) or a portion thereof; supplying a three-dimensional structure of a candidate compound; and comparing the three-dimensional structure of the candidate compound with the three-dimensional structure of KLFKRHLKWKII (SEQ ID NO:4) or a portion thereof.

As used herein, "a" or "an" refers to one or more of the term modified. Thus, the compositions of the present invention include one or more polypeptides.

"Amino acid" is used herein to refer to a chemical compound with the general formula: $NH_2$—CRH—COOH, where R, the side chain, is H or an organic group. Where R is an organic group, R can vary and is either polar or nonpolar (i.e., hydrophobic). The amino acids of this invention can be naturally occurring or synthetic (often referred to as nonproteinogenic). As used herein, an organic group is a hydrocarbon group that is classified as an aliphatic group, a cyclic group or combination of aliphatic and cyclic groups. The term "aliphatic group" means a saturated or unsaturated linear or branched hydrocarbon group. This term is used to encompass alkyl, alkenyl, and alkynyl groups, for example. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" refers to mono- or polycyclic aromatic hydrocarbon groups. As used herein, an organic group can be substituted or unsubstituted.

The terms "polypeptide" and "peptide" as used herein, are used interchangeably and refer to a polymer of amino acids. These terms do not connote a specific length of a polymer of amino acids. Thus, for example, the terms oligopeptide, protein, and enzyme are included within the definition of polypeptide or peptide, whether produced using recombinant techniques, chemical or enzymatic synthesis, or naturally occurring. This term also includes polypeptides that have been modified or derivatized, such as by glycosylation, acetylation, phosphorylation, and the like.

The following abbreviations are used throughout the application:

| | |
|---|---|
| A = Ala = Alanine | T = Thr = Threonine |
| V = Val = Valine | C = Cys = Cysteine |
| L = Leu = Leucine | Y = Tyr = Tyrosine |
| I = Ile = Isoleucine | N = Asn = Asparagine |
| P = Pro = Proline | Q = Gln = Glutamine |
| F = Phe = Phenylalanine | D = Asp = Aspartic Acid |
| W = Trp = Tryptophan | E = Glu = Glutamic Acid |
| M = Met = Methionine | K = Lys = Lysine |
| G = Gly = Glycine | R = Arg = Arginine |
| S = Ser = Serine | H = His = Histidine |

Other abbreviations used throughout include: B/PI, bactericidal/permeability increasing protein; LALF, Limulus anti-lipopolysaccharide factor; LPS, lipopolysaccharide; PF4, platelet factor 4; NMR, nuclear magnetic resonance spectroscopy; NOE, nuclear Overhauser effect; rf, radio frequency; FID, free induction decay; CD, circular dichroism; HPLC, high performance liquid chromatography; PBS, phosphate buffered saline; FCS, fetal calf serum.

BRIEF DESCRIPTION OF THE DRAWINGS

FIG. 1. Peptide sequences: peptide sequences are shown for βpep-19 (SEQ ID NO: 18) and βpep-25 (SEQ ID NO: 19), along with those of eight dodecapeptides which "walk through" the sequence of βpep-25. The dodecapeptides are referred to as SC peptides. The —NH₂ at the right of each sequence indicates amidation of the C-terminal carboxylate group.

FIG. 4C shows the change in $(\Theta)222$ versus the concentration of trifluoroethanol (TFE).

DETAILED DESCRIPTION OF PREFERRED EMBODIMENTS

Figure 2A:
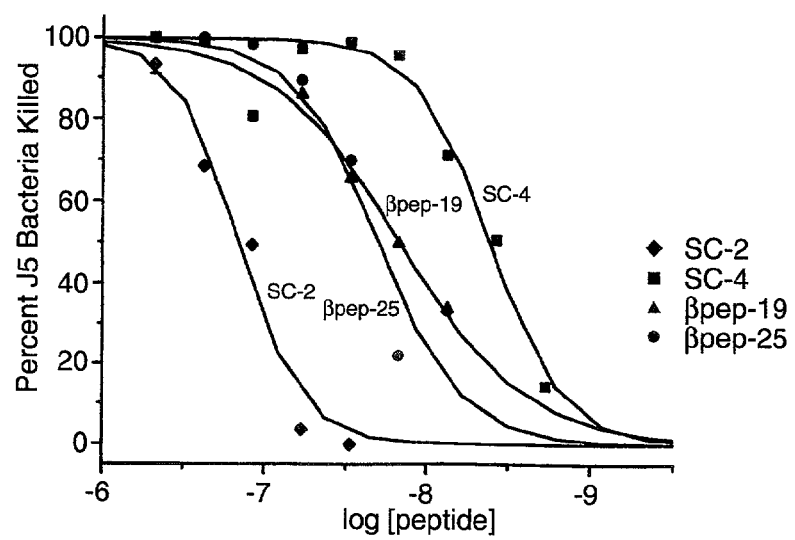
FIGS. 2A through 2C. Bactericidal Dose Response Curves for Peptides. A select number of dose response curves are shown in these figures as percent bacteria killed versus the log concentration of peptide. Data are provided for three strains of bacteria: (2A) rough strain E. coli J5; (2B) smooth strain E. coli IA2; and (2C) a strain of Gram-positive S. aureus MNHO. Dose response curves were acquired as described in the Methods Section.

This invention contributes to the development of agents in combating the ever-recurring problem of drug-resistant microorganisms. It involves the discovery of polypeptides effective in the treatment of bacterial infection and/or bacterial endotoxemia, as well as other disorders.

The compositions comprising the polypeptides of this invention can be added to cells in culture or used to treat patients, such as mammals. Where the polypeptides are used to treat a patient, the polypeptide is preferably combined in a pharmaceutical composition with a pharmaceutically acceptable carrier such as a larger molecule to promote polypeptide stability or a pharmaceutically acceptable buffer that serves as a carrier for the polypeptide.

Treatment can be prophylactic or therapeutic. Thus, treatment can be initiated before, during, or after the development of the condition (e.g., bacterial infection or endotoxemia). As such, the phrases "inhibition of" or "effective to inhibit" a condition such as bacterial infection and/or endotoxemia, for example, includes both prophylactic and therapeutic treatment (i.e., prevention and/or reversal of the condition).

The present invention provides a method for treating bacterial infection and/or endotoxemia in a patient (e.g., a mammal such as a human). This involves administering to a patient an amount of a pharmaceutical composition effective to inhibit the bacterial infection and/or to neutralize endotoxin, wherein the pharmaceutical composition includes one or more polypeptides described herein. Analogously, the present invention provides a method for inhibiting bacterial infection and/or endotoxemia in vitro (e.g., in a cell culture). This method involves contacting cells with an amount of a composition effective to inhibit the bacterial infection and/or to neutralize endotoxin, wherein the composition includes one or more polypeptides described herein.

More than 100 years ago, it was determined that heat stable extracts of gram-negative enteric bacteria were highly toxic. Assuming that these toxins were released from the interior of the bacterium upon its death, the investigators termed these toxins "endotoxins." Subsequent chemical studies showed that these endotoxins are actually lipopolysaccharide (LPS) components of the outer membrane of enteric bacteria. Toxic LPS is composed of three structural units—an outer polysaccharide component, a core oligosaccharide region, and the inner portion, lipid A, which affords the molecule its proinflammatory activities. Toxic LPS is released from the bacterium when it dies or during periods of rapid bacterial growth.

In many species, for instance humans, cows, rabbits, mice, and rats, toxic LPS in serum binds rapidly to a plasma polypeptide named lipopolysaccharide binding protein (LBP). LBP, which is synthesized by hepatocytes as part of the acute phase response of inflammation, has a strong affinity for the lipid A portion of endotoxin.

Activation of a cell by a toxic LPS-containing complex results in the synthesis, release, or activation of cell-derived proinflammatory mediators, which can include cytokines (e.g., interleukin-1, interleukin-6, interleukin-8, and tumor necrosis factor-α), platelet activating factor, nitric oxide, complement (e.g., C5a and C3a), prostagladins, leukotrienes, the kinin system, oxygen metabolites, catecholamines and endorphines. The mediators can impact organ systems including the heart, vascular system, coagulation system, lungs, liver, kidney and the central nervous system. These factors can lead to endotoxemia, also referred to as endotoxic shock, septic shock, circulatory shock, and septicemia, a progressive disease that can lead to death.

Endotoxemia is typically caused by toxic LPS from Gram-negative bacteria, but can also be caused by Gram-positive bacteria, and occasionally, by fungi. Components released by Gram-positive bacteria that can cause endotoxemia include peptidoglycan and lipoteichoic acid, and lipoarabinomannan from the cell wall of *Mycobacterium* spp.

Studies have shown that serum concentrations of the cytokine tumor necrosis factor (TNF) increase after onset of endotoxemia, and serum TNF activity is directly associated with the onset of signs of abdominal pain and fever, for example. Thus, endotoxin activity can also be measured by determining the amount of release of tumor necrosis factor alpha (TNF-α) from a macrophage cell line or by evaluating the symptoms of shock in animals. Production of TNF-α can be assayed as described by Mosmann (*J. Immunological Methods* 65:55–63 1983).

In both the in vivo and in vitro methods, "inhibiting" a bacterial infection includes preventing as well as reversing or reducing the growth of bacteria in a patient or a cellular sample, and "neutralizing" endotoxin includes binding LPS and thereby removing it from the system of a patient or a cellular sample. The level of bacterial infection can be determined according to the bactericidal assay described in the Examples Section. The level of endotoxemia can be determined according to the LPS neutralization assay described in the Examples Section. These assays can be used to determine the effectiveness of a polypeptide, whether used in vivo or in vitro. To determine the effectiveness of the treatment of a patient having a bacterial infection, a blood sample can be taken, a culture developed, and the amount of live bacteria determined according to the bactericidal assay described in the Examples Section. To determine the effectiveness of the treatment of a patient having endotoxemia, a blood sample can be taken, a culture developed, and the amount of cytokines (e.g., TNF-α, IL-1) can be determined using methods known to one of skill in the art. For example, the WEHI assay can be used for the detection of TNF-α (Battafarano et al., *Surgery* 118, 318–324 (1995)).

The effective amount of a peptide for treating a bacterial infection will depend on the bacterial infection, the location of the infection and the peptide. An effective amount of the peptide for treating bacterial infection is that amount that diminishes the number of bacteria in the animal and that diminishes the symptoms associated with bacterial infection such as fever, pain and other associated symptoms of the bacterial infection. The effective amount of a peptide can be determined by standard dose response methods in vitro and an amount of peptide that is effective to kill at least about 50% to about 100% of the bacteria ($LD_{50}$) and more preferably about 60% to about 100% of the bacteria would be considered an effective amount. Preferably, the peptide has an effective dose at a concentration of about $1\times10^{-4}$ M to about $1\times10^{-10}$M, and more preferably at a concentration of about $1\times10^{-7}$ M to about $1\times10^{-9}$ M. Peptides that are considered to be bactericidal kill at least one organism selected from the group of *P. aeruginosa, P. cepacia, E. coli* B, *Salmonella, Proteus mirabilis*, and *Staphylococcus aureus* at concentrations of about $10^{-10}$ M or greater under physiological conditions (e.g., at a pH of 5.6).

Alternatively, an effective amount of the peptide for treating a bacterial infection can be determined in an animal system such as a mouse. Acute peritonitis can be induced in mice such as outbred Swiss webster mice by intraperitoneal injection with bacteria such as *P. aeruginosa* as described by Dunn et al. (*Surgery*, 98:283–290 1985; Cody et al. (*J. Int. Surg. Res.*, 52:314–319 1992). Different amounts of peptide can be injected at one hour intravenously prior to the injection of the bacteria. The percentage of viable bacteria in blood, spleen, and liver can be determined in the presence and absence of the peptide or other antibiotics. While not meant to limit the invention, it is believed that bactericidal peptide could also enhance the effectiveness of other antibiotics such as erythromycin, and the like.

Bactericidal activity can be evaluated against a variety of bacteria, preferably Gram-negative bacteria, but the types of bacteria can include *Pseudomonas* spp including *P. aeruginosa* and *P. cepacia, E. coli* strains, including *E. coli* B, *Salmonella, Proteus mirabilis* and *Staphylococcus* strains such as *Staphylococcus aureus*. A preferred organism is *Pseudomonas aeruginosa*.

Peptides with endotoxin neutralizing activity can be used to treat mammals infected with Gram-negative bacteria systemically and that exhibit symptoms of endotoxin shock such as fever, shock, and TNF-α release. The animals are typically infected with one or more Gram-negative bacteria such as *Pseudomonas* spp., rough strains of *E. coli*, encapsulated *E. coli* and smooth strain *E. coli*. The endotoxin neutralizing peptide can be combined with other agents that are known and used to treat endotoxin shock.

Endotoxin neutralizing activity can be measure by determining the molar concentration at which the peptide completely inhibits the action of lipopolysaccharide in an assay such as the Limulus amoebocyte lysate assay (LAL, Sigma Chemicals, St. Louis, Mo.) or the chromogenic LAL 1000 test (Biowhittacker, Walkersville, Md.). Endotoxin neutralizing activity can also be measured by calculating an inhibitory dose 50 ($LD_{50}$) using standard dose response methods. An inhibitory dose 50 is that amount of peptide that can inhibit 50% of the activity of endotoxin. Peptides preferably neutralized endotoxin at a molar concentration of about $1\times10^{-4}$ M to about $10^{-8}$ M, more preferably about $10^{-5}$ M to about $10^{-6}$ M. Peptides considered to not have endotoxin neutralizing activity do not neutralize endotoxin at a molar concentration of about $10^{-4}$ M or less.

The present invention also provides a method for decreasing the amount of TNF-α in a patient (e.g., a mammal such as a human). This involves administering to a patient an amount of a pharmaceutical composition effective to decrease the amount of TNF-α in a patient's system as determined by evaluating serum levels of TNF-α, wherein the pharmaceutical composition includes one or more polypeptides described herein. Analogously, the present invention provides a method for decreasing the amount of TNF-α in vitro (e.g., in a cell culture). This method involves incubating cells with an amount of a composition effective to decrease TNF-α amounts in the cell culture, wherein the composition includes one or more polypeptides described herein. For both in vivo and in vitro methods, the WEHI assay can be used for the detection of TNF-α (Battafarano et al., *Surgery* 118, 318–324 (1995)) in cell culture or in serum from a patient. Alternatively, the amount of TNF-α in a sample can be assayed using an anti-TNF-α antibody. A polypeptide "active" for decreasing TNF-α can be evaluated using an in vitro test, and preferably shows an at least 10% decrease in the amount of TNF-α.

Angiogenesis is crucial to numerous biological functions in the body, from normal processes like embryogenesis and wound healing to abnormal processes like tumor growth, arthritis, restenosis and diabetic retinopathy. The use of agents that can inhibit angiogenesis in vitro and in vivo, particularly in anti-tumor research, has indicated that anti-angiogenic therapy will be a promising therapeutic modality in the future. The search for angiogenic inhibitors has been focused on controlling two of the processes that promote angiogenesis: endothelial cell (EC) growth and adhesion primarily because ECs are more accessible than are other cells to pharmacologic agents delivered via the blood and ECs are genetically stable and are not easily mutated into drug resistant variants. Most anti-angiogenic agents have been discovered by identifying endogenous molecules, primarily proteins, which inhibit EC growth. This traditional approach has produced a number of anti-angiogenics, such as platelet factor-4 (PF4), thrombospondin, tumor necrosis factor (TNF), interferon-γ inducible protein-10, angiostatin, endostatin, vasostatin, and bactericidal-permeability increasing (BPI) protein. In toto, about forty anti-angiogenic agents, identified using various approaches, are currently known.

It has also been postulated that tumor growth can be controlled by deprivation of vascularization (Folkman J. *natl. Cancer. Inst.* 82, 4–6 (1990); Folkman et al., *J. biol. Chem.* 267, 10931–10934 (1992)). A growing number of endogenous inhibitors of angiogenesis such as platelet factor-4 (PF4), interferon-γ inducible protein-10 (IP-10), thrombospondin-1 (TSP-1), angiostatin, as well as synthetic agents, e.g., thalidomide, TNP-470, and metalloproteinase inhibitors have been described. Some of these agents are currently being tested in phase I/II clinical trials. Previous research described in Griffioen et al., *Blood* 88, 667–673 (1996), and Griffioen et al., *Cancer Res.* 56, 1111–1117 (1996) has shown that pro-angiogenic factors in tumors induce down-regulation of adhesion molecules on endothelial cells in the tumor vasculature and induce anergy to inflammatory signals such as tumor necrosis factor α (TNFα), interleukin-1, and interferon-γ. EC exposed to vascular endothelial cell growth factor (VEGF) (Griffioen et al., *Blood* 88, 667–673 (1996)) and basic fibroblast growth factor (bFGF) (Griffioen et al., *Blood* 88, 667–673 (1996); and Melder et al., *Nature Med.* 2, 992–997 (1996)) have a severely hampered up-regulation of intercellular adhesion molecule-1 (ICAM-1) and induction of vascular cell adhesion molecule-1 (VCAM-1) and E-selectin. This phenomenon, which was named tumor-induced EC anergy, is one way in which tumors with an angiogenic phenotype may escape infiltration by cytotoxic leukocytes.

Because angiogenesis-mediated down-regulation of endothelial adhesion molecules (EAM) may promote tumor outgrowh by avoiding the immune response (Griffioen et al., *Blood* 88, 667–673 (1996); Kitayama et al., *Cancer. Res.* 54 4729–4733 (1994); and Piali et al., *J. exp. Med.* 181, 811–816 (1995)), it is believed that inhibition of angiogenesis would overcome the down-regulation of adhesion molecules and the unresponsiveness to inflammatory signals. In support of this hypothesis, a relation between E-selectin up-regulation and the angiostatic agent AGM-1470 has been reported (Budson et al., *Biochem. Biophys. Res. Comm.* 225, 141–145 (1996)). It has also been shown that inhibition of angiogenesis by PF4 up-regulates ICAM-1 on bFGF-simulated EC. In addition, inhibition of angio-genesis by PF4 overcomes the angiogenesis-associated EC anergy to inflammatory signals.

Thus, the present invention provides a method for inhibiting endothelial cell proliferation in a patient (e.g., a mammal such as a human). This involves administering to a patient an amount of a pharmaceutical composition effective to inhibit the growth or endothelial cells, wherein the pharmaceutical composition includes one or more polypeptides described herein. Analogously, the present invention provides a method for inhibiting endothelial cell proliferation in vitro (e.g., in a cell culture). This method involves contacting cells with an amount of a composition effective to prevent and/or reduce the growth of endothelial cells, wherein the composition includes one or more polypeptides described herein.

For determining the amount of endothelial cell proliferation in vivo, various methods known to one of skill in the art could be used. For example, for evaluation of endothelial cell growth in tumors, tissue sections can be appropriately stained to quantify vessel density. For determining the amount of endothelial cell proliferation in vitro, the EC Proliferation Assay described in the Examples Section can be used, which involves the uptake of tritiated thymidine by cells in cell culture. A polypeptide that is "active" for inhibiting endothelial cell proliferation is preferably one that causes an at least 10% reduction in endothelial cell proliferation at a concentration lower than $10^{-4}$ M.

The present invention also provides a method for inhibiting angiogenic-factor mediated inter-cellular adhesion molecule expression down-regulation in a patient (e.g., a mammal such as a human). This involves administering to a patient an amount of a pharmaceutical composition effective to prevent and/or reduce the amount of ICAM expression down-regulation, wherein the pharmaceutical composition includes one or more polypeptides described herein. Analogously, the present invention provides a method for inhibiting angiogenic-factor mediated inter-cellular adhesion molecule expression down-regulation in vitro (e.g., in a cell culture). This method involves contacting cells with an amount of a composition effective to prevent and/or reduce the amount of ICAM expression down-regulation, wherein the composition includes one or more polypeptides described herein.

The present invention provides a method for inhibiting angiogenesis (i.e., new blood vessel formation) in a patient (e.g., a mammal such as a human). This involves administering to a patient an amount of a pharmaceutical composition effective to prevent and/or reduce angiogenesis, wherein the pharmaceutical composition includes one or more polypeptides described herein. Analogously, the present invention provides a method for inhibiting angiogenesis in vitro (e.g., in a cell culture). This method involves contacting cells with an amount of a composition effective to prevent and/or reduce angiogenesis, wherein the composition includes one or more polypeptides described herein.

For determining the amount of angiogenesis in vivo, various methods known to one of skill in the art could be used. For example, for evaluation of angiogenesis in tumors, tissue sections can be appropriately stained to quantify vessel density. For determining the amount of angiogenesis in vitro, the In vitro Angiogenesis Assay (i.e., EC Tube Formation Assay) described in the Examples Section can be used, which involves the disappearance of EC sprouting in cell culture. A polypeptide that is "active" for angiogenesis inhibition is preferably one that causes an at least 10% reduction in endothelial cell sprouting at a concentration lower than $10^{-4}$ M.

The present invention provides a method for inhibiting tumorigenesis in a patient (e.g., a mammal such as a human). This involves administering to a patient an amount of a pharmaceutical composition effective to prevent and/or reduce tumor growth, wherein the pharmaceutical composition includes one or more polypeptides described herein. Methods of determining the inhibition of tumorigenesis are well known to those of skill in the art, including evaluation of tumor shrinkage, survival, etc.

A preferred polypeptide is selected from the group consisting of: ANIKLSVQMKLF (SEQ ID NO:1); KLSVQMKLFKRH (SEQ ID NO:2); VQMKLFKRHLKW (SEQ ID NO:3); KLFKRHLKWKII (SEQ ID NO:4); KRHLKWKIIVKL (SEQ ID NO:5); LKWKIIVKLNDG (SEQ ID NO:6); KIIVKLNDGREL (SEQ ID NO:7); VKLNDGRELSLD (SEQ ID NO:8); and analogs thereof.

An alternative polypeptide is selected from the group consisting of: QMKLFKRHLKWK (SEQ ID NO:9); MKLFKRHLKWKI (SEQ ID NO:10); MKLFKRHLKWKIIV (SEQ ID NO:11); XLFKRHLKWKII (SEQ ID NO:12); KLFXRHLKWKII (SEQ ID NO:13); KLFKRHLXWKII (SEQ ID NO:14); KLFKRHLKWXII (SEQ ID NO: 15); KLFKKHLKWKII (SEQ ID NO: 16); KLFKXHLKWKII (SEQ ID NO: 17); and analogs thereof; wherein X is an amino acid, natural or synthetic. Preferably, X is norleucine.

A more preferred polypeptide is selected from the group consisting of: ANIKLSVQMKLF (SEQ ID NO:1); KLSVQMKLFKRH (SEQ ID NO:2); VQMKLFKRHLKW (SEQ ID NO:3); KLFKRHLKWKII (SEQ ID NO:4); KRHLKWKIIVKL (SEQ ID NO:5); LKWKIIVKLNDG (SEQ ID NO:6); KIIVKLNDGREL (SEQ ID NO:7); and VKLNDGRELSLD (SEQ ID NO:8).

The polypeptides of SEQ ID NOs:1–17 can be in their free acid form or they can be amidated at the C-terminal carboxylate group. The present invention also includes analogs of the polypeptide of SEQ ID NOs:1–17, which typically have structural similarity with SEQ ID NOs:1–17. An "analog" of a polypeptide includes at least a portion of the polypeptide, wherein the portion contains deletions or additions of one or more contiguous or noncontiguous amino acids, or containing one or more amino acid substitutions. Substitutes for an amino acid in the polypeptides of the invention are preferably conservative substitutions, which are selected from other members of the class to which the amino acid belongs. For example, it is well-known in the art of protein biochemistry that an amino acid belonging to a grouping of amino acids having a particular size or characteristic (such as charge, hydrophobicity and hydrophilicity)

can generally be substituted for another amino acid without substantially altering the structure of a polypeptide.

For the purposes of this invention, conservative amino acid substitutions are defined to result from exchange of amino acids residues from within one of the following classes of residues: Class I: Ala, Gly, Ser, Thr, and Pro (representing small aliphatic side chains and hydroxyl group side chains); Class II: Cys, Ser, Thr, and Tyr (representing side chains including an —OH or —SH group); Class III: Glu, Asp, Asn, and Gln (carboxyl group containing side chains): Class IV: His, Arg, and Lys (representing basic side chains); Class V: Ile, Val, Leu, Phe, and Met (representing hydrophobic side chains); and Class VI: Phe, Trp, Tyr, and His (representing aromatic side chains). The classes also include related amino acids such as 3Hyp and 4Hyp in Class I; homocysteine in Class II; 2-aminoadipic acid, 2-aminopimelic acid, γ-carboxyglutamic acid, β-carboxyaspartic acid, and the corresponding amino acid amides in Class III; ornithine, homoarginine, N-methyl lysine, dimethyl lysine, trimethyl lysine, 2,3-diaminopropionic acid, 2,4-diaminobutyric acid, homoarginine, sarcosine and hydroxylysine in Class IV; substituted phenylalanines, norleucine, norvaline, 2-aminooctanoic acid, 2-aminoheptanoic acid, statine and β-valine in Class V; and naphthylalanines, substituted phenylalanines, tetrahydroisoquinoline-3-carboxylic acid, and halogenated tyrosines in Class VI.

Polypeptide analogs, as that term is used herein, also include modified polypeptides. Modifications of polypeptides of the invention include chemical and/or enzymatic derivatizations at one or more constituent amino acid, including side chain modifications, backbone modifications, and N- and C-terminal modifications including acetylation, hydroxylation, methylation, amidation, and the attachment of carbohydrate or lipid moieties, cofactors, and the like.

A preferred polypeptide analog is characterized by having at least one of the biological activities described herein. Such an analog is referred to herein as a "biologically active analog" or simply "active analog." The biological activity of a polypeptide can be determined, for example, as described in the Examples Section.

The polypeptides of the invention may be synthesized by the solid phase method using standard methods based on either t-butyloxycarbonyl (BOC) or 9-fluorenylmethoxycarbonyl (FMOC) protecting groups. This methodology is described by G. B. Fields et al. in *Synthetic Peptides: A User's Guide*, W.M. Freeman & Company, New York, N.Y., pp. 77–183 (1992). The present peptides may also be synthesized via recombinant techniques well known to those skilled in the art. For example, U.S. Pat. No. 5,595,887 describes methods of forming a variety of relatively small peptides through expression of a recombinant gene construct coding for a fusion protein which includes a binding protein and one or more copies of the desired target peptide. After expression, the fusion protein is isolated and cleaved using chemical and/or enzymatic methods to produce the desired target peptide.

The polypeptides of this invention can be administered alone in a pharmaceutically acceptable carrier, as an antigen in association with another protein, such as an immunostimulatory protein or with a protein carrier such as, but not limited to, keyhole limpet hemocyanin (KLH), bovine serum albumin (BSA), ovalbumin, or the like. They may be employed in a monovalent state (i.e., free peptide or a single peptide fragment coupled to a carrier molecule). They may also be employed as conjugates having more than one (same or different) peptides bound to a single carrier molecule. The carrier may be a biological carrier molecule (e.g., a glycosaminoglycan, a proteoglycan, albumin or the like) or a synthetic polymer (e.g., a polyalkyleneglycol or a synthetic chromatography support). Typically, ovalbumin, human serum albumin, other proteins, polyethylene glycol, or the like are employed as the carrier. Such modifications may increase the apparent affinity and/or change the stability of a peptide. The number of peptides associated with or bound to each carrier can vary, but from about 4 to 8 peptides per carrier molecule are typically obtained under standard coupling conditions.

The polypeptides can be conjugated to other polypeptides using standard methods such as activation of the carrier molecule with a heterobifunctional sulfosuccinimidyl 4-(n-maleimidomethyl)cyclohexane-1-carboxylate reagent. Cross-linking of an activated carrier to a peptide can occur by reaction of the maleimide group of the carrier with the sulfhydryl group of a peptide containing a cysteine residue. Conjugates can be separated from free peptide through the use of gel filtration column chromatography or other methods known in the art.

For instance, peptide/carrier molecule conjugates may be prepared by treating a mixture of peptides and carrier molecules with a coupling agent, such as a carbodiimide. The coupling agent may activate a carboxyl group on either the peptide or the carrier molecule so that the carboxyl group can react with a nucleophile (e.g., an amino or hydroxyl group) on the other member of the peptide/carrier molecule, resulting in the covalent linkage of the peptide and the carrier molecule.

For example, conjugates of a peptide coupled to ovalbumin may be prepared by dissolving equal amounts of lyophilized peptide and ovalbumin in a small volume of water. In a second tube, 1-ethyl-3-(3-dimethylamino-propyl)-carboiimide hydrochloride (EDC; ten times the amount of peptide) is dissolved in a small amount of water. The EDC solution is added to the peptide/ovalbumin mixture and allowed to react for a number of hours. The mixture may then be dialyzed (e.g., into phosphate buffered saline) to obtain a purified solution of peptide/ovalbumin conjugate.

The present invention also provides a composition that includes one or more active agents (i.e., polypeptides) of the invention and one or more pharmaceutically acceptable carriers. One or more polypeptides with demonstrated biological activity can be administered to a patient in an amount alone or together with other active agents and with a pharmaceutically acceptable buffer. The polypeptides can be combined with a variety of physiological acceptable carriers for delivery to a patient including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the peptide, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the active agent into association with a carrier which constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a patient, preferably a mammal, and more preferably a human, the composition of the invention in an amount effective to produce the desired effect. The peptides can be administered as a single dose or in multiple doses. Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949.

The agents of the present invention are preferably formulated in pharmaceutical compositions and then, in accordance with the methods of the invention, administered to a patient, such as a human patient, in a variety of forms adapted to the chosen route of administration. The formulations include, but are not limited to, those suitable for oral, rectal, vaginal, topical, nasal, ophthalmic, or parental (including subcutaneous, intramuscular, intraperitoneal, intratumoral, and intravenous) administration.

Formulations suitable for parenteral administration conveniently include a sterile aqueous preparation of the active agent, or dispersions of sterile powders of the active agent, which are preferably isotonic with the blood of the recipient. Isotonic agents that can be included in the liquid preparation include sugars, buffers, and sodium chloride. Solutions of the active agent can be prepared in water, optionally mixed with a nontoxic surfactant. Dispersions of the active agent can be prepared in water, ethanol, a polyol (such as glycerol, propylene glycol, liquid polyethylene glycols, and the like), vegetable oils, glycerol esters, and mixtures thereof. The ultimate dosage form is sterile, fluid, and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the active agent, preferably by filter sterilization. Preferred methods for preparing powders include vacuum drying and freeze drying of the sterile injectible solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the active agents over a prolonged period can be achieved by including agents for delaying, for example, aluminum monostearate and gelatin.

Formulations of the present invention suitable for oral administration may be presented as discrete units such as tablets, troches, capsules, lozenges, wafers, or cachets, each containing a predetermined amount of the active agent as a powder or granules, as liposomes containing the chemopreventive agent, or as a solution or suspension in an aqueous liquor or non-aqueous liquid such as a syrup, an elixir, an emulsion, or a draught. Such compositions and preparations typically contain at least about 0.1 wt-% of the active agent. The amount of polypeptide (i.e., active agent) is such that the dosage level will be effective to produce the desired result in the patient.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

In the examples presented herein, a series of dodecapeptides (SC-1 through SC-8) which "walk through" the amino acid sequence of βpep-25 (SEQ ID NO: 19) was investigated for the ability to kill bacteria and to neutralize LPS, specifically to kill Gram-negative and positive bacteria and to neutralize endotoxin. One of these SC peptides, SC-4 (KLFKRHLKWKII, SEQ ID NO:4), was identified as being exceptionally potent with an LD50 of 3 nanomolar against Gram-negative bacteria, even more potent than parent peptide βpep-25. Against Gram-positives, SC-4 also showed good activity with LD50s in the sub-micromolar range.

To demonstrate broad spectrum bactericidal activity, several strains were investigated: a rough strain of Gram-negative bacteria, J5; four clinically-relevant Gram-negative smooth stains (*Pseudomonas aeruginosa* J96, H5 and IA2), and two Gram-positive strains (MN-8 and MNHO). Moreover, since peptides which form both β-sheet and helix conformations can be bactericidal and these dodecapeptides were derived from a β-sheet-forming βpep peptide, CD and NMR data were acquired in aqueous solution and in 30% trifluoroethanol (TFE) solution to investigate into which conformational type these 12 mers fall.

Leakage studies performed using fluorescence microscopy, indicated rapid bacterial membrane permeability with t1/2 values of about 10 minutes at 100%-kill doses of peptide. SC-4 also effectively neutralized endotoxin in the micromolar range and is not hemolytic below $10^{-4}$ M. For all SC peptides, circular dichroic data strongly suggested the presence of both α-helix or $3_{10}$-helix. NOESY data acquired on SC peptides in the presence of 30% trifluoroethanol, also show NOEs characteristic of both α-helix or $3_{10}$-helix. Differences in activities among these helical dodecapeptides allowed some structure-function relations to be inferred. For SC-4 which is most $3_{10}$ helix-like, NOE-based computational modeling yields an amphipathic $3_{10}$ helical structure with K1, K4, R5, K8 and K10 being arrayed pentagonally on one face of the helix.

Several single-residue substituted variants of SC-4 were also investigated. Bactericidal activities in lysine/arginine-substituted norleucine variants of SC-4 vary, not surprisingly, from bacterial strain to strain. Against strain J5, any substitution shows no more than a 2-fold activity decrease, whereas against P.a., substitution at N-terminal positions K1, K4 or R5 drop activity significantly by about 20-fold. For endotoxin neutralization, substitution of charged groups has little effect, whereas removal of the C-terminal isoleucines drops activity by about 500-fold. Relative to other known bactericidal peptides in the linear peptide, helix-forming catagory, SC-4 appears to be the most potent, broad spectrum bactericidal agent identified to date.

The present invention also provides the three-dimensional structure of certain of the polypeptides derived using nuclear magnetic resonance (NMR) spectroscopy (e.g., one- and two-dimensional) and optionally circular dichroism (CD) spectroscopy. This information is of significant utility in fields such as drug discovery. An understanding of the structure of, for example SC-4, allows the design of drugs having similar structure, and hence, similar activity. Such drugs can be peptides, peptidomimetics (e.g., peptidic compounds in which the peptide backbone is substituted with one or more benzodiazepine molecules, peptides in which all L-amino acids are substituted with the corresponding D-amino acids, and "retro-inverso" peptides), and nonpeptidic mimetics. Such drugs are preferably nonpeptidic mimetics.

The structural data presented herein can be used (preferably in combination with Structure Activity Relationship (SAR) information and potential pharmacophore sites) to select a candidate compound (potential drug) from a database of three-dimensional structures of known compounds. The three-dimensional structures in the database can be either experimentally determined or computationally generated. Alternatively, a candidate compound can also be designed de novo. The candidate compound will have a three-dimensional structure that is at least in part (and preferably, substantially) similar to the three-dimensional structure of one of the polypeptides presented herein, preferably SC-4. Various molecular modeling and/or compound database search techniques known to one of skill in the art can be used for selecting candidate compounds. Such compounds can be evaluated for their biological activity using the assays described herein.

Specifically, the present invention provides detailed information about the shape and structure of the surface active domain of certain of the polypeptides described herein. Each of the constituent amino acids forming the "surface active domain" is defined by those shown in FIG. 6B. The term "surface active domain" refers to a region of a molecule or molecular complex that, as a result of its shape, is active for the treatment of one or more conditions, such as those described herein. Such surface active domain is the part of the polypeptide that is believed to be important for imparting the desired function. Thus, the structural information of just this domain can be used for identifying candidate compounds as described above.

The term "structure coordinates" refers to Cartesian coordinates (see Table 5) derived from computational modeling using internuclear distances obtained from NMR spectroscopic experiments, i.e., NOE's (see Table 6), as described in the Examples Section. The structure coordinates generate a unique configuration of points in space. It should be noted that these coordinates represent a statistical best fit representation of numerous structures for any one polypeptide, and that slight variations in individual structure coordinates would be expected. Also, similar or identical configurations can be defined by an entirely different set of coordinates, provided the distances and angles between coordinates remain essentially the same.

Figure 6B:
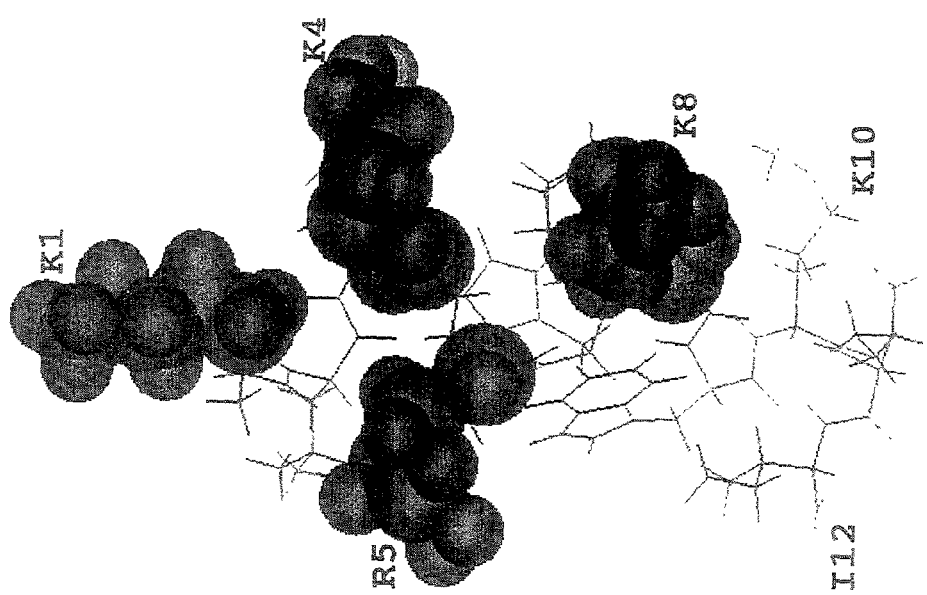
FIGS. 6A and 6B. NOE-Derived Structures of SC-4. For dodecapeptide SC-4, 14 final NOE-derived structures have been superimposed in FIG. 6A and structural statistics are given in Table 3. The average structure is shown in FIG. 6B, and four positively charged residues, K1, K4, R5, and K8, which lie on one surface of the amphipathic helix, are shown in the space-filling mode.

Generally, herein the structure is an amphipathic structure, such as a helix (which can be viewed as a cylinder), wherein one surface includes positively charged amino acid residues (preferably, one surface is composed primarily of positively charged amino acid residues (i.e., hydrophilic amino acid residues)) and the opposing surface includes hydrophobic amino acid residues (preferably, the opposing surface is composed primarily of hydrophobic amino acid residues). The surface active domain is identified by the positively charged amino acid residues and the hydrophobic opposing surface. In the case of SC-4, which has a helical structure, one surface includes four positively charged amino acid residues, although there may be more or less for other structures, and the opposing surface includes hydrophobic amino acid residues. More specifically, for SC-4, the surface active domain includes the structure coordinates of the atoms of the amino acid residues K1 (atoms 1–24), K4 (atoms 64–85), R5 (86–109), and K8 given in Table 5, as shown in FIG. 6B. An alternative way of visualizing the surface active domains is in terms of spatial relationships among functionally key residues derived from SAR (see, for example, FIG. 6B).

Various computational analyses can be used to determine whether a compound is sufficiently similar to the three-dimensional structure desired. Such analyses can be carried out in current software applications, as known in the art. This can involve a comparison of three-dimensional structure, hydrophobicity, steric bulk, electrostatic properties, bond angles, size or molecular composition, etc. For example, Quanta's Molecular Similarity package (Molecular Simulations Inc., Waltham, Mass.) permits comparison between different structures, different conformations of the same structure, and different parts of the same structure. Typically, the structure of the compound being analyzed is translated and rotated to obtain an optimum fit with the structure of the active polypeptide.

Preferred candidate structures are those having a set of structure coordinates with a root mean square deviation (i.e., the square root of the arithmetic mean of the squares of the deviations of the mean) of conserved residue atoms of less than 2.0 Angstroms when superimposed on the relevant structure coordinates. More preferably, the root mean square deviation is less than 1.0 Angstrom.

Once a candidate compound is identified using molecular modeling or database comparison techniques, it can be synthesized by a variety of techniques known to those of skill in the art.

One specific method of the present invention involves evaluating a candidate compound for structural similarity to that of KLFKRHLKWKII (SEQ ID NO:4) by: supplying a three-dimensional structure of KLFKRHLKWKII (SEQ ID NO:4) or a portion thereof; supplying a three-dimensional structure of a candidate compound; and comparing the three-dimensional structure of the candidate compound with the three-dimensional structure of KLFKRHLKWKII (SEQ ID NO:4) or a portion thereof.

EXAMPLES

Objects and advantages of this invention are further illustrated by the following examples, but the particular materials and amounts thereof recited in these examples, as well as other conditions and details, should not be construed to unduly limit this invention.

Methods & Materials

Peptide Preparation

Peptides were synthesized using a Milligen/Biosearch 9600 peptide solid-phase synthesizer using fluorenyl-methoxycarbonyl chemistry. Lyophilized crude peptides were purified by preparative reversed-phase HPLC on a C18 column with an elution gradient of 0–60% acetonitrile with 0.1% trifluoroacetic acid in water. Purity and composition of the peptides were verified by HPLC (Beckman Model 6300), amino acid analysis, and mass spectrometry.

Bacterial Strains

*Pseudomonas aeruginosa* type 1 is a clinical, smooth strain isolate serotyped by using the scheme of Homma, *Japan. J. Exp. Med.* 46, 329–336 (1976) and maintained in the lab by monthly transfer on blood agar plates. *E. coli* J96, IA2, and H5 are smooth strain, uropathogenic clinical isolates kindly maintained and provided by J. R. Johnson and described in Johnson et al., *J. Infect. Disease* 173, 920–926 (1996) for J96 and IA2 and in Johnson et al., *J. Infect. Disease* 173, 746–749 (1996) for H5. J5 is an *E. coli* rough strain initially referenced by G. R. Siber and discussed in Warren et al., *Infect. Immunity* 55, 1668–1673 (1987) and is analogous to the smooth strain *E. coli* 0111:B4 used in the BioWhittaker LAL endotoxin detection and quantitation kit described below. Gram-positive MN8 and MNHO are two patient isolates of *Staphylococcus aureus*, which were kindly provided by P. M. Schlievert and described in Bohach et al., *Rev. Infect. Diseases* 11, 75–82 (1989) for MNHO and in Schlievert et al., *J. Infect. Diseases* 147, 236–242 (1983) for MN8. All cultures are maintained on nutrient agar plates.

Bactericidal Assay

Pyrogen-free solutions were used throughout the assay. Log phase bacteria were obtained by transferring an overnight culture or scraping crystals off −85° C. glycerol stocks of overnight cultures. Bacteria were washed and resuspended in 0.9% sodium chloride with adjustment to an optical density at 650 nm which yields $3 \times 10^8$ CFU/ml. Bacteria were then diluted 1:10 in 0.08 M citrate phosphate buffer, pH 7.0 (prepared by mixing 0.08 M citric acid with 0.08 M dibasic sodium phosphate). Bacteria (0.15 ml) were incubated with peptide in a final volume of 1.0 ml of buffer. The assay was done in 17×100 polypropylene tubes in a reciprocal water bath shaker at 37° C. for 30 minutes. Following this 30 minute (min) incubation, 10-fold dilutions were made in 0.9% sodium chloride. Dilutions were done to $10^{-4}$ and 20 μl of each dilution was streaked across an agar plate. Gram-positive organisms were plated on nutrient agar plates containing 2% agar and Gram-negative organisms were plated on MacConkey agar (2%). Plates were incubated overnight at 37° C. and counted the next morning. The dilution containing 10–100 bacteria was counted and the number multiplied by 50 to adjust all counts to the number bacteria killed per milliliter. Peptide concentrations were converted to logarithm base ten and graphed. Bactericidal activity was determined by dose response where LD50 values were determined by best fits of a sigmoidal curve to the dose response data.

Limulus Amoebocyte Lysate Assay for LPS Neutralization

The ability of synthetic peptides to neutralize endotoxin was detected using the chromogenic QCL-1000 kit from BioWhittaker, Inc. (Walkersville, Md.) as described in their protocol. This method is quantitative for Gram-negative bacterial endotoxin (lipopolysaccharide, LPS). In the Limulus amebocyte lysate (LAL) assay, peptides that are active inhibit the LPS-mediated activation of a proenzyme (Young et al., *J. Clin. Invest.* 51, 1790–1797 (1972)) whose active form would release p-nitroaniline (pNA) from a colorless synthetic substrate (Ac-Ile-Glu-Ala-Arg-pNA), producing a yellow color (pNA) whose absorption is monitored spectrophotometrically at 405–410 nm. The initial rate of enzyme activation is proportional to the concentration of endotoxin present. The concentration of peptide required to bind to LPS and therefore to inhibit the Limulus amoebocyte lysate driven by 0.04 unit (or 0.01 ng) of *E. coli* 055:B5 LPS (from SIGMA) was determined by dose response.

Leakage Kinetics

Bacterial cell membrane integrity was measured using the LIVE/DEAD BacLight bacterial viability kit (L-7007) from Molecular Probes, Inc. (Eugene, Oreg.) which uses mixtures of red and green fluorescent stains to differentiate damaged and intact bacteria, respectively. Two *E. coli* strains (H5 and J5) and one *Staphylococcus aureus* strain (MN8) were investigated, and SC peptides were used at a dose that initiates 100% killing. Time points were taken between zero and 60 min. Fluorescence emission (excitation at 470 nm and emission at 490 nm to 700 nm) of each cell suspension was measured in a fluorescence spectrophotometer. 5 μL of each sample was placed on a microscope slide with a square cover slip and sealed to prevent movement.

Hemolytic Activity

Human red blood cells were washed three times using phosphate buffered saline (PBS: 35 mM phosphate buffer, 0.15 M NaCl, pH 7.0) prior to performing the assay. One hundred μL of human red blood cells suspended in 0.4% (v/v) PBS was placed in eppendorf tubes, and 100 μL of serially diluted peptides in PBS was added (peptide concentration ranged from 1 μM to 100 μM). Tubes were incubated for 1 hr at 37° C. and centrifuged at 1000 g for 5 min. One hundred μL aliquots of the supernatant was then transferred to eppendorf tubes, and hemolysis was measured by absorbance at 414 nm. Zero percentage hemolysis and 100% hemolysis were determined in PBS and in 1% Triton-X 100, respectively. The hemolysis percentage was calculated using the following formula: % hemolysis=[($A_{414}$ in the peptide solution−A414 in PBS)/(A414 in 1% Triton-X 100−A414 in PBS)]×100.

Circular Dichroism

Circular dichroic (CD) spectra were measured on a JASCO JA-710 automatic recording spectropolarimeter coupled with a data processor. Curves were recorded digitally and fed through the data processor for signal averaging and baseline subtraction. Peptides were dissolved (0.6 mg/mL) in 10 mM potassium phosphate buffer, pH 5.5, and CD spectra were recorded at 20° C. over a 190 nm to 250 nm range using a 0.5 mm path-length, thermally-jacketed quartz cuvette. Temperature was controlled by using a NesLab water bath. The scan speed was 20 nm/min. Spectra were signal-averaged 8 times, and an equally signal-averaged solvent baseline was subtracted. CD spectra on each peptide were acquired as a function of the concentration of trifluoroethanol (TFE) from 0% to 80% (volume/volume, v/v). CD spectra were deconvoluted as described by Sreerama et al., *Anal. Biochem.* 209, 32–44 (1993).

NMR Measurements

For NMR measurements, freeze-dried peptide was dissolved in $H_2O$. Peptide concentration was usually about 5 to 6 mM. pH was adjusted to pH 5.5 by adding μL quantities of NaOD or DCl to the peptide sample. NMR spectra were acquired on a Varian UNITY Plus-600 NMR spectrometer.

The water resonance was suppressed by direct irradiation (0.8 s) at the water frequency during the relaxation delay between scans.

2D-homonuclear magnetization transfer (HOHAHA) spectra, obtained by spin-locking with a MLEV-17 sequence (Bax et al., *J. Magn. Reson.* 65, 355–360. (1985)) with a mixing time of 60 ms, were used to identify spin systems. NOESY experiments (Wider et al., *J. Magn. Reson.* 56, 207–234 (1984)) were performed for conformational analysis. All 2D-NMR spectra were acquired in the States-TPPI phase sensitive mode (States et al., *J. Magn. Reson.* 48, 286–292 (1982); and Bodenhausen et al., *J. Magn. Res.* 37, 93–106 (1980)). The water resonance was suppressed by direct irradiation (0.8 s) at the water frequency during the relaxation delay between scans as well as during the mixing time in NOESY experiments. 2D-NMR spectra were collected as 256 to 512 t1 experiments, each with 2 k complex data points over a spectral width of 6 kHz in both dimensions with the carrier placed on the water resonance. For HOHAHA and NOESY spectra, 16 scans were time averaged per t1 experiment. Data were processed directly on the spectrometer or offline using VNMR (Varian, Inc., Palo Alto, Ca.) or NMRPipe (Delaglio et al., *J. Biomol. NMR* 6, 277–293 (1995)) on an SGI workstation. Data sets were multiplied in both dimensions by a 30–60 degree shifted sine-bell function and zero-filled to 1k in the t1 dimension prior to Fourier transformation.

Since SC peptides are quite hydrophobic and later found to be amphipathic, pulsed field gradient (PFG) NMR self-diffusion measurements were performed as a check for peptide aggregation. PFG-NMR experiments were done as described by Mayo et al., *Protein Sci.* 5, 1301–1315 (1996) using a Varian Unity-Plus 500 NMR spectrometer. The maximum magnitude of the gradient was 6-G/cm, and the PFG longitudinal eddy-current delay pulse-sequence was used for all self-diffusion measurements which were performed in D20 temperatures of 5° C. and 40° C. Peptide concentrations ranged from 0.1 mM to 15 mM. PFG NMR data were analyzed also as described by Mayo et al., *Protein Sci.* 5, 1301–1315 (1996).

Structural Modeling

Analysis of NOE growth curves indicated that backbone to backbone interproton NOEs were normally maximum at 300 ms to 400 ms. Interproton distance constraints were derived from NOEs assigned in $^1$H NOESY spectra acquired with mixing times of 200 ms and 400 ms. NOEs were classified as strong, medium, weak or very weak corresponding to upper bound distance constraints of 2.8, 3.3, 4.0, and 4.5 Å, respectively. The lower bound restraint between non-bonded protons was set to 1.8 Å. Pseudo-atom corrections were added to the upper bound distance constraints where appropriate, and a 0.5 Å correction was added to the upper bound for NOEs invsolving methyl protons. Hydrogen bond constraints were identified from the pattern of sequential and interstrand NOEs involving NH and CαH protons, together with evidence of slow amide proton-solvent exchange. Each hydrogen bond identified was defined using two distance constraints; $r_{NH-O}$=1.8 to 2.5 Å, and rN—O=1.8 to 2.5 Å.

Derived internuclear distance constraints were used in calculating structures for dodecapeptide SC-4 by using X-PLOR (Brunger et al., X-plor Manual,Yale University Press, New Haven (1992)). SC-4 was created using parallhdg.pro force fields. A template coordinate set was generated by using the Template routine. The ab initio simulated annealing (SA) protocol was then used. The SA procedure ran high temperature dynamics (3000 K for 120 ps) and then cooled down to 100 K in 50 K steps with 1.5 ps molecular dynamis at each step. Powell minimization was performed at 100 K for 1000 steps. Structure refinement was done based on simulated annealing starting at 1000 K and ending at 100 K. Final structures were subjected to the X-PLOR Accept routine with the violation threshold for NOEs of 0.5 Å and dihedral angles of 5°. Angles, bond lengths or impropers were not allowed to deviate from ideal geometry more than 5°, 0.05 Å and 5°, respectively. Structures were superimposed using the BIOSYM INSIGHT viewer (Molecular Simulations, Inc.) and were analyzed using X-PLOR analysis routines.

Cells, Cultures, and Reagents

Human umbilical vein derived EC (HUVEC) can be harvested from normal human umbilical cords by perfusion with 0.125% trypsin/EDTA as described in Groenewegen et al., *J. Exp. Med.* 164, 131–143 (1986). For determination of quiescent EC phenotype isolated ECs are immediately fixed in 1% paraformaldehyde. Human microvascular ECs (MVECs) are isolated. ECs are cultured in fibronectin coated tissue culture flasks in culture medium (RPMI-1640 with 20% human serum (HS), supplemented with 2 mM glutamine and 100 U/ml penicillin and 0.1 mg/ml streptomycin). For isolation of recombinant PF4, the synthetic gene for human native PF4 is expressed as a non-fusion protein in *E. coli* (BL21) cells (Repligen Corp., Cambridge, Mass.). The protein is purified, cleaved, and refolded essentially as described in Yang et al., *J. Biol. Chem.* 269, 20110–20118 (1994). Purity was assessed by Coomassie staining of SDS PAGE, analytical C4 reverse phase HPLC, and amino acid analysis. Typically, several hundred milligrams of greater than 95% pure material is isolated from 100 grams (g) of starting material.

EC Proliferation Assay

EC proliferation is measured using a [$^3$H]thymidine incorporation assay. ECs are seeded at 5000 cells/well in flatbottomed tissue culture plates and grown for 3 days, in the absence or presence of regulators, in culture medium. During the last 6 hours of the assay, the culture is pulsed with 0.5 μCi [methyl-$^3$H]thymidine/well.

In vitro Angiogenesis Assay

A semi-natural matrix of collagen type I is prepared by mixing 8 volumes vitrogen 100 (Collagen Corporation, Fermont, Calif., USA) with 1 volume 10× concentrated MEM (Life Technologies) and 1 volume of sodium bicarbonate (11.76 mg/ml). The matrix is dispensed into culture plates and allowed to gel at 37° C. Confluent BMEC (kindly provided by Dr. M. Furie, State University of New York, Stony Brook, USA) are trypsinized and seeded on top of this collagen matrix. When cells are grown to a confluent monolayer, medium is replaced by fresh medium, medium containing 25 ng/ml bFGF or medium containing 25 ng/ml bFGF and the peptides. In contrast to addition of the angiogenesis inducer on top of the matrix colon cell line (LS174T), spheroids are embedded in the collagen matrix before gelation. The peptides are added to the culture simultaneously with the EC. In both experiments, after 48 hours of incubation the (sprouting) endothelial monolayers are photographed with a Zeiss inverted phase-contrast photo microscope. The amount of sprouting in each well (i.e. the total length of the sprouts) is quantified by the computer program NIH image (Barendsz-Janson et al., *J. Vasc. Res.* 35, 109–114 (1998)).

CAM Assay

Fertile Lohman selected white leghorn eggs are incubated for three days at 37° C. and 55% relative humidity and rotated once every hour. At day 3, a rectangular window (1×2 cm) is made in the eggshell. The window is covered with tape to prevent dehydration. The window allows undisturbed observation of the developing vasculature of the chorio-allantoic membrane (CAM). At day 7 a silastic ring (10 mm diameter) is placed on the CAM to allow local drug administration within the ring. Peptides dissolved in sterile saline (0.9% NaCl) are applied daily in aliquots of 65 μl from day 10 to day 13. At day 14 the CAMs are photographed.

Immunofluorescence

Fluorescence activated cell sorter (FACS) anaylsis using indirect phycoerythrin (PE)-conjugated reagents requirs 3 separate incubations. ECs (1×10$^5$) are fixed for 1 hr in 1% paraformaldehyde, resuspended in 20 μl appropriately diluted MAb and incubated for 1 hour on ice. Subsequently, cells are washed 2 times in phosphate-buffered saline/bovine serum albumin (PGS/BSA) (0.1%) and incubated for another 30 minutes with biotinylated rabbit-anti-mouse Ig (Dako, Glostrup, Denmark). After another 2 washing, cells are incubated with streptavidin-phycoerythrin conjugate (Dako). Stained cells are analyzed on a FACScan flowcytometer. Data analysis is performed using PCLysys software (Becton Dickinson, Mountain View, Calif.).

Inhibition of Angiogenesis Prevents bFGF Induced ICAM-1 Down-regulation

To test the hypothesis that angiostatic factors can prevent angiogenesis-mediated down-regulation of EAM, a polypeptide can be tested for its effects on EAM expression. These studies concentrate on the expression of ICAM-1 because previous research using anti-ICAM-1 and anti-LFA-1 antibodies demonstrated that the ICAM-1/LFA-1 interaction is crucial, i.e., both essential and sufficient, in leukocyte/EC adhesion and extravasation (Bevilacqua, *Ann. Rev. Immunol.* 11, 767–804 (1993); and Springer *Cell* 76, 301–314 (1994)). A 3-day incubation of EC with 10 ng/ml bFGF to evaluate the attenuation of ICAM-1 expression is compared with control cells.

Results

FIG. 1 shows the amino acid sequences for βpep-19 (SEQ ID NO: 18), βpep-25 (SEQ ID NO: 19), and peptide dodecamers (SC peptides) which "walk through" the sequence of βpep-25. The bactericidal activity of βpep-25 was observed to be equal to or better than that of βpep-19, and these "walk throughs" were designed to identify segments of that amino acid sequence that contributed most to this activity. It was anticipated that bactericidal activity in these shorter SC peptides would be considerably less than that for parent peptide βpep-25. As reported below, this was not the case and is the basis for this work.

Bactericidal Activities

Figure 2B:
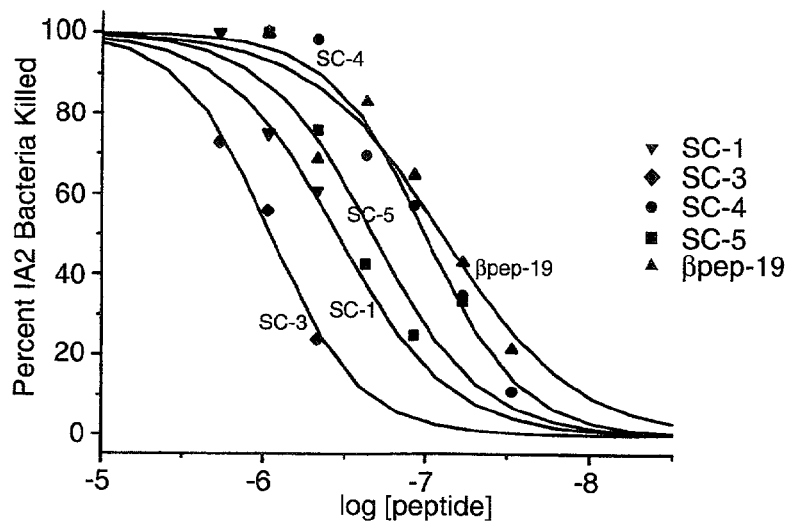
Figure 2C:
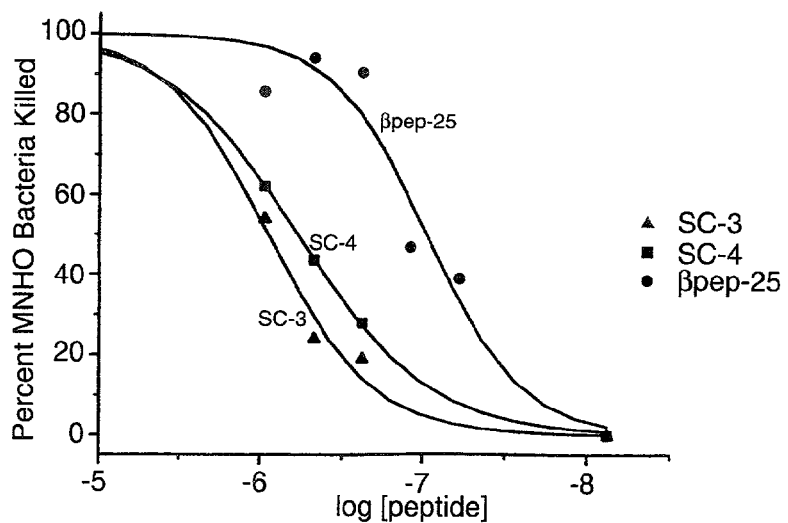

Chosen for investigation were seven bacterial strains, representing both Gram-negative and positive bacteria. For βpep peptides and βpep-derived dodecapeptides, bactericidal activities against these strains are given in Table 1 as the concentration which is effective at killing 50% of bacteria, i.e., LD50. LD50 values were determined from dose response curves like those shown in FIGS. 2A–2C which plot percentage bacteria killed versus logarithm of the peptide concentration. Actual data points are shown with symbols as identified in the legend, and each curve represents the best fit using a sigmoidal function. LD50 values are read from the fitted curve at 50% mortality. Overall, SC-4 functions best at killing both rough and smooth strain Gram-negative bacteria. LD50s range from 3 nanomolar against J5 to 250 nanomolar against J96. Against strains of *S. aureus*, SC-4 (80 to 400 nanomolar) and SC-5 (180 to 350 nanomolar) are comparable in activity to βpep-19 and βpep-25. BG-22, a peptide 28 mer having the amino acid sequence from the β-sheet domain of bactericidal/permeability increasing (B/PI) protein (residues 82–108) (Gray et al., *Biochim. Biophys. Acta* 1244, 185–190 (1995)) proposed as being that site which promotes bactericidal activity, is less bactericidal than βpep-19 or βpep-25 and considerably less active than SC-4. In general, SC-4 demonstrates the best broad spectrum bactericidal activity.

Leakage Kinetic

Bactericidal peptides are thought to function generally by integrating into the bacterial membrane and creating channels such that bacteria become "leaky" and die. To assess if this mechanism of action occurs with SC peptides, as well as with βpep peptides, membrane leakage kinetics were investigated against two *E. coli* strains (H5 and J5) and one *S. aureus* strain (MN8). In each case, bacteria became "leaky" within a few minutes after the addition of peptide. For any one of these strains, $t_{1/2}$ values are estimated to be in the range of 10 min.

Hemolytic Activity

Considering potential use of these peptides as antibiotic agents in mammals, it is important to know their potential to lyse eukaryotic cells. For these information, red blood cells were used as a model for all eukaryotic cells. Red blood cell lysis (hemolysis) was checked at peptide concentrations of $1 \times 10^{-4}$ M, $1 \times 10^{-5}$ M, and $1 \times 10^{-6}$ M. At $10^{-6}$ M, SC-1, SC-5 and BG-22 demonstrated 15% to 30% hemolysis which increased to around 70% at $10^{-4}$ M. All other peptides showed less than 5% to 10% effect at $10^{-6}$ M. Even at $10^{-4}$ M, βpep-25 induced only about 5% hemolysis, while SC-3, SC-4, and SC-8 gave about a 10% effect, and SC-2, SC-6 and SC-7 gave about a 15% effect. For most SC peptides, $10^{-4}$ M concentration is considerably greater than its bactericidal LD50 value. For example, for SC-4, LD50s against *P. aeruginosa* and MN-8 are 50,000-times and 500-times, respectively, less than this concentration.

LPS neutralization

Lysis of Gram-negative bacteria produces the endotoxin lipopolysaccharide (LPS) which triggers the pathologic disorder known as sepsis. In this respect, peptides which are not only bactericidal, but also effectively neutralize LPS, are of considerable importance in combating endotoxemia and sepsis. Therefore, these peptides were tested in the Limulus amebocyte assay for their ability to bind to and to neutralize LPS. IC50 values were determined from dose response curves shown in FIG. 3 and are listed in units of micromolar at the right most column in Table 1. βpep-19, βpep-25 and SC-5 are essentially equi-potent (IC50 values of about 2 micromolar), with SC-4 being not far behind. SC-1 and SC-6 are slightly less effective having IC50s of 3.5 micromolar. SC-3 is about 10-fold less potent (IC50=25×10$^{-6}$ M) than either SC-4 or SC-5. SC-2, SC-7 and SC-8 show no LPS binding activity at or below 1×10–4 M. This was not so surprising for SC-7 and SC-8 which are essentially bactericidally inactive, but SC-2 did demonstrate reasonable bactericidal activity.

TABLE 1

SC series of peptides -- LD50 values for bactericidal activity and IC50 values for neutralization of bacterial lipopolysaccharide (LPS). All values are given as micromolar quantities.

| | Gram neg. rough [$10^{-6}$ M] | Gram neg. smooth [$10^{-6}$ M] | | | Gram-positive [$10^{-6}$ M] | | LPS effect [$10^{-6}$ M] |
|---|---|---|---|---|---|---|---|
| | J5 | P.a. | J96 | H5 | IA2 | MN8 | MNHO | |
| βpep-19 | 0.01 | 0.03 | 0.1 | 0.71 | 0.06 | 0.25 | 0.16 | 2 |
| βpep-25 | 0.02 | 0.06 | 0.13 | 0.20 | 0.30 | 0.16 | 0.1 | 1.6 |
| BG-22 | 0.09 | 0.05 | 0.52 | 0.71 | 0.32 | 0.5 | 0.63 | 5 |
| SC-1 | 0.24 | 0.86 | 0.12 | 0.7 | 0.48 | 0.65 | 0.48 | 3.5 |
| SC-2 | 0.13 | 0.05 | 1.3 | 0.63 | 0.8 | 0.8 | 0.28 | XXX |
| SC-3 | 0.01 | 0.01 | 0.63 | 1.3 | 0.8 | 1.2 | 1 | 25 |
| SC-4 | 0.003 | 0.01 | 0.25 | 0.08 | 0.08 | 0.35 | 0.4 | 1.9 |
| SC-5 | 0.02 | 0.13 | 0.2 | 0.63 | 0.33 | 0.35 | 0.18 | 1.6 |
| SC-6 | 0.4 | 0.09 | 1.1 | 1.3 | 0.4 | 0.48 | 0.35 | 3.5 |
| SC-7 | XXX | XXX | XXX | XXX | XXX | XXX | XXX | XXX |
| SC-8 | XXX | XXX | XXX | XXX | XXX | XXX | XXX | XXX |

Bacteria J5, J96, H5, and IA2 are strains of *E. coli*; bacteria MN8 and MNHO are strains of *S. aureus*.
LD50 and IC50 values are in units of $10^{-6}$ M.
Standard deviations are about ±30% of the values given.
XXX means not active at concentrations below $1 \times 10^{-5}$ M in the bactericidal assay and below $1 \times 10^{-4}$ M in the LPS neutralization assay.

Circular Dichroism

Figure 4B:
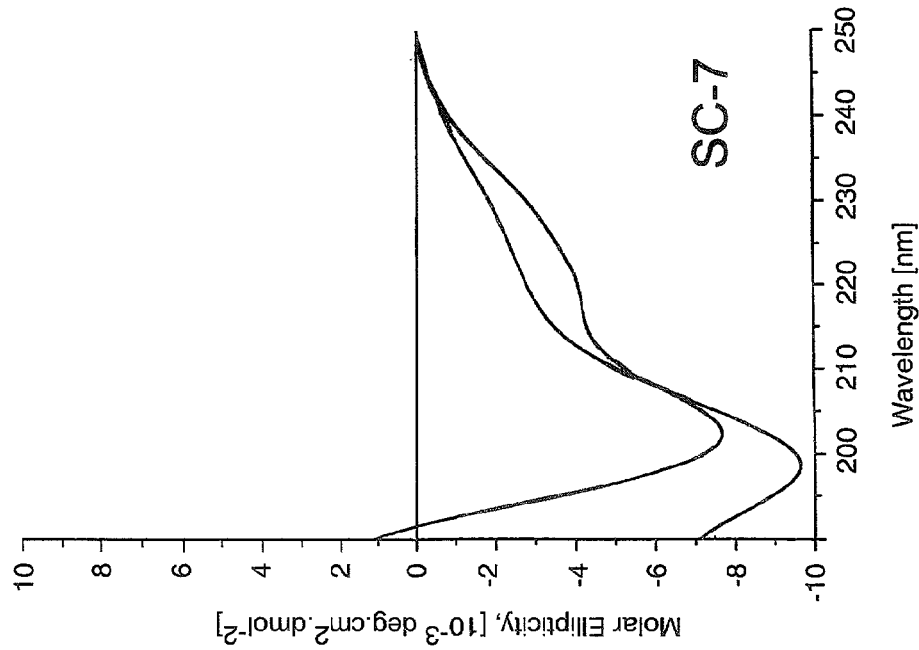
FIGS. 4A through 4C. CD Spectra for SC Peptides. Far-ultraviolet circular dichroic spectra for two SC peptides, SC-5 and SC-7, are shown in FIGS. 4A and 4B, respectively, as mean residue ellipticity versus wavelength (nm). Peptide concentration was 40 μM in 20 mM potassium phosphate, pH 6.3. The temperature was set at 20° C. Other experimental conditions are discussed in the Methods Section. CD traces shown were acquired as a function of TFE concentration from 0% to 70% (volume/volume).
Figure 4A:
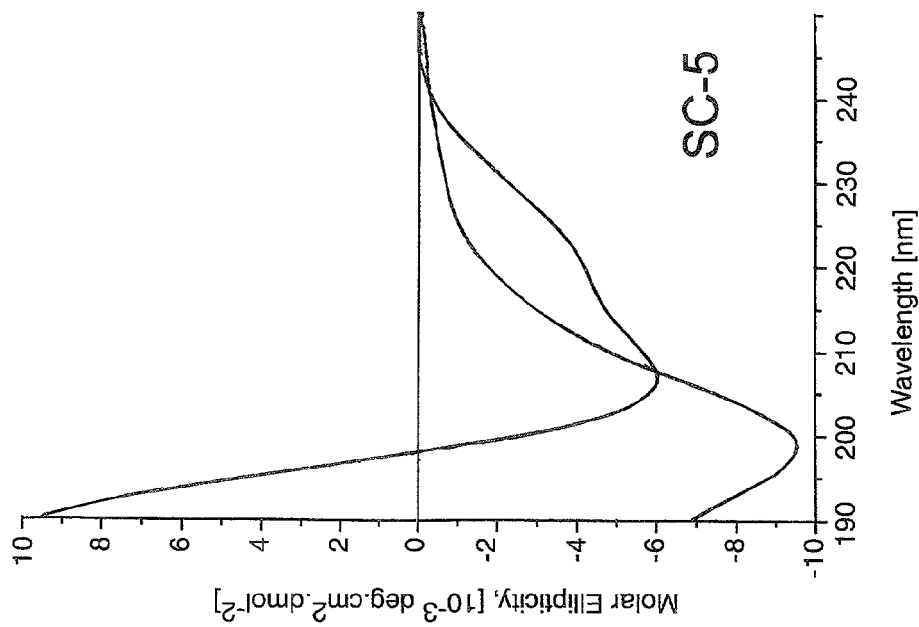
Figure 4C:
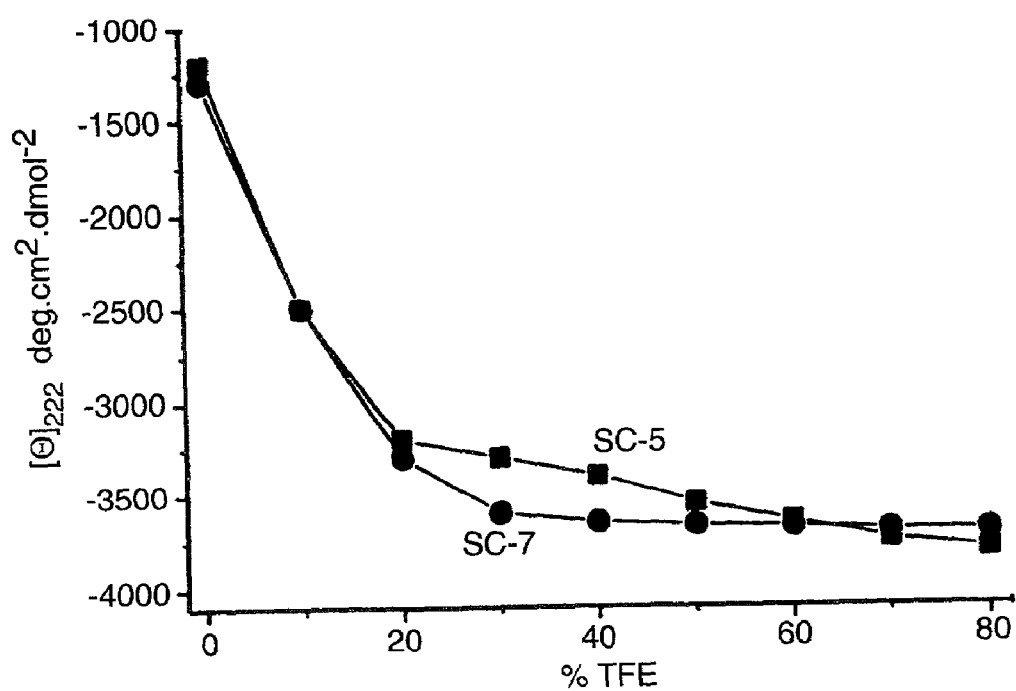

CD spectroscopy, used to assess conformational populations of SC peptides, indicates the presence of helical structure. This is demonstrated in FIGS. 4A–4C which show select CD traces for SC-5 and SC-7 acquired at various concentrations of TFE. In all cases, CD traces show a band of negative ellipticity at 222 nm which is characteristic of helix conformation (Greenfield et al., *Biochemistry* 8, 4108–4116 (1969); Johnson et al., *Proteins* 7, 205–214 (1990); and Waterhous et al., *Biochemistry* 33, 2121–2128 (1994)). At lower concentrations of TFE, mostly random coil populations are present as evidenced by a negative ellipticity minimum at about 200 nm (rather than at 207/208 nm for helix) and a low $[\Theta]_{222}/[\Theta]_{200}$ ratio. As the concentration of TFE is increased, helix population increases since the negative ellipticity band at 200 nm shifts closer to 207 nm and the 222 nm band becomes more negative. At about 20% to 30% TFE, both these observables have nearly plateaued as indicated in FIG. 4C which plots $[\Theta]_{222}$ versus % (v/v) TFE. These CD spectral characteristics, however, would result from the presence of either α-helix or $3_{10}$-helix or from a mixture of both. The right handed $3_{10}$ helix displays a negative CD band at 207 nm ($\lambda_{min}$) and a shoulder centered near 222 nm with the ratio $[\Theta]_{222}/[\Theta]_{207}$ being about 0.4 (Millhauser, *Biochemistry* 34, 3873–3877 (1995); and Toniolo et al., *J. Am. Chem. Soc.* 118, 2744–2745 (1996)). For an α-helix, the 207 nm and 222 nm bands are also present; however, the ratio $[\Theta]_{222}/[\Theta]_{207}$ is closer to unity. When $\lambda_{min}$ is 207 nm and the ratio $[\Theta]_{222}/[\Theta]_{207}$ is between 0.4 and 1.0, interconverting populations of $3_{10}$ helix and α-helix are likely present.

For SC peptides, Table 2 lists the wavelength for the far UV minimum, $\lambda_{min}$, and the ratio $[\Theta]_{222}/[\Theta]_{207}$ at 70% TFE. In cases where the $[\Theta]_{222}/[\Theta]_{207}$ ratio is closer to 0.4 than to 1.0 and $\lambda_{min}$ is at 207 nm, the conformation of that SC peptide should have more $3_{10}$ helix than α-helix character (Millhauser, *Biochemistry* 34, 3873–3877 (1995); and Toniolo et al., *J. Am. Chem. Soc.* 118, 2744–2745 (1996)). For the most active peptide, SC-4, $\lambda_{min}$ is 207 nm and $[\Theta]_{222}/[\Theta]_{207}$ is 0.49, indicating the presence of mostly $3_{10}$ helix. Even though peptides SC-1, -2, -3, -5 and -6 have $\lambda_{min}$ values of 207 nm, larger $[\Theta]_{222}/[\Theta]_{207}$ ratios of 0.6 to 0.7 indicate less $3_{10}$ helix character. Since SC-7 and SC-8 show $\lambda_{min}$ values of 203 nm and 204 nm, respectively, significant populations of random coil should be present in their conformational ensembles.

TABLE 2

Circular Dichroism Data Summary for peptides in the presence of 70% trifluoroethanol.

| | λ minimum (nm) | $[\Theta]_{222}/[\Theta]_{207}$ ratio |
|---|---|---|
| SC-1 | 208 | 0.83 |
| SC-2 | 207 | 0.65 |
| SC-3 | 207 | 0.59 |
| SC-4 | 207 | 0.46 |
| SC-5 | 207 | 0.64 |
| SC-6 | 207 | 0.73 |
| SC-7 | 202 | 0.5 |
| SC-8 | 204 | 0.48 |
| SC-4 Variants: | | |
| SC-401 | 207 | 0.63 |
| SC-402 | 204 | 0.52 |
| SC-403 | 208 | 0.79 |
| SC-404 | 207 | 0.54 |
| SC-405 | 207 | 0.71 |
| SC-406 | 208 | 0.67 |
| SC-407 | 207 | 0.58 |
| SC-408 | 207 | 0.53 |
| SC-409 | 208 | 0.65 |

NMR Conformational Analysis

Figure 5A:
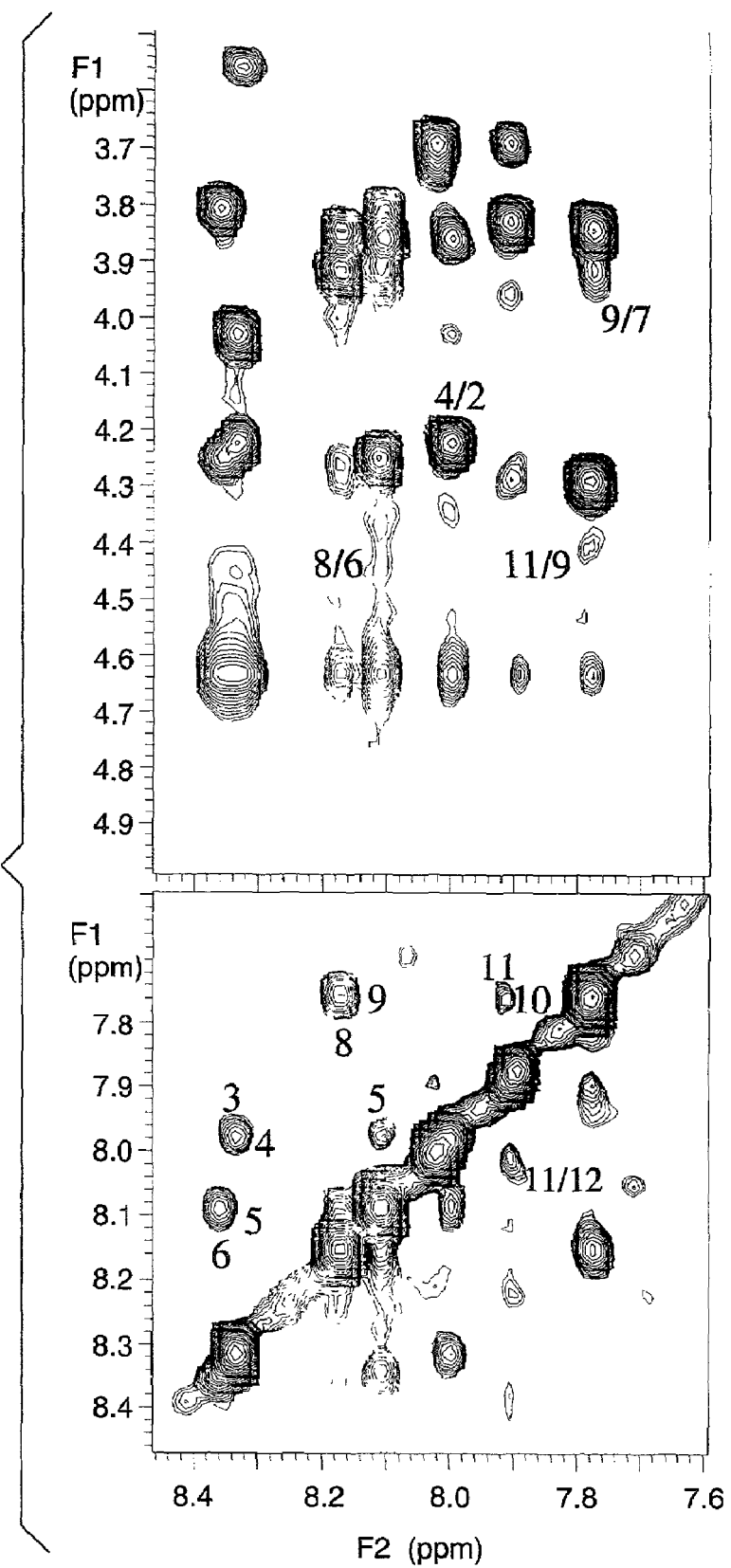
FIGS. 5A and 5B. NOESY Spectra for SC-4. 600 MHz $^1$H NMR spectra are shown for SC-4 in the presence (5A) and absence (5B) of 30% trifluoroethanol/70% water. Peptide concentration was 6.3 mM in 10 mM potassium phosphate, pH 5.5 and 25° C. Spectra were accumulated with 8 k data points over 6000 Hz sweep width and were processed with 1 Hz line broadening. Only spectral regions downfield from the HDO resonance are shown and some resonance assignments are indicated.
Figure 5B:
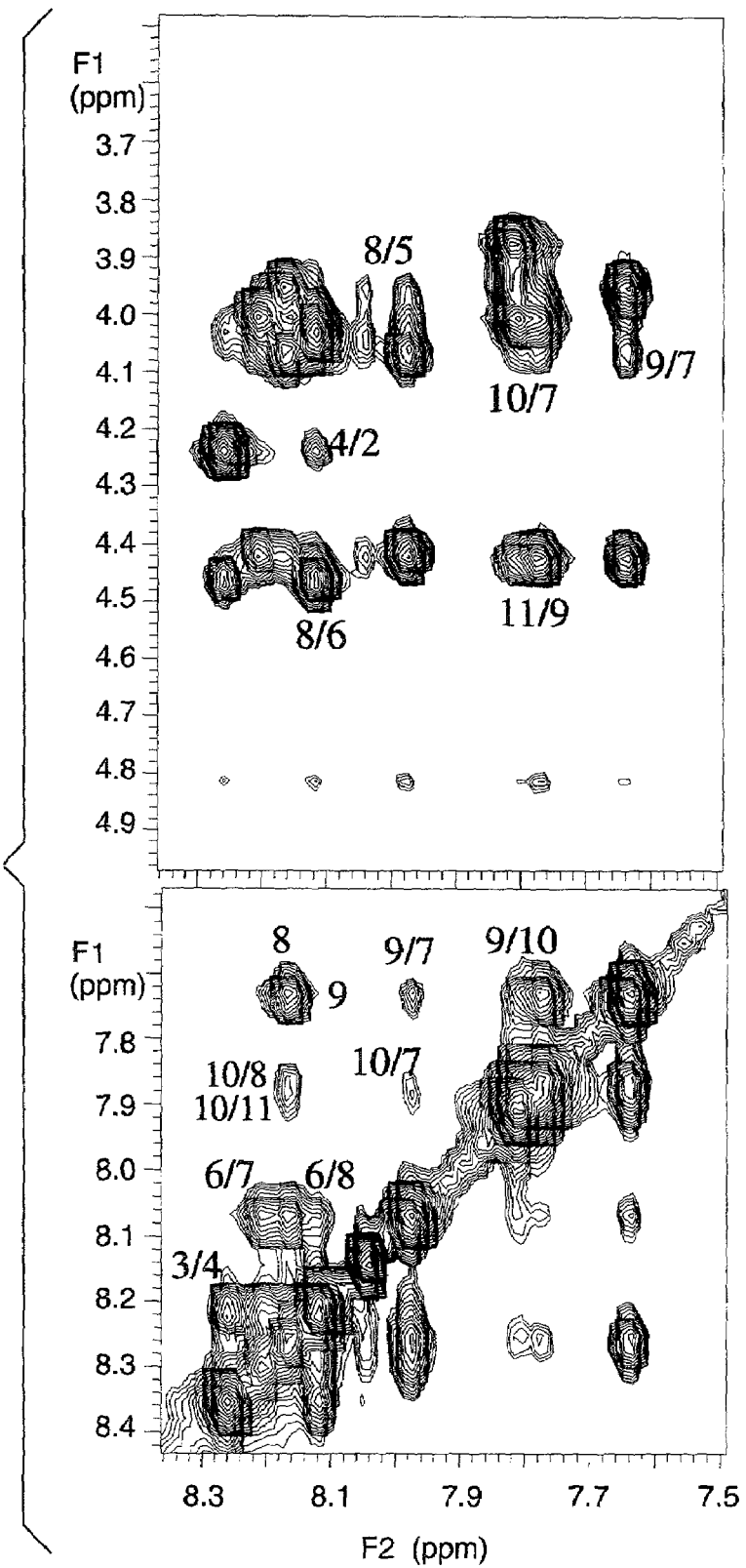

FIGS. 5A and 5B show αH—NH and NH—NH regions from NOESY data for SC-4 in the absence (FIG. 5A) and presence (FIG. 5B) of 30% (v/v) TFE. In either case, the series of NH—NH NOEs running from F3 to I12 alone indicates the presence of at least nascent helix conformation (Dyson et a., *J. Mol. Biol.* 201, 201–217 (1988)). Moreover, even in the absence of TFE, all four αH-NH i,i+2 NOEs are easily distinguishable, supporting the presence of multiple turn or $3_{10}$ helix (Wüthrich et al. *NMR of Proteins and*

*Nucleic Acids*, Wiley-Interscience, New York (1986); and Wishart et al., *Biochemistry* 31, 1647–1651 (1992)). In the presence of TFE, these NOEs remain and other longer range NOEs appear. For example, two αH—NH i,i+3 (8/5, 10/7), three NH—NH i,i2 (8/6,9/7, 10/8) and two NH—NH i,i+3 (10/7, 11/8) NOEs have been labeled in FIGS. 5A and 5B. For pure $3_{10}$ helix, only i,i+2 and i,i+3 NOEs should be observed, whereas for pure α-helix, only i,i+3 and i,i+4 NOEs should be present (Wüthrich, *NMR of Proteins and Nucleic Acids*, Wiley-Interscience, New York (1986)). The presence of αH-NH i,i+2 NOEs characteristic of $3_{10}$ helix is consistent with CD results as discussed above, α-helix conformation, however, must also contribute to the conformational ensemble as indicated by CD data. Since all SC peptides, to various extents, show similar NOE and CD trends, these peptides exist in aqueous solution in an equilibrium primarily among $3_{10}$ helix, α-helix and random coil.

Since some SC peptides are relatively hydrophobic and could tend to self-associate thereby affecting the presence and/or magnitude of NOEs, PFG NMR diffusion measurements (data not shown) were made. For all SC peptides, diffusion coefficients derived from these data remain unchanged over the peptide concentration range of 0.1 mM to 15 mM, indicating the absence of aggregation.

For peptide SC-4 which forms the most stable $3_{10}$ helical structure and is generally the most bactericidal, conformational modeling was performed using NOE data acquired for the peptide in the presence of 30% TFE/70% water. It should be emphasized that most of the same NOEs could be observed in the absence of TFE; however, 30% TFE did apparently stabilize the helix conformation and increase the overall tumbling correlation time, thereby generally increasing the magnitude of NOEs. A total of 140 NOE distance contraints were derived from analysis of NOESY spectra. These include 68 intraresidue, 24 sequential, 20 medium-range (|i–j|<5), and 27 long-range (|i–j|≧5) constraints. In addition, a total of 8 hydrogen bonds could be identified inspection of initial SC-4 structures and from long lived backbone NHs, giving rise to 16 hydrogen bond distance constraints. The total number of experimentally derived constraints was therefore 156, giving an average of 13 contraints per residue.

Figure 6A:
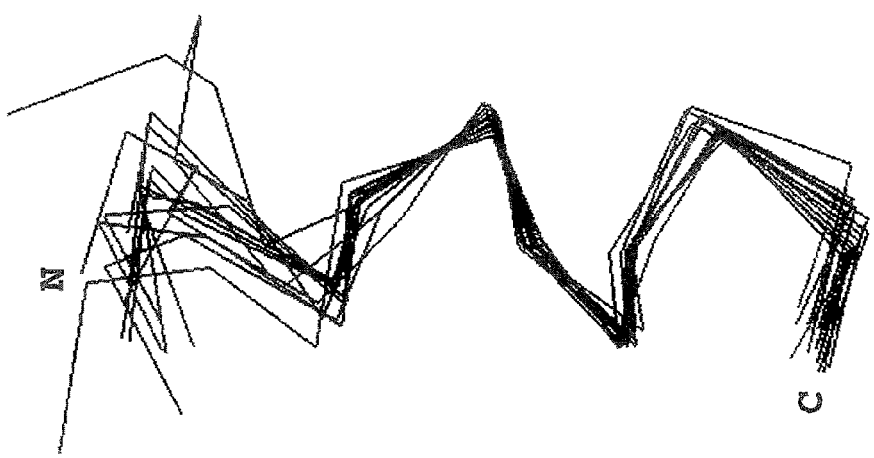

Initially, 100 structures for SC-4 were calculated as described in the Methods Section. The best fit superpositions of backbone Cα atoms for the final 14 structures are shown in FIG. 6A. These structures showed no NOE violations greater 0.5 Å. Structural statistics are summarized in Table 3. The somewhat less structurally-defined N-terminus is apparent. The structures satisfy experimental constraints quite well. For residues 3 through 12, atomic RMS differences with respect to the mean coordinate positions are 0.71±0.08 Å for backbone (N,C$^\alpha$, C) atoms and 1.4±0.4 Å for all heavy atoms. In addition, φ and ψ angular order parameters are all>0.8. Together, the above data indicate that these structures used to represent the solution conformation of SC-4 are well converged. The helical structure of SC-4 is, not surprisingly, between that of an α-helix and a $3_{10}$ helix, with the average number of residues per turn being 3.3. From the N-terminus to W9, the helix is amphipathic with K1, K4, R5 and K8 aligned on one face as illustrated in FIG. 6B with these residues being highlighted.

TABLE 3

Structural Statistics for the calculated structures of SC-4 from NMR data.

RMS Deviations from experimental distance restraints (Å)[a]

| | |
|---|---|
| NOE (140) | 0.04 ± 0.0042 |
| H-bond (16) | |
| Deviations from idealized geometry | |
| Bonds (Å) | 0.038 |
| Angles (°) | 0.65 ± 0.03 |
| Impropers (°) | 0.25 ± 0.03 |
| Energies (kcal.mol$^{-1}$) | |
| ENOE[b] | 9 ± 1 |
| ECDIH | 1.3 ± 0.6 |
| ENCS | 11.6 ± 1 |
| EBOND | 3.7 ± 0.4 |
| EANGLE | 30 ± 5 |
| EIMPROPER | 16 ± 2 |
| ETOTAL | 72 ± 7 |

[a]None of the 14 final structures exhibited distance restraint violations greater than 0.5 Å or dihedral angle violations greater than 5°. RMSD values represent the mean and standard deviations for the 14 structures.
[b]The final values of the NOE (ENOE), torsion angle (ECDIH) and NCS (ENCS) potentials have been calculated with force constants of 50 kcal-.mol$^{-1}$.Å$^{-2}$, 200 kcal.mol$^{-1}$.rad$^{-2}$ and 300 kcal.mol$^{-1}$.Å$^{-2}$, respectively.

Effects of Modifying the SC-4 Sequence

Since SC-3 and SC-4 were the most bactericidal, least hemolytic and SC-4 was one of the best at neutralizing endotoxin, additional dodecapeptide "walk throughs" were made to complete the single-residue shifts between SC-3 and SC-4:

SC-401 Q M K L F K R H L K W K-NH2 (SEQ ID NO: 9)

SC-402 M K L F K R H L K W K I-NH2 (SEQ ID NO: 10)

In addition, a longer variant which extends SC-4 by one residue on each side of the sequence was investigated:

SC-403 M K L F K R H L K W K I I V-NH2 (SEQ ID NO: 10)

Since the presence of positively charged residues is known to be crucial to bactericidal and LPS neutralizing activities, a series of lysine/arginine-substituted SC-4 variants was investigated:

SC-404 X L F K R H L K W K I I-NH2 (SEQ ID NO: 12)

SC-405 K L F X R H L K W K I I-NH2 (SEQ ID NO: 13)

SC-406 K L F K R H L X W K I I-NH2 (SEQ ID NO: 14)

SC-407 K L F K R H L K W X I I-NH2 (SEQ ID NO: 15)

SC-408 K L F K K H L K W K I I-NH2 (SEQ ID NO: 16)

SC-409 K L F K X H L K W K I I-NH2 (SEQ ID NO: 17)

SC-404 thru SC-407 change each of the four lysines to norleucines (lysine without the side-chain amine group). Variants SC-408 and SC-409 change the arginine, R5, to lysine and norleucine, respectively.

CD data indicate that these variants also fold helically, fluctuating between $3_{10}$ and α-helical structure like parent peptides SC-3 and SC-4 (data not shown). Table 2 lists $\lambda_{min}$ and $[\Theta]_{222}/[\Theta]_{207}$ ratio values at 70% TFE. Whereas SC-401 and SC-403 both demonstrate $\lambda_{min}$ values of about 207 nm, their $[\Theta]_{222}/[\Theta]_{207}$ ratios are larger than those of either SC-3 or SC-4, indicating that these two SC-4 variants have more α-helix and less $3_{10}$ helix character than parent peptide SC-4. SC-402, however, has a greater random coil population in its conformational ensemble since its $\lambda_{min}$ value is 204 nm. The lysine/arginine variants, SC-404 through SC-409 behave conformationally like parent SC-4, with considerable $3_{10}$ helix character. NMR data, acquired in the presence of 30% TFE (data not shown), support the presence of significant populations of helical conformation as observed for SC-3 and SC-4.

Bactericidal activities from these peptides were acquired against three of the strains used above, *E. coli* J5, *P. aeruginosa* and *S. aureus* MNHO. Results are given in Table 4. Against J5, SC-401 and SC-402 are more active than SC-3 and slightly less active than SC-4. Shifting the dodecapeptide unit from SC-3 towards SC-4, therefore, increases activity. On the other hand, addition of hydrophobic residues to both terminal positions in SC-4, i.e., SC-403, increases activity slightly. Using *P. aeruginosa*, bactericidal dose response curves indicate that either dodecapeptide, SC-401 or SC-402, diminishes activity. This is somewhat surprising since both SC-3 and SC-4 have the same activity against *P. aeruginosa* (see Table 1). This may have something to do with the way in which these peptides interact with the bacterial cell wall/membrane. Against *S. aureus* strain MNHO, shifting the dodecapeptide window from SC-3 towards SC-4 by only one residue, i.e., SC-401, essentially abolishes activity. Another one residue shift (SC-402) brings back some activity, and lengthening both termini of SC-4 has no effect.

TABLE 4

SC-4 peptide variants SC401 thru SC-409 -- LD50 values for bactericidal activity and IC50 values for neutralization of bacterial lipopolysaccharide (LPS).
All values are given as micromolar quantities.

|  | Gram-neg. rough ($10^{-6}$ M) J5 | Gram-neg. smooth ($10^{-6}$ M) P.a. | Gram-positive ($10^{-6}$ M) MNHO | LPS neutralization ($10^{-6}$ M) |
|---|---|---|---|---|
| SC-3 (parent) | 0.01 | 0.01 | 1 | 25 |
| SC-4 (parent) | 0.003* | 0.01 | 0.4 | 2 |
| SC-401 | 0.004 | 0.06 | XXX | 126 |
| SC-402 | 0.005 | 0.07 | 6 | 25 |
| SC-403 | 0.002 | 0.05 | 0.4 | 6 |
| Lysine/Arginine variants: | | | | |
| SC-404 (K1X) | 0.004 | 0.22 | 1 | 7 |
| SC-405 (K4X) | 0.006 | 0.17 | 0.4 | 7 |
| SC-406 (K8X) | 0.005 | 0.05 | 2 | 3 |
| SC-407 (K10X) | 0.007 | 0.05 | 1 | 3 |
| SC-408 (R5K) | 0.003 | 0.07 | 2 | 1000 |
| SC-409 (R5X) | 0.001 | 0.22 | 0.3 | 3 |

*LD50 and IC50 values are in units of $10^{-6}$ M.
Standard deviations are about ±30% of the values given.
XXX means not active at concentrations below $1 \times 10^{-5}$ M.

With the lysine variants, substitution of K1 or K4 for norleucine reduces the bactericidal activity against J5 only slightly, whereas substitution of K8 and K10 for norleucine shows a somewhat more significant drop in activity. This is especially true for SC-407 (K10X). Nonetheless, bactericidal activities remain respectable indicating that removal of a single positive charge alone does not abolish activity. Substitution of R5 for lysine, however, shows no change in activity, while substitution of R5 for norleucine causes a significant activity increase. The NRM solution structure of SC-4 shows that K1, K4, R5 and K8 lie on one face of an amphipathic helix with K10 more to the side (FIG. 6B). This conformation of the peptide sandwiches K4 and R5 between K1 and K8. Removal of the charged group at position 5 may help to reduce charge-charge repulsion and to stabilize, via hydrophobic interactions, the remainder of the lysine core.

Once again, any changes to the SC-4 amino acid sequence reduce bactericidal effects against *P. aeruginosa* (Table 4). In the lysine/arginine series, substitution of K1, K4 and R5 for norleucine has the most detrimental effects. Against *S. aureus* strain MNHO, substitution of any one of these charged residues is more tolerated (Table 4).

These data also indicate that while the mechanism of action of these peptides against various bacterial strains may be similar, there are discrete and significant differences related to the spatial orientation of charged and hydrophobic groups of the peptides. Moreover, even though CD and NMR data indicate helical conformation for these peptides, interaction with the bacterial cell wall/membrane may certainly modify this conformation making derivation of precise structure-activity relations impossible.

Figure 3:
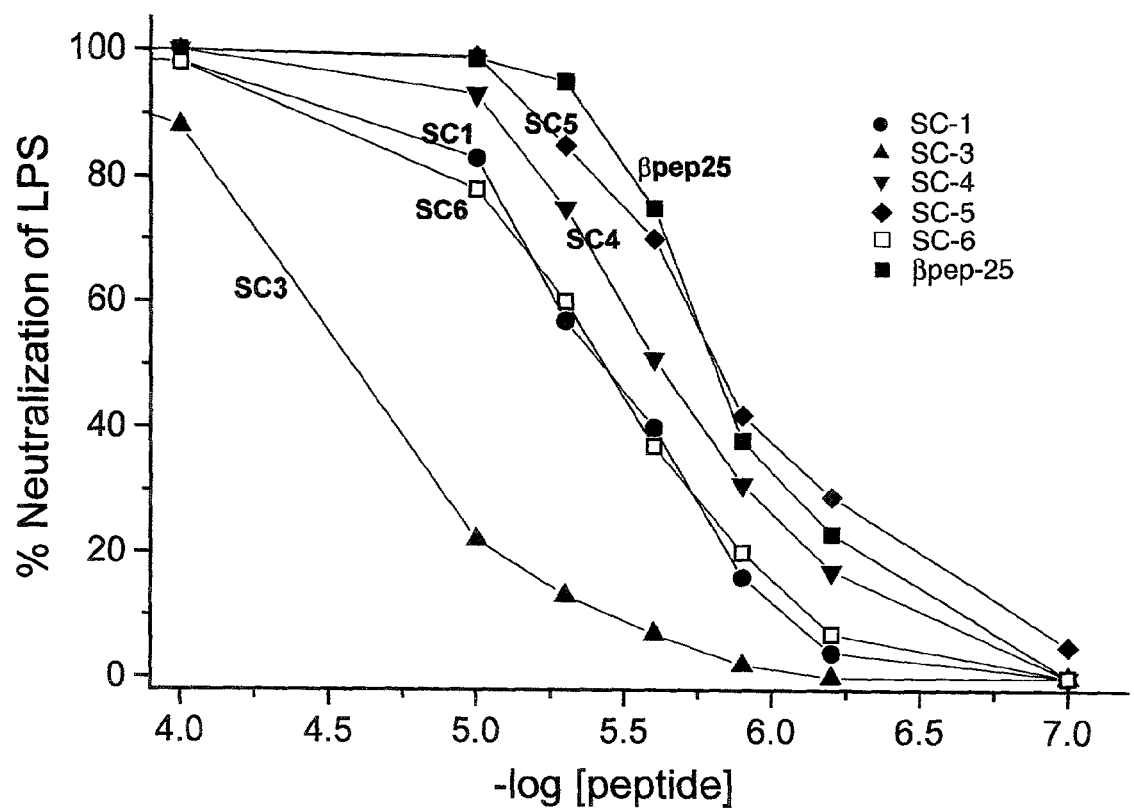
FIG. 3. Dose Response Curves for Endotoxin Neutralization. Dose response curves, as described in the Methods Section, are shown as percent LPS neutralization versus log concentration of peptide. The top panel illustrates results for SC peptides and for βpep-25, and the bottom panel illustrates results for various variants of SC-4 as described in the text.

The ability of these SC-4 variants to neutralize LPS was also investigated. Dose response curves are shown in FIG. 3 and IC50 values are listed in Table 4. As shown above, SC-401 and SC-402 are dodecapeptides which shift one residue each from SC-3 to SC-4, respectively. SC-4 has an IC50 of $2\times10^{-6}$ M, whereas SC-3 has an IC50 more than ten-fold greater ($25\times10^{-6}$ M). With a single residue shift from SC-3 towards SC-4, the activity of SC-401 (IC50 value of $126\times10^{-6}$ M) has dropped 5-fold relative to that of SC-3. Shifting one more residue to yield SC-402 brings the LPS neutralizing activity back to the level observed for SC-3 (IC50 of $25\times10^{-6}$ M). Comparison of these sequences indicates that it is apparently crucial to have at least one hydrophobic residue at the C-terminal position. SC-3 has Trp and SC-402 has Ile. Least active SC-401 ends in a Lys residue. The most active peptide SC-4 has the hydrophobic dipeptide Ile-Ile at its C-terminus. The exact functional significance is not clear since equipotent SC-5 has only one hydrophobic residue, Leu, at its C-terminus, whereas SC-1 has Phe, SC-2 has His, SC-6 has Gly, and inactive SC-7 also has a Leu.

In the lysine-to-norleucine variants, substitution of the first two Lys residues (K1X and K4X) reduces the activity only about 3-fold. Substitution of the last two Lys residues (K8X and K10X) has essentially no affect on the ability of the peptide to neutralize LPS. In this respect, no one of these lysines is crucial to this activity. A surprising finding, however, was observed with SC-408 and SC-409. SC-408 is the R5K variant. Here, the activity drops dramatically about 500-fold. Alone, this would suggest that the Arg residue is crucial to activity and charge conservation is insufficient to maintain activity. This conclusion, however, is challenged by results on SC-409 which has that Arg replaced with norleucine completely removing the positive charge, but maintain hydrophobic character from the side-chain methylenes. In SC-409, nearly full activity relative to that of SC-4, has been preserved. Therefore, a small positively charged amine group in that position is detrimental to activity, but the charge itself plays no apparent role in activity.

Discussion

Against bacteria investigated in this study, SC-4, with LD50 values falling in the single-digit nanomolar to 100 nanomolar range, is, overall, the most effective, antibacterial of any of these peptides. Aside from SC-7 and SC-8 which are inactive at concentrations below 10 micromolar, the other SC peptides, particularly SC-3 and SC-5, are reasonably bactericidal as well. In fact, against *S. aureus* strains MN8 and MNHO, activities for peptides SC-1 through SC-6 are within about a factor of two of each other, but against *E. coli* strain IA2, SC-4 stands out again, being about 4- to 10-fold more active than any other SC peptide. The observation that bactericidal peptides like SC-4 are more effective against Gram-negative strains as opposed to Gram-positives, is generally observed with other known bactericidal peptides. Differences in bactericidal activities against various strains are most likely due to variability in the components of the bacterial membranes and how these peptides interact with those membranes. For instance, the outer membrane surface of Gram-negative bacteria includes lipopolysaccharides, whereas in Gram-positive bacteria there is no outer membrane and the cell wall includes the acidic polysaccharides, teichoic acids. SC-4 must capture the appropriate compositional and structural features necessary for interactions with these mostly negatively charged cell surfaces in order to exhibit such broad spectrum bactericidal activity.

Relative to bacterial membranes, normal mammalian cell membranes which are composed predominatly of zwitterionic phosphotidyicholine and sphingomyelin phospholipids, have more positive charge character. Given the significant drop in the net negative charge of eukaryotic cell membrane surfaces, bactericidal peptides generally interact less with mammalian cells. Nonetheless, bactericidal peptides can lyse mammalian cells at concentrations near their bactericidal LD50 concentrations (Maloy et al., *Biopolymers* 37, 105–122 (1995)). In this respect, one must check that these concentration thresholds are not near one another in order to have the most effective and least cytotoxic, therapeutic bactericidal agent. Red blood cells are usually chosen as models for eukaryotic cells and hemolysis often is used as an index of a peptide's cytolytic activity against mammalian cells. For most SC peptides, significant hemolysis occurs only at concentrations above $1 \times 10^{-4}$ M, whereas LD50 values are all in the sub-micromolar to nanomolar ranges. This low cytotoxicity against mammalian cells is added advantage to using SC peptides as antibiotics.

Antibacterial peptides have been classified in a number of ways. One classification is based on chemical-structural criteria and is broken down into two broad groups: linear peptides and cyclic peptides. Within the linear group, two subgroups can be distinguished: (1) linear peptides tending to adopt helical structure and (2) linear peptides of unusual composition, rich in amino acids such as Pro, Arg or even Trp. Given the observation that SC peptides are helical, they are classified in the first subgroup. A list of other linear antibacterial peptides with helical conformation have been tabulated by Andreu & Rivas (Andreu et al., *Biopolymers (Pep. Sci.)* 47, 415–433 (1998)) (see Table I in Andreu et al., *Biopolymers (Pep. Sci.)* 47, 415–433 (1998)) and include: andropin, BLP-1, bombinin, bombolitin, the cecropins, ceratotoxin, clavanin, CRAMP, dermaseptin, enbocin, FALL-39, lycotoxin I, magainin, melittin, misgurin, PGLa, pleurocidin, seminalplasmin, and styelin. Conformations of peptides within this group are most often discussed as being α-helical which is a specific type of helix having 13 atoms or 3.6 residues per helical turn. However, it has been observed that many short linear peptides form a mixture of α-helix and $3_{10}$-helix in aqueous solution (Toniolo et al., *J. Am. Chem. Soc.* 118, 2744–2745 (1996); and Milihauser, *Biochemistry* 34, 3873–3877 (1995)). By reviewing structural data (mostly CD measurements) on other known helix-forming antibacterial peptides listed above, it is apparent that some of these peptides also have $3_{10}$ helix character as well. In this respect, the term "α-helical" as used currently in the literature may actually refer to both types of helix, i.e., the $3_{10}$ helix should not be excluded.

Both CD and NMR conformational analyses of SC peptides, especially of SC-4, show them to exist in aqueous solution as a mixture of α-helix, $3_{10}$ helix, and random coil. The degree of specific helix formation depends on the particular sequence and the presence or absence of TFE. With SC peptides, TFE does not appear to induce conformations that, to some extent, are already present in water. NOE patterns, for example, are essentially the same in water and in TFE. However, in TFE, NOEs are generally larger, indicating that TFE acts to stabilize existing conformations. Moreover, TFE also provides an environment of lower dielectric, which, in some ways, may mimic the low dielectric within a membrane. In terms of peptide folding, the presence of either type of helix is interesting because SC peptides were derived from βpep-25 which forms β-sheet structure in aqueous solution (Mayo et al., *Protein Sci.* 5, 1301–1315 (1996)). It appears, therefore, that when removed from the context of the entire βpep 33 mer, SC peptides are free to form helical structure. It has also been observed that bactericidal activity in βpep peptides is negatively correlated with β-sheet stability (Mayo et al., *Biochim. Biophys. Acta* 1425, 81–92 (1998)), i.e., more stable β-sheet leads to decreased bactericidal activity. Within the bacterial membrane, this may make conformational rearrangements for some βpep peptides, easier, thereby promoting greater bactericidal activity.

Based on NOE data, structural modeling shows SC-4 to be conformed as an amphipathic helix. For some time, amphipathic helical structure has been noted as being important for bactericidal activity. Even though the mechanism of action of bactericidal peptides is, for the most part, unclear, it has been shown that peptide-lipid, rather than receptor-mediated recognition processes, plays the major role in their function (Oren et al., *Biopolymers (Pep. Sci.)* 47, 451–463 (1998)). At least one antibacterial peptide: KLKLLLLLKLK$_{NH_2}$ (SEQ ID NO:20) effective only at a much higher concentration ($1 \times 10^{-4}$ M) than SC-4, has been shown to function by forming channels in bacterial membranes thereby increasing membrane permeability and interfering with function, ultimately resulting in cell death (Alvarez-Bravo et al., *J. Biochem.* 117, 1312–1316 (1995)). SC peptides probably function similarly since leakage kinetics occur on the same time scale with a half-kill time of about 10 min. Two mechanisms of action have been proposed to explain membrane permeation by amphipathic, helical peptides: (1) transmembrane pore formation via a "barrel-stave" mechanism (Ehrenstein et al., *Quart. Rev. Biophys.* 10, 1–34 (1977)) or (2) membrane destruction/solubilization via a "carpet-like" mechanism (Gazit et al., *Biochemistry* 34, 11479–11488 (1995); and Pouny et al., *Biochemistry* 31, 12416–12423 (1992)). In the generally favored "carpet-like" mechanism, amphipathic helical peptides interact with the bacterial membrane surface such that their hydrophobic surfaces face the membrane and their hydrophilic surfaces face the solvent. When a threshold concentration of peptide is reached, the membrane is disrupted and a transient pore is formed. From the present data, it is impossible to conclude definitively that SC peptides interact with cell membranes only when in a helical conformation. Nevertheless, when these peptides are conformed as amphipathic helices, their mechanism of action can be more readily explained.

The membrane surface of both Gram-positive and negative bacteria has a net negative charge making it a favorable environment for interaction with polycationic peptides like SC-4. In fact, Gray et al. (Gray et al., *Biochim. Biophys. Acta* 1244, 185–190 (1995)) showed that much of the bactericidal activity of the protein B/PI (bactericidal/permeability increasing protein) can be accounted for by the positively charged tripeptide sequence KWK. SC peptides, as well as the antibacterial peptide cecropins (Hanzawa et al., *FEBs Lett.* 269, 413–420 (1990)), also contain the KWK tripeptide motif. Relative to SC-4, however, their bactericidal activities against *P. aeruginosa* are much less with lethal concentrations, for example, of 6 micromolar for cecropin P1 (Lee et al., *Proc. Natl. Acad. Sci. USA* 86, 9159–9162 (1989)) compared to 10 nanomolar for SC-4. It is important to emphasize that a high net positive charge alone does not guarantee optimal bactericidal activity. For example, SC-4 and SC-5 both have a net charge of +6, even though SC-4 is the more potent of the two against Gram-negative bacteria. Furthermore, whereas SC-6 and SC-1 have net charges of only +3, SC-6 demonstrates about the same general bactericidal activity as SC-5, and SC-1 is at least as active as SC-4 against *E. coli* strain J96. The presence of hydrophobic residues also modulates bactericidal activity; yet hydrophobicity alone can also not account for these activity differences since hydrophobic residue content in each SC peptide is about 50% to 60%. Another mostly positively charged and hydrophobic, bactericidal peptide, derived from C-terminal amphipathic α-helix of platelet factor-4 (Darveau et al., *J. Clin. Invest.* 90, 447–455 (1992)), for example, has four lysine residues arrayed in tandem on one face of its helix; yet its activity is about 100 times less than that of SC-4.

Figure 7:
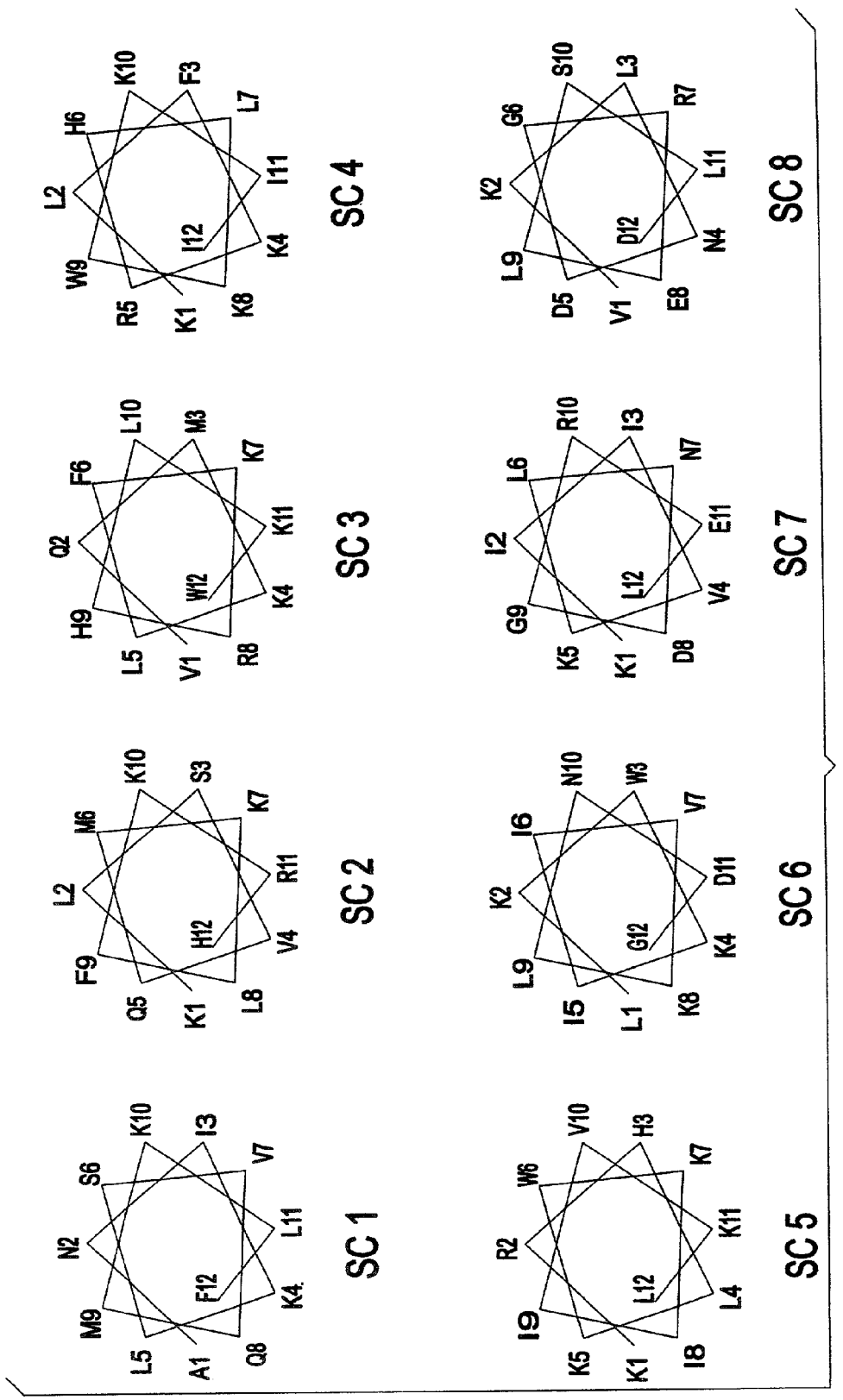
FIG. 7. Helical wheel projections for SC peptides. SC peptide sequences are shown in helical wheel projections as discussed in the text.

Clearly, both composition and sequence contribute to function. Amino acid sequence, in turn, determines conformation which ultimately is the key to understanding bactericidal effects from SC peptides and from other bactericidal peptides in general. In the case of SC-4, K1, K4, R5 and K8 are aligned on the same face of the helical molecule (see FIG. 6B). Since CD and NMR data indicate that the other SC peptides also have a propensity to form helical structure in aqueous solution and may as well promote their antibacterial activity when in a helical conformation, FIG. 7 shows helical wheel projections for SC-1 through SC-8. Note that the most active SC peptides, SC-3 and SC-4, have four positively charged residues aligned in tandem on one face of the helix. Moreover, in both cases, a lysine residue lies at the top of a diamond shaped array with an R-K pair in the middle and another K at the bottom of this array. For SC-4, the diamond shaped array is K1, R5-K4, K8, and for SC-3, the array is K4, R8-K 7, K11. In SC-4, this array starts at the first turn of the helix from the N-terminus, whereas in SC-3, it starts from the second turn of the helix. This may be the reason why SC-4 is overall more active than SC-3. In the next most active peptide, SC-5, residues K1-R2 and K5 on the helix surface form a triangle shape which is part of a diamond shape. In less active peptides SC-1, -2 and -6, positively charged residues are positioned throughout the helix, and in the least active, or non-active, peptides SC-7 and -8, lysine residues are few and interspersed with nega tively charged residues. Too much should not be made of this diamond shaped array in terms of anti-bacterial potency of SC peptides, since removal of any one of those positively charged residues form SC-4 does not reduce its activity to any great extent. Nevertheless, at least part of this charge distribution may be required for optimal activity.

Disintegration of the Gram-negative bactericidal cell outer membrane liberates the endotoxin lipopolysaccharide (LPS) which in mammalian white blood cells triggers the over release of various cytokines like TNFα and interleukin-1. This in turn can lead to the pathologic disorder of sepsis and possibly eventual death. SC-4 is one such bactericidal peptides which has the added advantage of being able to neutralize LPS. While the LPS binding activity (IC50) of SC-4 ($2\times10^{-6}$ M) is not as high as that of the 55 kD protein B/PI ($2\times10^{-8}$ M) (Marion et al., *FEBs Lett.* 227, 21–26 (1988)), SC-4 is afterall only a dodecapeptide. Mechanistically, the neutralization of LPS is thought to be mediated primarily by interactions between the protein/peptide and the lipid A portion of any given LPS. The nature of LPS varies from bacterial strain to strain; however all LPS molecules contain a conserved core unit lipid A which is composed of a diphosphorylated diglycosaminoglycan with a number of attached polyphosphorylated oligosaccharides and several acyl chains. LPS neutralization has been proposed to occur via protein/peptide binding to Lipid A both via cationic amino acid interactions with the anionic phosphates and via hydrophobic intertactions with the acyl chains. In the SC series, positive charge does play a role in LPS neutralization. SC-4 and SC-5 which have the highest net positive charge of +6 also neutralize LPS best. However, as with bactericidal activity, a high net positive charge alone can not account for LPS neutralization. Consider for example SC-2 and SC-3, which both have a net charge of +5; yet SC-3 is considerably more active than SC-2. Moreover, in the Arg/Lys-substituted norleucine series (Table 4), removal of any one positively charged residue drops LPS binding activity only slightly, probably indicating that the positive charge field itself rather than any one individual charged residue, mediates activity. On the other hand, hydrophobic residues at the C-terminus appear to be more crucial to LPS binding. Removal of the two isoleucines from the C-terminus of SC-4 (peptide SC-401) drops activity 60-fold, whereas removal of only one of these isoleucines (peptide SC-402) drops activity by only 12-fold. One curious finding is that while removal of R5 (SC-408) does not affect LPS binding, replacing R5 with lysine reduces LPS binding by some 500-fold.

CONCLUSION

Identification of a dodecapeptide with potent bactericidal activity against both Gram-positive and negative bacteria may lead to the development of a highly effective, therapeutic antibiotic and bacterial endotoxin neutralizing agent. Production and purification of bactericidal proteins or peptides with longer sequences present problems which in part can be avoid by the identification of a small peptide like SC-4. As new strains of antibiotic resistant bacteria continually emerge, such novel bactericidal agents will be particularly useful.

TABLE 5

```
REMARK      overall, bonds, angles, vdw, noe, cdih
REMARK energies: 80.52, 4.527, 30.51, 21.06, 10.3, 1.166, 12.96
REMARK========================================================
REMARK      bonds, angles, impropers, noe, cdih
REMARK rms-d: 4.2134E-03, 0.6535, 0.7938, 4.3271E-02, 0.9781
REMARK========================================================
REMARK      noe, cdih
REMARK violations.: 0, 0
ATOM    1   CA    LYS   1    13.611   -8.592    1.565   1.00   0.00   sc4
ATOM    2   HA    LYS   1    14.428   -9.138    2.008   1.00   0.00   sc4
ATOM    3   CB    LYS   1    13.338   -9.114    0.154   1.00   0.00   sc4
ATOM    4   HB1   LYS   1    14.076   -8.716   -0.526   1.00   0.00   sc4
ATOM    5   HB2   LYS   1    12.352   -8.803   -0.162   1.00   0.00   sc4
ATOM    6   CG    LYS   1    13.419  -10.642    0.150   1.00   0.00   sc4
ATOM    7   HG1   LYS   1    12.672  -11.040   -0.520   1.00   0.00   sc4
ATOM    8   HG2   LYS   1    13.242  -11.013    1.149   1.00   0.00   sc4
ATOM    9   CD    LYS   1    14.808  -11.079   -0.320   1.00   0.00   sc4
ATOM   10   HD1   LYS   1    15.520  -10.930    0.478   1.00   0.00   sc4
ATOM   11   HD2   LYS   1    15.098  -10.490   -1.178   1.00   0.00   sc4
ATOM   12   CE    LYS   1    14.775  -12.562   -0.703   1.00   0.00   sc4
ATOM   13   HE1   LYS   1    13.894  -12.780   -1.286   1.00   0.00   sc4
ATOM   14   HE2   LYS   1    14.801  -13.178    0.186   1.00   0.00   sc4
ATOM   15   NZ    LYS   1    16.000  -12.784   -1.527   1.00   0.00   sc4
ATOM   16   HZ1   LYS   1    16.650  -13.416   -1.017   1.00   0.00   sc4
ATOM   17   HZ2   LYS   1    16.472  -11.874   -1.707   1.00   0.00   sc4
ATOM   18   HZ3   LYS   1    15.734  -13.222   -2.431   1.00   0.00   sc4
ATOM   19   C     LYS   1    13.922   -7.094    1.533   1.00   0.00   sc4
ATOM   20   O     LYS   1    13.110   -6.273    1.912   1.00   0.00   sc4
ATOM   21   N     LYS   1    12.349   -8.841    2.321   1.00   0.00   sc4
ATOM   22   HT1   LYS   1    12.353   -9.810    2.696   1.00   0.00   sc4
ATOM   23   HT2   LYS   1    11.534   -8.717    1.686   1.00   0.00   sc4
ATOM   24   HT3   LYS   1    12.279   -8.167    3.111   1.00   0.00   sc4
ATOM   25   N     LEU   2    15.093   -6.731    1.084   1.00   0.00   sc4
ATOM   26   HN    LEU   2    15.734   -7.408    0.783   1.00   0.00   sc4
ATOM   27   CA    LEU   2    15.455   -5.285    1.027   1.00   0.00   sc4
ATOM   28   HA    LEU   2    15.225   -4.809    1.962   1.00   0.00   sc4
ATOM   29   CB    LEU   2    16.965   -5.261    0.787   1.00   0.00   sc4
ATOM   30   HB1   LEU   2    17.200   -4.521    0.037   1.00   0.00   sc4
ATOM   31   HB2   LEU   2    17.292   -6.234    0.450   1.00   0.00   sc4
ATOM   32   CG    LEU   2    17.677   -4.904    2.093   1.00   0.00   sc4
ATOM   33   HG    LEU   2    16.967   -4.469    2.781   1.00   0.00   sc4
ATOM   34   CD1   LEU   2    18.273   -6.169    2.712   1.00   0.00   sc4
ATOM   35   HD11  LEU   2    17.502   -6.707    3.244   1.00   0.00   sc4
ATOM   36   HD12  LEU   2    19.061   -5.898    3.398   1.00   0.00   sc4
ATOM   37   HD13  LEU   2    18.675   -6.797    1.931   1.00   0.00   sc4
ATOM   38   CD2   LEU   2    18.797   -3.901    1.808   1.00   0.00   sc4
ATOM   39   HD21  LEU   2    19.638   -4.109    2.453   1.00   0.00   sc4
ATOM   40   HD22  LEU   2    18.439   -2.899    1.995   1.00   0.00   sc4
ATOM   41   HD23  LEU   2    19.104   -3.987    0.777   1.00   0.00   sc4
ATOM   42   C     LEU   2    14.710   -4.604   -0.127   1.00   0.00   sc4
ATOM   43   O     LEU   2    14.647   -3.394   -0.218   1.00   0.00   sc4
ATOM   44   N     PHE   3    14.152   -5.384   -1.010   1.00   0.00   sc4
ATOM   45   HN    PHE   3    14.226   -6.356   -0.909   1.00   0.00   sc4
ATOM   46   CA    PHE   3    13.409   -4.818   -2.176   1.00   0.00   sc4
ATOM   47   HA    PHE   3    14.088   -4.304   -2.836   1.00   0.00   sc4
ATOM   48   CB    PHE   3    12.820   -6.034   -2.891   1.00   0.00   sc4
ATOM   49   HB1   PHE   3    11.884   -5.758   -3.355   1.00   0.00   sc4
ATOM   50   HB2   PHE   3    12.648   -6.824   -2.176   1.00   0.00   sc4
ATOM   51   CG    PHE   3    13.781   -6.513   -3.951   1.00   0.00   sc4
ATOM   52   CD1   PHE   3    14.143   -7.864   -4.006   1.00   0.00   sc4
ATOM   53   HD1   PHE   3    13.734   -8.562   -3.289   1.00   0.00   sc4
ATOM   54   CD2   PHE   3    14.310   -5.608   -4.880   1.00   0.00   sc4
ATOM   55   HD2   PHE   3    14.031   -4.566   -4.837   1.00   0.00   sc4
ATOM   56   CE1   PHE   3    15.033   -8.311   -4.989   1.00   0.00   sc4
ATOM   57   HE1   PHE   3    15.312   -9.353   -5.032   1.00   0.00   sc4
ATOM   58   CE2   PHE   3    15.200   -6.055   -5.863   1.00   0.00   sc4
ATOM   59   HE2   PHE   3    15.608   -5.358   -6.579   1.00   0.00   sc4
ATOM   60   CZ    PHE   3    15.562   -7.406   -5.918   1.00   0.00   sc4
ATOM   61   HZ    PHE   3    16.248   -7.751   -6.676   1.00   0.00   sc4
ATOM   62   C     PHE   3    12.284   -3.875   -1.728   1.00   0.00   sc4
ATOM   63   O     PHE   3    11.703   -3.179   -2.533   1.00   0.00   sc4
ATOM   64   N     LYS   4    11.940   -3.865   -0.470   1.00   0.00   sc4
ATOM   65   HN    LYS   4    12.395   -4.451    0.172   1.00   0.00   sc4
ATOM   66   CA    LYS   4    10.822   -2.978   -0.020   1.00   0.00   sc4
ATOM   67   HA    LYS   4    10.265   -2.626   -0.873   1.00   0.00   sc4
ATOM   68   CB    LYS   4     9.929   -3.881    0.834   1.00   0.00   sc4
ATOM   69   HB1   LYS   4     9.816   -4.838    0.346   1.00   0.00   sc4
ATOM   70   HB2   LYS   4     8.960   -3.420    0.951   1.00   0.00   sc4
ATOM   71   CG    LYS   4    10.567   -4.087    2.210   1.00   0.00   sc4
```

TABLE 5-continued

| ATOM | 72 | HG1 | LYS | 4 | 10.237 | −3.307 | 2.880 | 1.00 | 0.00 | sc4 |
| --- | --- | --- | --- | --- | --- | --- | --- | --- | --- | --- |
| ATOM | 73 | HG2 | LYS | 4 | 11.643 | −4.050 | 2.117 | 1.00 | 0.00 | sc4 |
| ATOM | 74 | CD | LYS | 4 | 10.149 | −5.448 | 2.770 | 1.00 | 0.00 | sc4 |
| ATOM | 75 | HD1 | LYS | 4 | 10.938 | −5.839 | 3.393 | 1.00 | 0.00 | sc4 |
| ATOM | 76 | HD2 | LYS | 4 | 9.962 | −6.130 | 1.953 | 1.00 | 0.00 | sc4 |
| ATOM | 77 | CE | LYS | 4 | 8.875 | −5.289 | 3.605 | 1.00 | 0.00 | sc4 |
| ATOM | 78 | HE1 | LYS | 4 | 8.540 | −6.249 | 3.966 | 1.00 | 0.00 | sc4 |
| ATOM | 79 | HE2 | LYS | 4 | 8.100 | −4.816 | 3.019 | 1.00 | 0.00 | sc4 |
| ATOM | 80 | NZ | LYS | 4 | 9.263 | −4.420 | 4.754 | 1.00 | 0.00 | sc4 |
| ATOM | 81 | HZ1 | LYS | 4 | 10.220 | −4.042 | 4.601 | 1.00 | 0.00 | sc4 |
| ATOM | 82 | HZ2 | LYS | 4 | 9.247 | −4.980 | 5.632 | 1.00 | 0.00 | sc4 |
| ATOM | 83 | HZ3 | LYS | 4 | 8.590 | −3.632 | 4.834 | 1.00 | 0.00 | sc4 |
| ATOM | 84 | C | LYS | 4 | 11.329 | −1.786 | 0.808 | 1.00 | 0.00 | sc4 |
| ATOM | 85 | O | LYS | 4 | 10.594 | −0.854 | 1.070 | 1.00 | 0.00 | sc4 |
| ATOM | 86 | N | ARG | 5 | 12.555 | −1.813 | 1.251 | 1.00 | 0.00 | sc4 |
| ATOM | 87 | HN | ARG | 5 | 13.131 | −2.581 | 1.054 | 1.00 | 0.00 | sc4 |
| ATOM | 88 | CA | ARG | 5 | 13.067 | −0.685 | 2.092 | 1.00 | 0.00 | sc4 |
| ATOM | 89 | HA | ARG | 5 | 12.383 | −0.495 | 2.900 | 1.00 | 0.00 | sc4 |
| ATOM | 90 | CB | ARG | 5 | 14.384 | −1.207 | 2.658 | 1.00 | 0.00 | sc4 |
| ATOM | 91 | HB1 | ARG | 5 | 14.723 | −0.560 | 3.452 | 1.00 | 0.00 | sc4 |
| ATOM | 92 | HB2 | ARG | 5 | 15.128 | −1.249 | 1.878 | 1.00 | 0.00 | sc4 |
| ATOM | 93 | CG | ARG | 5 | 14.151 | −2.608 | 3.207 | 1.00 | 0.00 | sc4 |
| ATOM | 94 | HG1 | ARG | 5 | 14.374 | −3.328 | 2.439 | 1.00 | 0.00 | sc4 |
| ATOM | 95 | HG2 | ARG | 5 | 13.115 | −2.707 | 3.500 | 1.00 | 0.00 | sc4 |
| ATOM | 96 | CD | ARG | 5 | 15.055 | −2.847 | 4.417 | 1.00 | 0.00 | sc4 |
| ATOM | 97 | HD1 | ARG | 5 | 15.710 | −2.004 | 4.571 | 1.00 | 0.00 | sc4 |
| ATOM | 98 | HD2 | ARG | 5 | 15.628 | −3.755 | 4.284 | 1.00 | 0.00 | sc4 |
| ATOM | 99 | NE | ARG | 5 | 14.120 | −2.983 | 5.569 | 1.00 | 0.00 | sc4 |
| ATOM | 100 | HE | ARG | 5 | 13.215 | −2.612 | 5.510 | 1.00 | 0.00 | sc4 |
| ATOM | 101 | CZ | ARG | 5 | 14.505 | −3.594 | 6.655 | 1.00 | 0.00 | sc4 |
| ATOM | 102 | NH1 | ARG | 5 | 14.788 | −2.904 | 7.725 | 1.00 | 0.00 | sc4 |
| ATOM | 103 | HH11 | ARG | 5 | 14.709 | −1.907 | 7.712 | 1.00 | 0.00 | sc4 |
| ATOM | 104 | HH12 | ARG | 5 | 15.081 | −3.371 | 8.559 | 1.00 | 0.00 | sc4 |
| ATOM | 105 | NH2 | ARG | 5 | 14.607 | −4.895 | 6.671 | 1.00 | 0.00 | sc4 |
| ATOM | 106 | HH21 | ARG | 5 | 14.391 | −5.424 | 5.851 | 1.00 | 0.00 | sc4 |
| ATOM | 107 | HH22 | ARG | 5 | 14.901 | −5.363 | 7.505 | 1.00 | 0.00 | sc4 |
| ATOM | 108 | C | ARG | 5 | 13.272 | 0.597 | 1.270 | 1.00 | 0.00 | sc4 |
| ATOM | 109 | O | ARG | 5 | 12.386 | 1.412 | 1.196 | 1.00 | 0.00 | sc4 |
| ATOM | 110 | N | HIS | 6 | 14.425 | 0.764 | 0.660 | 1.00 | 0.00 | sc4 |
| ATOM | 111 | HN | HIS | 6 | 15.110 | 0.074 | 0.745 | 1.00 | 0.00 | sc4 |
| ATOM | 112 | CA | HIS | 6 | 14.730 | 1.987 | −0.178 | 1.00 | 0.00 | sc4 |
| ATOM | 113 | HA | HIS | 6 | 15.325 | 2.691 | 0.378 | 1.00 | 0.00 | sc4 |
| ATOM | 114 | CB | HIS | 6 | 15.548 | 1.424 | −1.346 | 1.00 | 0.00 | sc4 |
| ATOM | 115 | HB1 | HIS | 6 | 16.549 | 1.192 | −1.016 | 1.00 | 0.00 | sc4 |
| ATOM | 116 | HB2 | HIS | 6 | 15.583 | 2.145 | −2.150 | 1.00 | 0.00 | sc4 |
| ATOM | 117 | CG | HIS | 6 | 14.865 | 0.172 | −1.810 | 1.00 | 0.00 | sc4 |
| ATOM | 118 | ND1 | HIS | 6 | 13.686 | 0.218 | −2.528 | 1.00 | 0.00 | sc4 |
| ATOM | 119 | HD1 | HIS | 6 | 13.262 | 1.022 | −2.896 | 1.00 | 0.00 | sc4 |
| ATOM | 120 | CD2 | HIS | 6 | 15.091 | −1.151 | −1.538 | 1.00 | 0.00 | sc4 |
| ATOM | 121 | HD2 | HIS | 6 | 15.930 | −1.538 | −0.981 | 1.00 | 0.00 | sc4 |
| ATOM | 122 | CE1 | HIS | 6 | 13.233 | −1.037 | −2.642 | 1.00 | 0.00 | sc4 |
| ATOM | 123 | HE1 | HIS | 6 | 12.279 | −1.290 | −3.065 | 1.00 | 0.00 | sc4 |
| ATOM | 124 | NE2 | HIS | 6 | 14.057 | −1.917 | −2.065 | 1.00 | 0.00 | sc4 |
| ATOM | 125 | C | HIS | 6 | 13.458 | 2.659 | −0.725 | 1.00 | 0.00 | sc4 |
| ATOM | 126 | O | HIS | 6 | 13.390 | 3.863 | −0.859 | 1.00 | 0.00 | sc4 |
| ATOM | 127 | N | LEU | 7 | 12.467 | 1.879 | −1.047 | 1.00 | 0.00 | sc4 |
| ATOM | 128 | HN | LEU | 7 | 12.560 | 0.914 | −0.922 | 1.00 | 0.00 | sc4 |
| ATOM | 129 | CA | LEU | 7 | 11.188 | 2.415 | −1.599 | 1.00 | 0.00 | sc4 |
| ATOM | 130 | HA | LEU | 7 | 11.212 | 2.421 | −2.672 | 1.00 | 0.00 | sc4 |
| ATOM | 131 | CB | LEU | 7 | 10.144 | 1.411 | −1.113 | 1.00 | 0.00 | sc4 |
| ATOM | 132 | HB1 | LEU | 7 | 10.053 | 1.483 | −0.039 | 1.00 | 0.00 | sc4 |
| ATOM | 133 | HB2 | LEU | 7 | 10.461 | 0.412 | −1.376 | 1.00 | 0.00 | sc4 |
| ATOM | 134 | CG | LEU | 7 | 8.785 | 1.693 | −1.753 | 1.00 | 0.00 | sc4 |
| ATOM | 135 | HG | LEU | 7 | 8.925 | 2.078 | −2.753 | 1.00 | 0.00 | sc4 |
| ATOM | 136 | CD1 | LEU | 7 | 8.000 | 0.387 | −1.811 | 1.00 | 0.00 | sc4 |
| ATOM | 137 | HD11 | LEU | 7 | 7.764 | 0.152 | −2.836 | 1.00 | 0.00 | sc4 |
| ATOM | 138 | HD12 | LEU | 7 | 7.088 | 0.493 | −1.242 | 1.00 | 0.00 | sc4 |
| ATOM | 139 | HD13 | LEU | 7 | 8.598 | −0.407 | −1.386 | 1.00 | 0.00 | sc4 |
| ATOM | 140 | CD2 | LEU | 7 | 8.001 | 2.705 | −0.909 | 1.00 | 0.00 | sc4 |
| ATOM | 141 | HD21 | LEU | 7 | 7.719 | 2.248 | 0.029 | 1.00 | 0.00 | sc4 |
| ATOM | 142 | HD22 | LEU | 7 | 7.113 | 3.008 | −1.440 | 1.00 | 0.00 | sc4 |
| ATOM | 143 | HD23 | LEU | 7 | 8.612 | 3.572 | −0.714 | 1.00 | 0.00 | sc4 |
| ATOM | 144 | C | LEU | 7 | 10.847 | 3.806 | −1.063 | 1.00 | 0.00 | sc4 |
| ATOM | 145 | O | LEU | 7 | 10.687 | 4.753 | −1.807 | 1.00 | 0.00 | sc4 |
| ATOM | 146 | N | LYS | 8 | 10.679 | 3.914 | 0.218 | 1.00 | 0.00 | sc4 |
| ATOM | 147 | HN | LYS | 8 | 10.779 | 3.123 | 0.787 | 1.00 | 0.00 | sc4 |
| ATOM | 148 | CA | LYS | 8 | 10.281 | 5.216 | 0.826 | 1.00 | 0.00 | sc4 |
| ATOM | 149 | HA | LYS | 8 | 9.612 | 5.747 | 0.176 | 1.00 | 0.00 | sc4 |
| ATOM | 150 | CB | LYS | 8 | 9.546 | 4.833 | 2.119 | 1.00 | 0.00 | sc4 |

TABLE 5-continued

| ATOM | 151 | HB1 | LYS | 8 | 8.955 | 5.672 | 2.453 | 1.00 | 0.00 | sc4 |
| --- | --- | --- | --- | --- | --- | --- | --- | --- | --- | --- |
| ATOM | 152 | HB2 | LYS | 8 | 10.270 | 4.583 | 2.879 | 1.00 | 0.00 | sc4 |
| ATOM | 153 | CG | LYS | 8 | 8.622 | 3.626 | 1.883 | 1.00 | 0.00 | sc4 |
| ATOM | 154 | HG1 | LYS | 8 | 8.542 | 3.052 | 2.793 | 1.00 | 0.00 | sc4 |
| ATOM | 155 | HG2 | LYS | 8 | 9.024 | 2.996 | 1.107 | 1.00 | 0.00 | sc4 |
| ATOM | 156 | CD | LYS | 8 | 7.234 | 4.123 | 1.476 | 1.00 | 0.00 | sc4 |
| ATOM | 157 | HD1 | LYS | 8 | 6.568 | 3.282 | 1.363 | 1.00 | 0.00 | sc4 |
| ATOM | 158 | HD2 | LYS | 8 | 7.305 | 4.657 | 0.539 | 1.00 | 0.00 | sc4 |
| ATOM | 159 | CE | LYS | 8 | 6.693 | 5.059 | 2.559 | 1.00 | 0.00 | sc4 |
| ATOM | 160 | HE1 | LYS | 8 | 6.609 | 6.065 | 2.180 | 1.00 | 0.00 | sc4 |
| ATOM | 161 | HE2 | LYS | 8 | 7.334 | 5.034 | 3.430 | 1.00 | 0.00 | sc4 |
| ATOM | 162 | NZ | LYS | 8 | 5.343 | 4.524 | 2.892 | 1.00 | 0.00 | sc4 |
| ATOM | 163 | HZ1 | LYS | 8 | 5.418 | 3.870 | 3.696 | 1.00 | 0.00 | sc4 |
| ATOM | 164 | HZ2 | LYS | 8 | 4.958 | 4.019 | 2.067 | 1.00 | 0.00 | sc4 |
| ATOM | 165 | HZ3 | LYS | 8 | 4.711 | 5.309 | 3.145 | 1.00 | 0.00 | sc4 |
| ATOM | 166 | C | LYS | 8 | 11.505 | 6.066 | 1.160 | 1.00 | 0.00 | sc4 |
| ATOM | 167 | O | LYS | 8 | 11.613 | 7.219 | 0.797 | 1.00 | 0.00 | sc4 |
| ATOM | 168 | N | TRP | 9 | 12.406 | 5.484 | 1.878 | 1.00 | 0.00 | sc4 |
| ATOM | 169 | HN | TRP | 9 | 12.266 | 4.583 | 2.138 | 1.00 | 0.00 | sc4 |
| ATOM | 170 | CA | TRP | 9 | 13.632 | 6.182 | 2.314 | 1.00 | 0.00 | sc4 |
| ATOM | 171 | HA | TRP | 9 | 13.361 | 6.996 | 2.960 | 1.00 | 0.00 | sc4 |
| ATOM | 172 | CB | TRP | 9 | 14.406 | 5.130 | 3.126 | 1.00 | 0.00 | sc4 |
| ATOM | 173 | HB1 | TRP | 9 | 15.330 | 5.553 | 3.491 | 1.00 | 0.00 | sc4 |
| ATOM | 174 | HB2 | TRP | 9 | 14.611 | 4.266 | 2.510 | 1.00 | 0.00 | sc4 |
| ATOM | 175 | CG | TRP | 9 | 13.533 | 4.744 | 4.283 | 1.00 | 0.00 | sc4 |
| ATOM | 176 | CD1 | TRP | 9 | 13.600 | 5.265 | 5.531 | 1.00 | 0.00 | sc4 |
| ATOM | 177 | HD1 | TRP | 9 | 14.318 | 5.996 | 5.870 | 1.00 | 0.00 | sc4 |
| ATOM | 178 | CD2 | TRP | 9 | 12.425 | 3.802 | 4.295 | 1.00 | 0.00 | sc4 |
| ATOM | 179 | NE1 | TRP | 9 | 12.588 | 4.709 | 6.300 | 1.00 | 0.00 | sc4 |
| ATOM | 180 | HE1 | TRP | 9 | 12.410 | 4.922 | 7.240 | 1.00 | 0.00 | sc4 |
| ATOM | 181 | CE2 | TRP | 9 | 11.837 | 3.803 | 5.575 | 1.00 | 0.00 | sc4 |
| ATOM | 182 | CE3 | TRP | 9 | 11.878 | 2.961 | 3.316 | 1.00 | 0.00 | sc4 |
| ATOM | 183 | HE3 | TRP | 9 | 12.318 | 2.938 | 2.339 | 1.00 | 0.00 | sc4 |
| ATOM | 184 | CZ2 | TRP | 9 | 10.734 | 2.997 | 5.862 | 1.00 | 0.00 | sc4 |
| ATOM | 185 | HZ2 | TRP | 9 | 10.289 | 3.010 | 6.846 | 1.00 | 0.00 | sc4 |
| ATOM | 186 | CZ3 | TRP | 9 | 10.780 | 2.161 | 3.593 | 1.00 | 0.00 | sc4 |
| ATOM | 187 | HZ3 | TRP | 9 | 10.367 | 1.527 | 2.822 | 1.00 | 0.00 | sc4 |
| ATOM | 188 | CH2 | TRP | 9 | 10.206 | 2.178 | 4.856 | 1.00 | 0.00 | sc4 |
| ATOM | 189 | HH2 | TRP | 9 | 9.351 | 1.576 | 5.044 | 1.00 | 0.00 | sc4 |
| ATOM | 190 | C | TRP | 9 | 14.404 | 6.695 | 1.099 | 1.00 | 0.00 | sc4 |
| ATOM | 191 | O | TRP | 9 | 15.281 | 7.528 | 1.216 | 1.00 | 0.00 | sc4 |
| ATOM | 192 | N | LYS | 10 | 14.065 | 6.227 | −0.076 | 1.00 | 0.00 | sc4 |
| ATOM | 193 | HN | LYS | 10 | 13.338 | 5.567 | −0.160 | 1.00 | 0.00 | sc4 |
| ATOM | 194 | CA | LYS | 10 | 14.768 | 6.724 | −1.292 | 1.00 | 0.00 | sc4 |
| ATOM | 195 | HA | LYS | 10 | 15.833 | 6.602 | −1.191 | 1.00 | 0.00 | sc4 |
| ATOM | 196 | CB | LYS | 10 | 14.242 | 5.871 | −2.449 | 1.00 | 0.00 | sc4 |
| ATOM | 197 | HB1 | LYS | 10 | 14.134 | 6.489 | −3.328 | 1.00 | 0.00 | sc4 |
| ATOM | 198 | HB2 | LYS | 10 | 13.282 | 5.456 | −2.183 | 1.00 | 0.00 | sc4 |
| ATOM | 199 | CG | LYS | 10 | 15.227 | 4.739 | −2.746 | 1.00 | 0.00 | sc4 |
| ATOM | 200 | HG1 | LYS | 10 | 14.775 | 3.793 | −2.492 | 1.00 | 0.00 | sc4 |
| ATOM | 201 | HG2 | LYS | 10 | 16.124 | 4.879 | −2.159 | 1.00 | 0.00 | sc4 |
| ATOM | 202 | CD | LYS | 10 | 15.583 | 4.749 | −4.235 | 1.00 | 0.00 | sc4 |
| ATOM | 203 | HD1 | LYS | 10 | 16.653 | 4.663 | −4.351 | 1.00 | 0.00 | sc4 |
| ATOM | 204 | HD2 | LYS | 10 | 15.246 | 5.675 | −4.679 | 1.00 | 0.00 | sc4 |
| ATOM | 205 | CE | LYS | 10 | 14.901 | 3.569 | −4.934 | 1.00 | 0.00 | sc4 |
| ATOM | 206 | HE1 | LYS | 10 | 13.857 | 3.783 | −5.100 | 1.00 | 0.00 | sc4 |
| ATOM | 207 | HE2 | LYS | 10 | 15.014 | 2.669 | −4.345 | 1.00 | 0.00 | sc4 |
| ATOM | 208 | NZ | LYS | 10 | 15.607 | 3.430 | −6.239 | 1.00 | 0.00 | sc4 |
| ATOM | 209 | HZ1 | LYS | 10 | 15.064 | 3.914 | −6.981 | 1.00 | 0.00 | sc4 |
| ATOM | 210 | HZ2 | LYS | 10 | 15.698 | 2.421 | −6.478 | 1.00 | 0.00 | sc4 |
| ATOM | 211 | HZ3 | LYS | 10 | 16.552 | 3.857 | −6.170 | 1.00 | 0.00 | sc4 |
| ATOM | 212 | C | LYS | 10 | 14.411 | 8.195 | −1.519 | 1.00 | 0.00 | sc4 |
| ATOM | 213 | O | LYS | 10 | 15.268 | 9.028 | −1.739 | 1.00 | 0.00 | sc4 |
| ATOM | 214 | N | ILE | 11 | 13.145 | 8.516 | −1.469 | 1.00 | 0.00 | sc4 |
| ATOM | 215 | HN | ILE | 11 | 12.473 | 7.825 | −1.292 | 1.00 | 0.00 | sc4 |
| ATOM | 216 | CA | ILE | 11 | 12.720 | 9.929 | −1.683 | 1.00 | 0.00 | sc4 |
| ATOM | 217 | HA | ILE | 11 | 13.562 | 10.533 | −1.982 | 1.00 | 0.00 | sc4 |
| ATOM | 218 | CB | ILE | 11 | 11.699 | 9.862 | −2.819 | 1.00 | 0.00 | sc4 |
| ATOM | 219 | KB | ILE | 11 | 10.976 | 9.088 | −2.606 | 1.00 | 0.00 | sc4 |
| ATOM | 220 | CG1 | ILE | 11 | 12.417 | 9.545 | −4.133 | 1.00 | 0.00 | sc4 |
| ATOM | 221 | HG11 | ILE | 11 | 11.689 | 9.303 | −4.892 | 1.00 | 0.00 | sc4 |
| ATOM | 222 | HG12 | ILE | 11 | 13.079 | 8.704 | −3.987 | 1.00 | 0.00 | sc4 |
| ATOM | 223 | CG2 | ILE | 11 | 10.982 | 11.208 | −2.943 | 1.00 | 0.00 | sc4 |
| ATOM | 224 | HG21 | ILE | 11 | 10.009 | 11.142 | −2.478 | 1.00 | 0.00 | sc4 |
| ATOM | 225 | HG22 | ILE | 11 | 10.865 | 11.459 | −3.987 | 1.00 | 0.00 | sc4 |
| ATOM | 226 | HG23 | ILE | 11 | 11.564 | 11.973 | −2.45 1 | 1.00 | 0.00 | sc4 |
| ATOM | 227 | CD1 | ILE | 11 | 13.230 | 10.762 | −4.579 | 1.00 | 0.00 | sc4 |
| ATOM | 228 | HD11 | ILE | 11 | 13.810 | 10.507 | −5.454 | 1.00 | 0.00 | sc4 |
| ATOM | 229 | HD12 | ILE | 11 | 13.893 | 11.064 | −3.783 | 1.00 | 0.00 | sc4 |

TABLE 5-continued

| ATOM | 230 | HD13 | ILE | 11 | 12.560 | 11.575 | −4.817 | 1.00 | 0.00 | sc4 |
|---|---|---|---|---|---|---|---|---|---|---|
| ATOM | 231 | C | ILE | 11 | 12.074 | 10.502 | −0.415 | 1.00 | 0.00 | sc4 |
| ATOM | 232 | O | ILE | 11 | 11.955 | 11.701 | −0.262 | 1.00 | 0.00 | sc4 |
| ATOM | 233 | N | ILE | 12 | 11.647 | 9.661 | 0.493 | 1.00 | 0.00 | sc4 |
| ATOM | 234 | HN | ILE | 12 | 11.746 | 8.695 | 0.355 | 1.00 | 0.00 | sc4 |
| ATOM | 235 | CA | ILE | 12 | 11.002 | 10.182 | 1.738 | 1.00 | 0.00 | sc4 |
| ATOM | 236 | HA | ILE | 12 | 10.216 | 10.875 | 1.483 | 1.00 | 0.00 | sc4 |
| ATOM | 237 | CB | ILE | 12 | 10.400 | 8.952 | 2.436 | 1.00 | 0.00 | sc4 |
| ATOM | 238 | HB | ILE | 12 | 10.048 | 8.255 | 1.691 | 1.00 | 0.00 | sc4 |
| ATOM | 239 | CG1 | ILE | 12 | 9.225 | 9.389 | 3.313 | 1.00 | 0.00 | sc4 |
| ATOM | 240 | HG11 | ILE | 12 | 8.439 | 9.789 | 2.690 | 1.00 | 0.00 | sc4 |
| ATOM | 241 | HG12 | ILE | 12 | 9.556 | 10.147 | 4.008 | 1.00 | 0.00 | sc4 |
| ATOM | 242 | CG2 | ILE | 12 | 11.450 | 8.267 | 3.315 | 1.00 | 0.00 | sc4 |
| ATOM | 243 | HG21 | ILE | 12 | 11.272 | 8.519 | 4.350 | 1.00 | 0.00 | sc4 |
| ATOM | 244 | HG22 | ILE | 12 | 12.435 | 8.602 | 3.028 | 1.00 | 0.00 | sc4 |
| ATOM | 245 | HG23 | ILE | 12 | 11.382 | 7.196 | 3.191 | 1.00 | 0.00 | sc4 |
| ATOM | 246 | CD1 | ILE | 12 | 8.692 | 8.182 | 4.088 | 1.00 | 0.00 | sc4 |
| ATOM | 247 | HD11 | ILE | 12 | 9.097 | 7.275 | 3.665 | 1.00 | 0.00 | sc4 |
| ATOM | 248 | HD12 | ILE | 12 | 7.614 | 8.160 | 4.024 | 1.00 | 0.00 | sc4 |
| ATOM | 249 | HD13 | ILE | 12 | 8.989 | 8.260 | 5.124 | 1.00 | 0.00 | sc4 |
| ATOM | 250 | C | ILE | 12 | 12.043 | 10.874 | 2.627 | 1.00 | 0.00 | sc4 |
| ATOM | 251 | OT1 | ILE | 12 | 11.650 | 11.710 | 3.425 | 1.00 | 0.00 | sc4 |
| ATOM | 252 | OT2 | ILE | 12 | 13.213 | 10.557 | 2.492 | 1.00 | 0.00 | sc4 |

TABLE 6 assign (resid 2 and name HN) (resid 1 and name HA) 1.8 0 4.0
assign (resid 3 and name HN) (resid 2 and name HA) 1.8 0 2.5
assign (resid 3 and name HN) (resid 4 and name HA) 1.8 0 4.0
assign (resid 3 and name HN) (resid 3 and name HB1) 1.8 0 3.0
assign (resid 3 and name HN) (resid 3 and name HB2) 1.8 0 3.0
assign (resid 3 and name HN) (resid 4 and name HG*) 1.8 0 5.0
assign (resid 3 and name HN) (resid 4 and name HD*) 1.8 0 5.0
assign (resid 3 and name HN) (resid 2 and name HB*) 1.8 0 3.5
assign (resid 3 and name HN) (resid 2 and name HD*) 1.8 0 4.5
assign (resid 4 and name HN) (resid 3 and name HA) 1.8 0 3.0
assign (resid 4 and name HN) (resid 2 and name HA) 1.8 0 4.0
assign (resid 4 and name HN) (resid 3 and name HB1) 1.8 0 3.0
assign (resid 4 and name HN) (resid 3 and name HB2) 1.8 0 3.0
assign (resid 4 and name HN) (resid 5 and name HB*) 1.8 0 3.5
assign (resid 4 and name HN) (resid 5 and name HG*) 1.8 0 3.5
assign (resid 4 and name HN) (resid 4 and name HB*) 1.8 0 3.0
assign (resid 4 and name HN) (resid 4 and name HG*) 1.8 0 3.5
assign (resid 4 and name HN) (resid 4 and name HD*) 1.8 0 3.5
assign (resid 5 and name HN) (resid 4 and name HA) 1.8 0 3.0
assign (resid 5 and name HN) (resid 5 and name HB*) 1.8 0 3.0
assign (resid 5 and name HN) (resid 5 and name HG*) 1.8 0 3.5
assign (resid 5 and name HN) (resid 5 and name HD*) 1.8 0 3.5
assign (resid 5 and name HN) (resid 2 and name HA) 1.8 0 4.0
assign (resid 5 and name HN) (resid 2 and name CO) 1.8 0 3.0
assign (resid 5 and name HN) (resid 1 and name CO) 1.8 0 3.0
assign (resid 6 and name HN) (resid 5 and name HA) 1.8 0 3.0
assign (resid 6 and name HN) (resid 6 and name HB*) 1.8 0 3.0
assign (resid 6 and name HN) (resid 5 and name HB*) 1.8 0 3.5
assign (resid 6 and name HN) (resid 5 and name HG*) 1.8 0 3.5
assign (resid 6 and name HE1) (resid 6 and name HA) 1.8 0 5.0
assign (resid 6 and name HE1) (resid 5 and name HA) 1.8 0 5.5
assign (resid 6 and name HE1) (resid 6 and name HB*) 1.8 0 5.5
assign (resid 6 and name HE1) (resid 5 and name HB*) 1.8 0 4.5
assign (resid 6 and name HE1) (resid S and name HG*) 1.8 0 4.5
assign (resid 6 and name HE1) (resid 8 and name HG*) 1.8 0 5.5
assign (resid 6 and name HD2) (resid 6 and name HB*) 1.8 0 3.3
assign (resid 6 and name HD2) (resid 5 and name HA) 1.8 0 3.5
assign (resid 6 and name HD2) (resid 3 and name HG*) 1.8 0 5.5
assign (resid 6 and name HN) (resid 2 and name CO) 1.8 0 3.0
assign (resid 6 and name HN) (resid 3 and name CO) 1.8 0 3.0
assign (resid 7 and name HN) (resid 6 and name HA) 1.8 0 3.0
assign (resid 7 and name HN) (resid 5 and name HA) 1.8 0 4.0
assign (resid 7 and name HN) (resid 6 and name HB*) 1.8 0 3.3
assign (resid 7 and name HN) (resid 5 and name HB*) 1.8 0 4.0
assign (resid 7 and name HN) (resid 5 and name HG*) 1.8 0 4.0
assign (resid 7 and name HN) (resid 8 and name HB*) 1.8 0 5.5
assign (resid 7 and name HN) (resid 7 and name HB*) 1.8 0 3.0
assign (resid 7 and name HN) (resid 7 and name HD*) 1.8 0 3.5
assign (resid 7 and name HN) (resid 4 and name HA) 1.8 0 4.5

TABLE 6-continued assign (resid 7 and name HN) (resid 3 and name CO) 1.8 0 3.0
assign (resid 7 and name HN) (resid 4 and name CO) 1.8 0 3.0
assign (resid 8 and name HN) (resid 7 and name HA) 1.8 0 3.0
assign (resid 8 and name HN) (resid 6 and name HA) 1.8 0 3.5
assign (resid 8 and name HN) (resid 9 and name HB*) 1.8 0 5.0
assign (resid 8 and name HN) (resid 6 and name HB*) 1.8 0 4.5
assign (resid 8 and name HN) (resid 7 and name HD*) 1.8 0 4.0
assign (resid 8 and name HN) (resid 8 and name HB*) 1.8 0 3.0
assign (resid 8 and name HN) (resid 8 and name HG*) 1.8 0 3.5
assign (resid 8 and name HN) (resid 8 and name HD*) 1.8 0 3.5
assign (resid 8 and name uN) (resid 5 and name HA) 1.8 0 4.5
assign (resid 8 and name HN) (resid 5 and name HG*) 1.8 0 5.5
assign (resid 8 and name HN) (resid 5 and name CO) 1.8 0 3.0
assign (resid 8 and name HN) (resid 4 and name CO) 1.8 0 3.0
assign (resid 9 and name HN) (resid 6 and name HA) 1.8 0 4.0
assign (resid 9 and name HN) (resid 8 and name HA) 1.8 0 3.0
assign (resid 9 and name HN) (resid 7 and name HA) 1.8 0 3.5
assign (resid 9 and name HN) (resid 9 and name HB*) 1.8 0 3.0
assign (resid 9 and name HN) (resid 6 and name HB*) 1.8 0 5.0
assign (resid 9 and name HN) (resid 8 and name HB*) 1.8 0 3.5
assign (resid 9 and name HN) (resid 8 and name HG*) 1.8 0 3.5
assign (resid 9 and name HN) (resid 7 and name HB*) 1.8 0 4.5
assign (resid 9 and name HN) (resid 7 and name HD*) 1.8 0 5.0
assign (resid 9 and name HE3) (resid 9 and name HA) 1.8 0 2.8
assign (resid 9 and name HE3) (resid 5 and name HA) 1.8 0 4.5
assign (resid 9 and name HE3) (resid 8 and name HA) 1.8 0 4.0
assign (resid 9 and name HE3) (resid 9 and name HB*) 1.8 0 3.0
assign (resid 9 and name HE3) (resid 6 and name HB*) 1.8 0 5.0
assign (resid 9 and name HE3) (resid 7 and name HB*) 1.8 0 5.0
assign (resid 9 and name HE3) (resid 7 and name HD*) 1.8 0 5.0
assign (resid 9 and name HE3) (resid 10 and name HG*) 1.8 0 5.0
assign (resid 9 and name HE3) (resid 12 and name HD*) 1.8 0 5.5
assign (resid 9 and name HZ2) (resid 9 and name HA) 1.8 0 5.0
assign (resid 9 and name HZ2) (resid 12 and name HG*) 1.8 0 5.0
assign (resid 9 and name HZ2) (resid 12 and name HD*) 1.8 0 5.0
assign (resid 9 and name HZ3) (resid 9 and name HB*) 1.8 0 4.5
assign (resid 9 and name HZ3) (resid 8 and name HB*) 1.8 0 4.5
assign (resid 9 and name HZ3) (resid 8 and name HG*) 1.8 0 4.5
assign (resid 9 and name HZ3) (resid 7 and name HB*) 1.8 0 4.5
assign (resid 9 and name HZ3) (resid 7 and name HD*) 1.8 0 4.5
assign (resid 9 and name HH2) (resid 9 and name HA) 1.8 0 5.0
assign (resid 9 and name HH2) (resid 8 and name HA) 1.8 0 4.5
assign (resid 9 and name HH2) (resid 12 and name HG*) 2.5 0 5.0
assign (resid 9 and name HH2) (resid 12 and name HD*) 1.8 0 5.0
assign (resid 9 and name HH2) (resid 7 and name HB*) 1.8 0 4.5
assign (resid 9 and name HH2) (resid 7 and name HD*) 1.8 0 4.5
assign (resid 9 and name HN) (resid 5 and name CO) 1.8 0 3.0
assign (resid 9 and name HN) (resid 6 and name CO) 1.8 0 3.0
assign (resid 10 and name HN) (resid 9 and name HA) 1.8 0 3.0

TABLE 6-continued

```
assign (resid 10 and name HN) (resid 7 and name HA) 1.8 0 4.0
assign (resid 10 and name HN) (resid 10 and name HB*) 1.8 0 3.5
assign (resid 10 and name HN) (resid 10 and name HG*) 1.8 0 3.5
assign (resid 10 and name HN) (resid 10 and name HD*) 1.8 0 4.5
assign (resid 10 and name HN) (resid 9 and name HB*) 1.8 0 3.5
assign (resid 10 and name HN) (resid 7 and name HD*) 1.8 0 5.0
assign (resid 10 and name HN) (resid 8 and name HA) 1.8 0 4.0
assign (resid 11 and name HN) (resid 10 and name HA) 1.8 0 3.0
assign (resid 11 and name HN) (resid 8 and name HA) 1.8 0 4.0
assign (resid 11 and name HN) (resid 9 and name HA) 1.8 0 3.5
assign (resid 11 and name HN) (resid 11 and name HB) 1.8 03.5
assign (resid 11 and name HN) (resid 11 and name HG*) 1.8 0 3.5
assign (resid 11 and name HN) (resid 11 and name HD*) 1.8 0 4.5
assign (resid 11 and name HN) (resid 10 and name HB*) 1.8 0 3.5
assign (resid 11 and name HN) (resid 6 and name CO) 1.8 0 3.0
assign (resid 11 and name HN) (resid 7 and name CO) 1.8 0 3.0
assign (resid 12 and name HN) (resid 11 and name HA) 1.8 0 3.0
assign (resid 12 and name HN) (resid 11 and name HB) 1.8 0 4.5
assign (resid 12 and name HN) (resid 12 and name HB) 1.8 0 3.5
assign (resid 12 and name HN) (resid 12 and name HG*) 1.8 0 3.5
assign (resid 12 and name HN) (resid 12 and name HD*) 1.8 0 4.5
assign (resid 12 and name HN) (resid 9 and name HA) 1.8 0 4.0
assign (resid 12 and name HN) (resid 10 and name HA) 1.8 0 3.0
assign (resid 12 and name HN) (resid 9 and name HB*) 1.8 0 4.0
```

The complete disclosures of all patents, patent applications, publications, and nucleic acid and protein database entries, including for example GenBank accession numbers and EMBL accession numbers, that are cited herein are hereby incorporated by reference as if individually incorporated. Various modifications and alterations of this invention will become apparent to those skilled in the art without departing from the scope and spirit of this invention, and it should be understood that this invention is not to be unduly limited to the illustrative embodiments set forth herein.

Sequence Free Text

The following are synthetic polypeptides:

| | |
|---|---|
| ANIKLSVQMKLF | (SEQ ID NO:1) |
| KLSVQMKLFKRH | (SEQ ID NO:2) |
| VQMKLFKRHLKW | (SEQ ID NO:3) |
| KLFKRHLKWKII | (SEQ ID NO:4) |
| KRHLKWKIIVKL | (SEQ ID NO:5) |
| LKWKIIVKLNDG | (SEQ ID NO:6) |
| KIIVKLNDGREL | (SEQ ID NO:7) |
| VKLNDGRELSLD | (SEQ ID NO:8) |
| QMKLFKRHLKWK | (SEQ ID NO:9) |
| MKLFKRHLKWKI | (SEQ ID NO:10) |
| MKLFKRHLKWKIIV | (SEQ ID NO:11) |
| XLFKRHLKWKII | (SEQ ID NO:12) |
| KLFXRHLKWKII | (SEQ ID NO:13) |
| KLFKRHLXWKII | (SEQ ID NO:14) |
| KLFKRHLKWXII | (SEQ ID NO:15) |
| KLFKKHLKWKII | (SEQ ID NO:16) |
| KLFKHLKWKII | (SEQ ID NO:17) |
| SIQKLNVSMKLFRKQAKWKIIVKLNDGRELSLD | (SEQ ID NO: 18) |
| ANIKLSVQMKLFKRHLKWKIIVKLNDGRELSLD | (SEQ ID NO: 19) |
| KLKLLLLLKLK | (SEQ ID NO: 20) |

---

What is claimed is:

1. A polypeptide selected from the group consisting of those represented by SEQ ID NOs:1–6 and 9–17 and active analogs thereof, wherein X is an amino acid, wherein an active analog thereof demonstrates at least one of bactericidal activity, endotoxin neutralizing activity, decreasing the amount of TNF-α in vitro, inhibiting endothelial cell proliferation in vitro, inhibiting angiogenic-factor mediated inter-cellular adhesion molecule expression down-regulation in vitro, inhibiting angiogenesis in vitro, and inhibiting tumorigenesis in vitro; and wherein the active analog is selected from the group consisting of deletion of one amino acid, one or two additional amino acids, conservative amino acid substitutions, chemical modifications, and enzymatic modifications.

2. A polypeptide selected from the group consisting of those represented by SEQ ID NOs:1–6.

3. A polypeptide selected from the group consisting of those represented by SEQ ID NOs:9–17, wherein X is an amino acid.

4. The polypeptide of claim 3 wherein X is norleucine.

5. The polypeptide of claim 1 which is active for the treatment of bacterial infection and/or endotoxemia.

6. A polypeptide having an amphipathic α-helical or $3_{10}$ helical structure having one surface comprising positively charged amino acid residues and an opposing surface comprising hydrophobic amino acid residues, wherein the positively charged amino acid residues and the opposing hydrophobic amino acid residues identify a surface active domain, wherein the polypeptide has 12, 13, or 14 amino acid residues, wherein the surface active domain comprises amino acids K1, K4, K8, and R5, wherein amino acid K1 is N-terminal, and wherein the polypeptide demonstrates at least one of bactericidal activity, endotoxin neutralizing activity, decreasing the amount of TNF-α in vitro, inhibiting endothelial cell proliferation in vitro, inhibiting angiogenic-factor mediated inter-cellular adhesion molecule expression down-regulation in vitro, inhibiting angiogenesis in vitro, and inhibiting tumorigenesis in vitro.

7. The polypeptide of claim 6 wherein the surface active domain comprises atoms 1–24, 64–109, and 146–167 listed in Table 5.

8. The polypeptide of claim 6 having the structure coordinates listed in Table 5.

9. The polypeptide of claim 6 having the sequence KLFKRHLKWKII (SEQ ID NO:4).

10. The polypeptide of claim 6 having at least one hydrophobic residue at the C-terminal position.

11. The polypeptide of claim 6 having 12 amino acid residues.

12. The polypeptide of claim 6 having the sequence KLFKRHLKWXII (SEQ ID NO:15), wherein X is an amino acid.

13. The polypeptide of claim 12 wherein X is norleucine.

14. The polypeptide of claim 6 having 14 amino acid residues.

15. A polypeptide selected from the group consisting of those represented by SEQ ID NOs:1–6 and 9–17 and active analogs thereof, wherein X is an amino acid, wherein an active analog thereof demonstrates at least one of bactericidal activity, endotoxin neutralizing activity, decreasing the amount of TNF-α in vitro, inhibiting endothelial cell proliferation in vitro, inhibiting angiogenic-factor mediated inter-cellular adhesion molecule expression down-regulation in vitro, inhibiting angiogenesis in vitro, and inhibiting tumorigenesis in vitro; and wherein the active analog is selected from the group consisting of deletion of one amino acid, one or two additional amino acids, and conservative amino acid substitutions.

16. The polypeptide of claim 15 further modified by chemical and/or enzymatic derivatization.

17. A method for treating bacterial infection and/or endoxtoxemia comprising administering to a patient an amount of a pharmaceutical composition effective to inhibit the bacterial infection and/or neutralize endotoxin, wherein the pharmaceutical composition comprises one or more polypeptides of claim 1, 6 or 15.

18. The method of claim 17 wherein the polypeptide neutralizes endotoxin.

19. The method of claim 17 wherein the polypeptide is bactericidal.

20. The method of claim 17 wherein the polypeptide is both bactericidal and capable of neutralizing endotoxin.

21. The method of claim 17 wherein the composition comprises a polypeptide having endotoxin neutralizing activity and is selected from the group consisting of those represented by SEQ ID NOs:1–6; and combinations thereof.

22. The method of claim 17 wherein the composition comprises a polypeptide having bactericidal activity and is selected from the group consisting of those represented by SEQ ID NOs:1–6; and combinations thereof.

23. The method of claim 17 wherein the composition comprises KLFKRHLKWKII (SEQ ID NO:4).

24. A method for inhibiting bacterial infection and/or endotoxemia in vitro, the method comprising contacting cells with an amount of a composition effective to inhibit the bacterial infection and/or to neutralize endotoxin, wherein the composition comprises one or more polypeptides of claim 1, 6 or 15.

* * * * *

UNITED STATES PATENT AND TRADEMARK OFFICE
CERTIFICATE OF CORRECTION

| | | |
|---|---|---|
| PATENT NO. | : 7,144,982 B2 | |
| APPLICATION NO. | : 09/766353 | |
| DATED | : December 5, 2006 | |
| INVENTOR(S) | : Kevin H. Mayo | |

It is certified that error appears in the above-identified patent and that said Letters Patent is hereby corrected as shown below:

The title page showing the illustrative figure should be deleted to be replaced with the attached title page.

The drawing sheet 1, consisting of Fig. 1, should be deleted to be replaced with the drawing sheet, consisting of Fig 1, as shown on the attached page.

Signed and Sealed this

Thirteenth Day of March, 2007

JON W. DUDAS
*Director of the United States Patent and Trademark Office*

(12) United States Patent
Mayo

(10) Patent No.: US 7,144,982 B2
(45) Date of Patent: Dec. 5, 2006

(54) POLYPEPTIDES WITH THERAPEUTIC ACTIVITY AND METHODS OF USE

(75) Inventor: Kevin H. Mayo, Minnetonka, MN (US)

(73) Assignee: University of Minnesota, Minneapolis, MN (US)

( * ) Notice: Subject to any disclaimer, the term of this patent is extended or adjusted under 35 U.S.C. 154(b) by 846 days.

(21) Appl. No.: 09/766,353

(22) Filed: Jan. 19, 2001

(65) Prior Publication Data
US 2002/0146406 A1 Oct. 10, 2002

Related U.S. Application Data

(60) Provisional application No. 60/210,297, filed on Jun. 8, 2000, provisional application No. 60/177,255, filed on Jan. 20, 2000.

(51) Int. Cl.
A61K 38/04 (2006.01)
A61K 38/10 (2006.01)
C07K 7/08 (2006.01)

(52) U.S. Cl. .................. 530/327; 530/300; 514/14; 514/15

(58) Field of Classification Search ............ 530/300, 530/327; 514/14, 15
See application file for complete search history.

(56) References Cited

U.S. PATENT DOCUMENTS

| | | |
|---|---|---|
| 4,938,949 A | 7/1990 | Borch et al. |
| 5,595,887 A | 1/1997 | Coolidge et al. |
| 5,786,324 A | 7/1998 | Gray et al. |
| 5,830,860 A | 11/1998 | Gray et al. |
| 5,837,678 A | 11/1998 | Little, II |
| 5,854,214 A | 12/1998 | Little, II |
| 5,856,302 A | 1/1999 | Ammons et al. |
| 5,955,577 A | 9/1999 | Mayo |

FOREIGN PATENT DOCUMENTS

| | | |
|---|---|---|
| EP | 0 955 312 A2 | 11/1999 |
| WO | WO 99/17616 | 4/1999 |
| WO | WO 01/53335 | 7/2001 |

OTHER PUBLICATIONS

Oice et al. Database Caplus, Journal of Neuroimmunology (1989), 21(2-3), 235-40.*
Ngo et al. In: The protein folding and tertiary structure prediction, K. Merz and S. Le Grand, Eds. Birkhauser, Boston, 1994, pp. 491-495.*
Agerberth et al., "Amino acid sequence of PR-39. Isolation from pig intestine of a new member of the family of proline-arginine-rich antibacterial peptides," *European Journal of Biochemistry*, 202(3):849-854 (1991).
Alvarez-Bravo et al., "Mode of Action of an Antibacterial Peptide, KLKLLLLLKLK-NH$_2$," *The Journal of Biochemistry* (Tokyo), 117(6):1312-1316 (1995).
Andreu et al., "N-Terminal Analogues of Cecropin A: Synthesis, Antibacterial Activity, and Conformational Properties," *Biochemistry*, 24(7):1683-1588 (1985).
Andreu et al., "Animal Antimicrobial Peptides: An Overview," *Biopolymers Peptide Science*, 47(6):415-433 (1998).

(Continued)

*Primary Examiner*—Michael Borin
(74) *Attorney, Agent, or Firm*—Mueting, Raasch & Gebhardt, P.A.

(57) ABSTRACT

Polypeptides and methods of use including treating bacterial infection and/or endotoxemia, decreasing the amount of TNF-α, inhibiting endothelial cell proliferation, inhibiting angiogenic-factor mediated inter-cellular adhesion molecule expression down-regulation, and inhibiting angiogenesis.

24 Claims, 9 Drawing Sheets

βpep-19.  S I Q K L N V S M K L F R K Q A K W K I I V K L N D G R E L S L D-NH₂ (SEQ ID NO: 18)

βpep-25.  A N I K L S V Q M K L F K R H L K W K I I V K L N D G R E L S L D-NH₂ (SEQ ID NO: 19)

SC-1      A N I K L S V Q M K L-NH₂ (SEQ ID NO: 1)
SC-2          K L S V Q M K L F K R H-NH₂ (SEQ ID NO: 2)
SC-3              V Q M K L F K R H L K W-NH₂ (SEQ ID NO: 3)
SC-4                  K L F K R H L K W K I I-NH₂ (SEQ ID NO: 4)
SC-5                      K R H L K W K I I V K L-NH₂ (SEQ ID NO: 5)
SC-6                          L K W K I I V K L N D G-NH₂ (SEQ ID NO: 6)
SC-7                              K I I V K L N D G R E L-NH₂ (SEQ ID NO: 7)
SC-8                                  V K L N D G R E L S L D-NH₂ (SEQ ID NO: 8)

βpep-19. SIQKLNVSMKLFRKQAKWKIIVKLNDGRELSLD-NH2 (SEQ ID NO: 18)

βpep-25. ANIKLSVQMKLFKRHLKWKIIVKLNDGRELSLD-NH2 (SEQ ID NO: 19)

SC-1   ANIKLSVQMKLF-NH2 (SEQ ID NO: 1)
SC-2     KLSVQMKLFKRH-NH2 (SEQ ID NO: 2)
SC-3       VQMKLFKRHLKW-NH2 (SEQ ID NO: 3)
SC-4         KLFKRHLKWKII-NH2 (SEQ ID NO: 4)
SC-5           KRHLKWKIIVKL-NH2 (SEQ ID NO: 5)
SC-6             LKWKIIVKLNDG-NH2 (SEQ ID NO: 6)
SC-7               KIIVKLNDGREL-NH2 (SEQ ID NO: 7)
SC-8                 VKLNDGRELSLD-NH2 (SEQ ID NO: 8)

UNITED STATES PATENT AND TRADEMARK OFFICE
CERTIFICATE OF CORRECTION

PATENT NO.        : 7,144,982 B2
APPLICATION NO. : 09/766353
DATED             : December 5, 2006
INVENTOR(S)       : Kevin H. Mayo It is certified that error appears in the above-identified patent and that said Letters Patent is hereby corrected as shown below:

On the title page item (73),
Before "University" insert --Regents of the--

Signed and Sealed this

Ninth Day of October, 2007

JON W. DUDAS
*Director of the United States Patent and Trademark Office*